United States Patent
Chahal et al.

(10) Patent No.: US 12,083,189 B2
(45) Date of Patent: Sep. 10, 2024

(54) TAIL-CONJUGATED RNAS

(71) Applicant: Tiba Biotech, Cambridge, MA (US)

(72) Inventors: Jasdave S Chahal, Woburn, MA (US); Justine S McPartlan, Somerville, MA (US)

(73) Assignee: TIBA BIOTECH, LLC, Cambridge, MA (US)

( * ) Notice: Subject to any disclaimer, the term of this patent is extended or adjusted under 35 U.S.C. 154(b) by 0 days.

(21) Appl. No.: 18/140,326

(22) Filed: Apr. 27, 2023

(65) Prior Publication Data

US 2023/0346980 A1 Nov. 2, 2023

Related U.S. Application Data

(60) Provisional application No. 63/336,464, filed on Apr. 29, 2022.

(51) Int. Cl.
*A61K 48/00* (2006.01)
*A61P 37/02* (2006.01)

(52) U.S. Cl.
CPC .......... *A61K 48/0066* (2013.01); *A61P 37/02* (2018.01)

(58) Field of Classification Search
CPC ............................ A61K 48/0066; A61P 37/02
See application file for complete search history.

(56) References Cited

U.S. PATENT DOCUMENTS

| 10,266,843 | B2 * | 4/2019 | DeRosa et al. | ........ | C12N 15/85 |
| 2004/0043468 | A1 * | 3/2004 | Mauro et al. | ............ | C12N 9/22 |
| | | | | | 435/199 |
| 2019/0274968 | A1 * | 9/2019 | Weissman et al. | .. | A61K 9/5123 |
| 2021/0330600 | A1 | 10/2021 | Talukder et al. | | |
| 2021/0338789 | A1 | 11/2021 | Khan et al. | | |

FOREIGN PATENT DOCUMENTS

| WO | 2011153345 | A2 | | 12/2011 | | |
| WO | 2015149077 | A1 | | 10/2015 | | |
| WO | 2021155177 | A1 | | 8/2021 | | |
| WO | 2021207020 | A2 | | 10/2021 | | |
| WO | WO2022026928 | A1 | * | 2/2022 | ............ | C12N 15/11 |

OTHER PUBLICATIONS

El-Sagheer et al. (2015) "A triazole linkage that mimics the DNA phosphodiester group in living systems" Quarterly Reviews of Biophysics, 48(4), 429-436. (Year: 2015).*
GenBank LC311024.1, "Mammalian expression vector EGFP-MCS-pcDNA3.1 DNA, complete sequence", entered: Jul. 20, 2017, available from: National Library of Medicine (US), National Center for Biotechnology Information, [item V continued . . . ] (Year: 2017).*
[. . . item V continued] https://www.ncbi.nlm.nih.gov/nucleotide/LC311024.1?report=genbank&log$=nuclalign&blast_rank=1 &RID= USS69ZRD01N. (Year: 2017).*
Chalfie, M. (1995) "Green fluorescent protein" Photochemistry and photobiology, 62(4), 651-656. (Year: 1995).*
GenBank KM403567.1, "Seap expression vector pSA928, complete sequence", entered: Oct. 2, 2014, available from: National Library of Medicine (US), National Center for Biotechnology Information, https://www.ncbi.nlm.nih.gov/nuccore/KM403567.1# feature_ KM403567.1. (Year: 2014).*
GenBank AY015993.1, "Gaussia princeps (T. Scott, 1894) luciferase mRNA, complete cds", entered: Oct. 18, 2005, available from: National Library of Medicine (US), National Center for Biotechnology Information, https://www.ncbi.nlm.nih.gov/nuccore/AY015993.1. (Year: 2005).*
GenBank MF169983.1, "Synthetic construct clone pPK2-BAR-mCherry mCherry (mCherry) and BAR (bar) genes, complete cds", entered: Aug. 15, 2017, available from: National Library of Medicine (US), National Center for Biotechnology Information, https://www.ncbi.nlm.nih.gov/nuccore/MF169983.1. (Year: 2017).*
Bar-On et al. 2020, SARS-CoV-2 (COVID-19) by the numbers, eLife; 9: e57309.
Bergstrom 2009, Unnatural nucleosides with unusual base pairing properties Current Protocols in Nucleic Acid Chemistry Suppl. 37 1.4.1.
Heyes et al., 2005, Cationic lipid saturation influences intracellular delivery of encapsulated nucleic acid, J Controlled Release 107:276-87.
Hirao et al. 2012, Natural versus Artificial creation of base pairs in DNA: origin of nucleobases from the perspectives of unnatural base pair studies, Accounts of Chemical Research vol. 45 p. 2055.
Smith, and Waterman, 1981, Identification of Common Molecular Subsequences, J Mol Biol 147, pp. 195-197.
Worner et al. 2020, Adeno-associated virus capsid assembly is divergent and stochastic, bioRxiv; doi.org/10.1101/2020.10.09.332619.
International Search Report issued in corresponding International Patent Application No. PCT/US2023/020227 on Sep. 21, 2023, consisting of 5 pp.
Written Opinion issued in corresponding International Patent Application No. PCT/US2023/020227 on Sep. 21, 2023, consisting of 7 pp.

* cited by examiner

*Primary Examiner* — James D Schultz
*Assistant Examiner* — James Joseph Graber
(74) *Attorney, Agent, or Firm* — Volpe Koenig

(57) ABSTRACT

Tail-tail RNA conjugates translatable by eukaryotic ribosomes, and pharmaceutically acceptable compositions including the same are provided. Methods for preparing such molecules, using them for treating and preventing diseases are described. In addition, processes for producing desired polypeptides using the molecules are also described.

1 Claim, 32 Drawing Sheets

Specification includes a Sequence Listing.

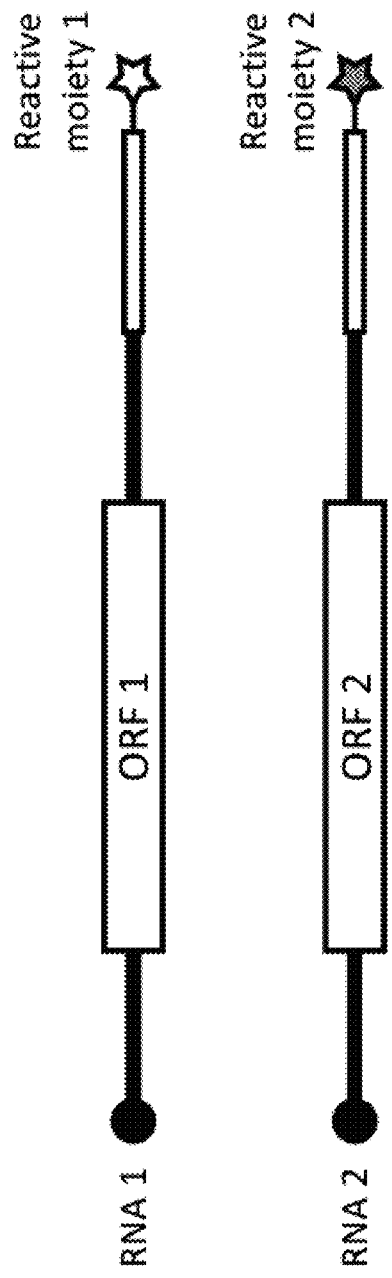
FIG. 1A
FIG. 1B

TAIL-CONJUGATED RNAS

CROSS REFERENCE TO RELATED APPLICATION

This application claims the benefit of U.S. provisional application No. 63/163,475, filed Apr. 29, 2022, which is incorporated by reference as if fully set forth.

The sequence listing electronically filed with this application titled "Sequence Listing," which was created on Apr. 26, 2023 and had a size of 46,289 bytes is incorporated by reference herein as if fully set forth.

FIELD OF INVENTION

The present disclosure relates to tail-tail RNA conjugates that are capable of being translated by eukaryotic ribosomes. The present disclosure further relates to processes for producing desired polypeptides using such RNA conjugates and using the same for treatment against disease in humans and animals.

BACKGROUND

Synthetic messenger RNA (mRNA) has broad potential for a range of vaccine and therapeutic applications. However, one fundamental limitation to its use is its relatively short half-life in cells due to degradation mediated from the 3' end. Thus, there is a need to extend the durability of synthetic mRNA molecules in cells to promote long-lasting biological function.

In cells, deoxyribonucleic acid molecules (DNA) are transcribed into ribonucleic acid molecules (RNA), which in turn are translated into amino acid sequences (polypeptides). Until the discovery of the present invention, linear and circular RNA molecules have been used as vector systems to drive protein expression by translation, or to regulate endogenous protein expression (e.g., RNAi). For the purposes of protein production in a cell, linear RNAs require either a 5' cap structure (e.g., 7-methylguanylate cap, $m^7G$) to mediate translation by canonical eukaryotic initiation factor 4F (eIF4F)-mediated translation initiation or an internal ribosome entry site (IRES), an RNA element that allows for translation initiation in a cap-independent manner. Linear mRNA is susceptible to degradation from the 3' end, which limits its longevity in the cell. 3-5' exonucleases and the cellular exosomes are involved in several pathways including 3' processing of rRNA, snRNA and snoRNA, and the routine decay of mRNAs which is an essential feature of RNA metabolism in all known cell types. Circular RNAs (circRNAs) can escape 3-5' exonuclease activity because they contain no free RNA ends. However, these require the incorporation of IRES elements comprising extensive secondary structure, which is sensitive to perturbations during manufacturing and, even when intact, are far less efficient at mediating translation initiation than capped linear RNA. Furthermore, manufacturing of circular RNA constructs tends to produce heterogenous products and contaminating intermediates resulting from nonspecific chemical conjugation or in vitro splicing reactions. Thus, production is inefficient and purification is laborious, leading to poor yields and decay due to the low inherent thermostability of RNA.

SUMMARY

In an aspect, the invention relates to a tail-tail RNA conjugate comprising a plurality of RNA molecules. Each RNA molecule comprises operably connected elements comprising: a 5' untranslated region (UTR), a coding or non-coding RNA region, a 3' UTR, and a terminal 3' nucleotide. Each RNA molecule is connected to one another through the terminal 3' nucleotide.

In an aspect, the invention relates to a pharmaceutically acceptable composition comprising any one of the tail-tail RNA conjugates disclosed herein, and a pharmaceutically acceptable carrier or excipient.

In an aspect, the invention relates to a method of preparing the tail-tail RNA conjugate. The method comprises providing two or more linear DNA plasmids; transcribing DNA plasmids to produce linear RNA sequences and linking 3' nucleotides comprising chemically reactive moieties of the RNA sequences to produce a tail-tail RNA conjugate.

In an aspect, the invention relates to a method of producing a polypeptide by expressing any one of the tail-tail RNA conjugates described herein in a host cell.

In an aspect, the invention relates to a method of preventing, inhibiting, or treating the symptoms of a disease or condition in a subject. The method comprises providing a tail-tail RNA conjugate comprising a plurality of RNA molecules. Each one of the plurality of RNA molecules comprises operably connected elements comprising: a 5' untranslated region (UTR), a coding or non-coding RNA region, a 3' UTR, and a terminal 3' nucleotide. Each RNA molecule is connected to one another through the terminal 3' nucleotide. The method further comprises administering a therapeutically effective amount of the tail-tail RNA conjugate to a subject.

BRIEF DESCRIPTION OF THE DRAWINGS

The following detailed description of preferred embodiments of the present invention will be better understood when read in conjunction with the appended drawings. For the purpose of illustrating the invention, particular embodiments are shown in the drawings. It is understood, however, that the invention is not limited to the precise arrangements and instrumentalities shown. In the drawings:

FIG. 1A is a schematic diagram showing an example of a conventional linear mRNA molecule. The 5' cap, 5' untranslated region (UTR), protein-coding open reading frame (ORF), 3' UTR, and poly-A tail are labeled.

FIG. 1B is a schematic diagram showing an example of two linear mRNA molecules comprising 3' reactive moieties, which is present on the terminal 3' nucleotide. mRNA 1 and mRNA 2 may be different or identical, and the reactive moieties 1 and 2 may be reactive with each other, or alternatively with a third reactive moiety.

FIG. 2A is a schematic diagram showing an example of two linear mRNA molecules comprising identical reactive moieties on their terminal 3' nucleotides. mRNA "A" and mRNA "B" encode different proteins in this example and thus the ORFs differ. The 5' UTR and 3'UTR/poly-A tails may or may not be identical in sequence, and the poly-A tail is optional depending on the specific application.

FIG. 2B is a schematic diagram showing an exemplary method of creating a heterofunctional mRNA trimer by reacting a defined molar ratio of 3' chemically functionalized RNAs to a trifunctional linker. This reaction favors yield of a heterotrimer carrying a ratio of mRNA A and B defined by the input molarity of each nucleic acid.

FIG. 3A is a structure of a DNA linker that includes six consecutive deoxyadenosine (dA) residues connected by phosphodiester bonds. In this figure, the first three dAs are in typical 5'-to-3' sequence followed by an atypical phosphodiester bond that connects the 3' hydroxyls of the third and fourth residues, and the fourth through sixth residues connected by typical phosphodiester bonds but are oriented 3'-to-5' relative to the first three dA residues.

FIG. 3B is a schematic diagram showing creation of an RNA dimer including two mRNA molecules encoding the SEAP proteins.

FIG. 3C is a photograph of an agarose gel showing an RNA species (top band) that doubles the length of the input RNA (lower band; Rxn lane) compared to the band corresponding to control mRNA monomer (C lane) of the expected mass based on comparison to the RNA ladder (ladder (numbers to the left, values in thousands of nucleotides).

FIG. 3D is a bar graph showing the expression of the SEAP RNA dimer (Dimer rxn) in baby hamster kidney (BHK) cells 12 hours post transfection compared to control monomer mRNA (control) and culture medium (neg,).

FIG. 3E is a bar graph showing the expression of the SEAP RNA dimer (Dimer rxn) in baby hamster kidney (BHK) cells 24 hours post transfection compared to control monomer mRNA (control) and culture medium (neg,).

FIG. 4A is a schematic diagram showing creation of an RNA dimer similar to the dimer shown in FIG. 3B but including two different mRNA molecules, one of which encodes the SEAP protein and another one encodes a Firefly luciferase protein (SEAP-Luc dimer).

FIG. 4B is a photograph of an agarose gel showing an RNA species (top band) that doubles the length of the input RNA (lower band; Rxn lane) compared to the band corresponding to control mRNA monomer (C lane) of the expected mass based on comparison to the RNA ladder (numbers to the left, values in thousands of nucleotides). The control mRNA monomer is the unreacted starting material of the dimerization reaction, an equimolar mixture of SEAP mRNA and Luc mRNA FIG. 4C is a bar graph showing the SEAP expression of the SEAP-Luc RNA dimer (Dimer rxn) in baby hamster kidney (BHK) cells 5 days post transfection compared to control monomer mRNA (control) and untreated culture medium (neg,).

FIG. 4D is a bar graph showing the Luc expression of the SEAP-Luc RNA dimer (Dimer rxn) in baby hamster kidney (BHK) cells 5 days post transfection compared to control monomer mRNA (control) and untreated culture medium (neg,).

FIG. 5A is a schematic diagram showing creation of an RNA dimer similar to the dimer shown in FIG. 4B but including two different mRNA molecules, one of which encodes the eGFP protein and another one encodes an mCherry fluorescent protein (eGFP-mCherry dimer).

FIG. 5B is a photograph of an agarose gel showing an RNA species (top band) that doubles the length of the input RNA (lower band; Rxn lane) compared to the band corresponding to control mRNA monomers (C lane) of the expected mass based on comparison to the RNA ladder (numbers to the left, values in thousands of nucleotides). The control mRNA monomer is the unreacted starting material of the dimerization reaction, an equimolar mixture of eGFP mRNA and mCherry mRNA.

FIG. 5C illustrates the results of flow cytometry analyses of eGFP and mCherry expression of the eGFP-mCherry RNA dimer (Dimer rxn) in baby hamster kidney (BHK) cells 1 day post transfection compared to control monomer mRNA eGFP (eGFP), monomer mCherry (mCherry), co-transgection with separate mRNAs of eGFP and mCherry (co-trsansfection) and culture medium (neg,).

FIG. 5D is a bar graph showing quantification the eGFP, and mCherry expression of the eGFP-mCherry RNA dimer (Ligated; dual positive GFP+ mCherry+) in baby hamster kidney (BHK) cells 1 day post transfection compared to control monomer eGFP mRNA (Only eGFP), mCherry (Only mCherry) and Dual negative (Untransfected GFP−mCherry−).

FIG. 6A is a schematic diagram showing creation of an RNA dimer similar to the dimer shown in FIGS. 4B and 5B but including two different mRNA molecules, one of which encodes the Influenza strain PR8 hemagglutinin (HA) protein and another one encodes a RANTES protein (HA-RANTES dimer).

FIG. 6B are two sets of line graphs Replicate 1 (left) and Replicate 2(right) showing the RANTES expression of the HA-RANTES RNA dimer (Dimer rxn) in baby hamster kidney (BHK) cells measured 2, 4 and 6 days post transfection compared to control monomer mRNA (control).

FIG. 6C is a photograph of an immunoblot that shows the greater HA expression for the HA-RANTES RNA dimer (Dimer rxn) than the control unligated RNA (Control) and culture medium (Neg.)

FIG. 7A is a structure of a four-directional branched PEG-(DBCO) linker.

FIG. 7B is a schematic drawing of the reaction for generating a tail-conjugated RNA tetramer.

FIG. 7C are line and bar graphs showing absorbance values illustrating the successful conjugation of the dA5 linker to the 4-Arm PEG as shown in FIG. 7B. The line graph on the left show absorbance at 310 nm of the simulated reaction to deplete DBCO; the line graph in the middle shows absorbance at 310 nm drop indicating depletion of unreacted DBCO in the reaction producing 4-way linker (close circles represent reaction with dA5; open circles represent control reaction); and the bar graph on the right shows absorbance at OD260 of the reaction product with dA5 (dA5rxn) compared to control reaction product (control rxn) and predicted absorbance value for the reaction if no linker was present (predicted no linker).

FIG. 7D is a generic structure of a 4-way linker obtained by the process illustrated in FIG. 7B.

FIG. 8A is a structure of the 3-Arm PEG-DBCO that serves as the starting material to produce the 3-way tad-conjugated mRNA, FIG. 8B is a structure of an 8-Arm PEG-DBCO at serves as the starting material to produce the 8-way tail-conjugated mRNA. Note the internal branch which is repeated six times (in bold for emphasis).

FIG. 8C is a structure of a 3-way linker bearing three terminal nucleotide 5' phosphate groups.

FIG. 8D is a structure of an 8-way linker bearing eight terminal nucleotide 5' phosphate groups.

FIG. 9A is a structure of a 3' dibenzocyclooctyne (DBCO) moiety—containing nucleotide molecule bearing a 5' phosphate group. The value of n is 0 to 30; if n is 0, it is referred to as a mononucleotide.

FIG. 9B is a schematic drawing illustrating a method of purifying and applying a dimeric mRNA encoding an exemplary monoclonal antibody, trastuzumab. The steps indicated are i) purification of the desired HC+LC mRNA heterodimer from any minor contaminating monomeric or homodimeric mRNA species based on size (e.g., reversed-phase chromatography), ii) formulation of the mRNA dimer using ionizable lipids, dendrimers, or polymers to produce a nanoparticle suspension, and iii) administration of the suspension to human or animal subjects to prevent or treat a disease state.

DETAILED DESCRIPTION OF THE PREFERRED EMBODIMENTS

Figure 1C:
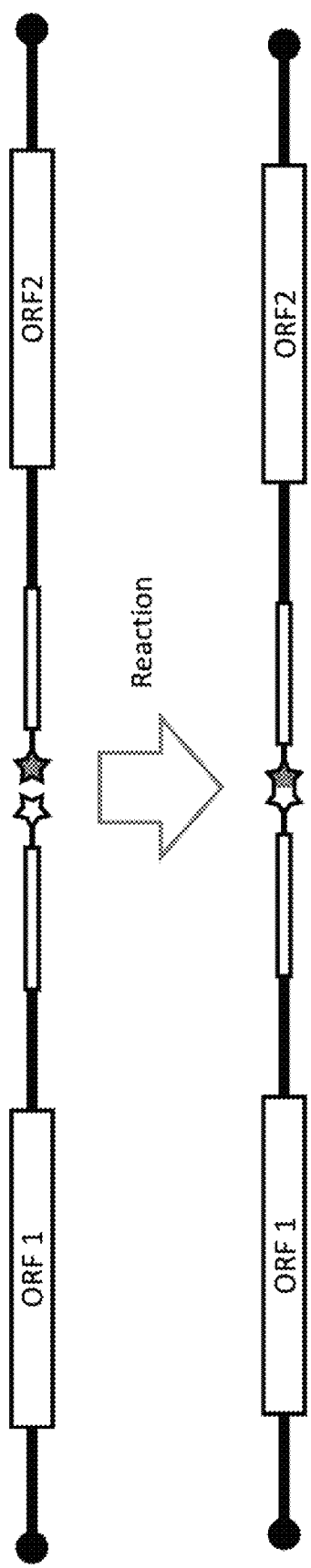
FIG. 1C is a schematic diagram showing an exemplary method of creating a tail-to-tail mRNA dimer by directly reacting the chemically addressable reactive moieties present at the mRNA 3' termini to each other. If mRNA 1 and 2 are identical, this reaction yields a homodimer. If mRNA 1 and 2 are different, this reaction yields a heterodimer.

Certain terminology is used in the following description for convenience only and is not limiting. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

The singular terms "a," "an," and "the" include plural referents unless context clearly indicates otherwise. Similarly, the word "or" is intended to include "and" unless the context clearly indicates otherwise.

The phrase "at least one" followed by a list of two or more items, such as "A, B, or C," means any individual one of A, B or C as well as any combination thereof.

The words "right," "left," "top," and "bottom" designate directions in the drawings to which reference is made.

Although methods and materials similar or equivalent to those described herein can be used in the practice or testing of this disclosure, suitable methods and materials are described below.

The term "nucleic acid molecule" or "polynucleotide" refers to the polymeric form of nucleotides of any length and comprise monomers of unmodified or modified nucleotides. If the sugar is a simple ribose, the polymer is RNA (ribonucleic acid) if the sugar is derived from ribose as deoxyribose, the polymer is DNA (deoxyribonucleic acid).

As used herein the term "nucleotide" refers to a molecule comprising a five-carbon sugar, a phosphate group and a nitrogenous heterocyclic base. The term "nucleotide" shall be understood to include both natural nucleotides, such as ribose and deoxyribose as well as chemically or biochemically modified, non-natural, and/or derivatized nucleotides. The nucleotides can be unmodified or modified at the sugar, phosphate and/or base moiety.

The term nucleobase includes the purine (e.g. adenine and guanine) and pyrimidine (e.g., uracil, thymine and cytosine) moieties present in nucleosides and nucleotides which form hydrogen bonds in nucleic acid hybridization. In the context of the present disclosure the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g., A, T, G, C or U, wherein each letter may optionally include modified nucleobases of equivalent function. For example, in the exemplified oligonucleotides, the nucleobase moieties may be selected from A, T, G, C, U, N1-methylpseudouridine, and 5-methyl cytosine. The RNA molecules described herein may comprise modified nucleic acids. As used herein, the term "modified nucleotide" and "modified nucleic acid molecule" refers to all known modified nucleotides known in the art both naturally occurring and artificial such as chemically or biochemically modified, non-natural, or derivatized nucleotides.

An embodiment provides a tail-tail RNA conjugate comprising a plurality of RNA molecules each of which comprises operably connected elements comprising: a 5' untranslated region (UTR); a protein coding or non-coding region; a 3' UTR and a terminal 3' end through which the RNA molecules are conjugated to one another. The terminal 3' end may comprise a terminal 3' nucleotide comprising a chemical modification. Each of the RNA molecules may further be modified by capping the 5-end with a modified ribonucleotide, for example, 7-methylguanosine cap, which may be incorporated during RNA synthesis or enzymatically engineered after RNA transcription. The 5' cap may provide significant resistance to 5' exonucleases.

In an embodiment, the coding RNA region of the tail-tail RNA conjugates described herein may comprise a protein coding open reading frame (ORF). The protein coding ORF may encode a protein of eukaryotic, viral, or prokaryotic origin. In another embodiment, the protein coding ORF may encode human protein or non-human protein. In some embodiments, the protein coding ORF may encode one or more antibodies. For example, the protein coding ORF may encode human antibodies. In an embodiment, the protein coding ORF may encode a protein selected from hFIX, SP-B, VEGF-A, human methylmalonyl-CoA mutase (hMUT), CFTR, cancer self-antigens, and additional gene editing enzymes like Cpf1, zinc finger nucleases (ZFNs) and transcription activator-like effector nucleases (TALENs). In another embodiment, the protein coding ORF may encode a protein for therapeutic use. In an embodiment, the human antibody encoded by the protein coding ORF may be an anti-HIV antibody. In an embodiment, the antibody encoded by the protein coding ORF may be a bispecific antibody. In an embodiment, the bispecific antibody may be specific for CD19 and CD22. In another embodiment, the bispecific antibody may be specific for CD3 and CLDN6. In an embodiment, the protein coding ORF may encode a protein for diagnostic use. In an embodiment, the protein coding ORF may encode Gaussia luciferase (Gluc), Firefly luciferase (Fluc), green fluorescent protein (GFP), enhanced green fluorescent protein (eGFP), human erythropoietin (hEPO), or Cas9 endonuclease.

In an embodiment, the protein coding ORF may encode a secreted alkaline phosphatase (SEAP) protein comprising an amino acid sequence with at least 70, 72, 75, 80, 85, 90, 91, 92, 93, 94, 95, 96, 97, 98, 99, or 100% identity to the reference sequence as set forth in SEQ ID NO: 7. The SEAP protein may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 1.

In an embodiment, the protein coding ORF may encode a firefly luciferase protein comprising an amino acid sequence with at least 70, 72, 75, 80, 85, 90, 91, 92, 93, 94, 95, 96, 97, 98, 99, or 100% identity to the reference sequence as set forth in SEQ ID NO: 8. The firefly luciferase protein may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 2.

In an embodiment, the protein coding ORF may encode an enhanced green fluorescent protein (GFP) comprising an amino acid sequence with at least 70, 72, 75, 80, 85, 90, 91, 92, 93, 94, 95, 96, 97, 98, 99, or 100% identity to the reference sequence as set forth in SEQ ID NO: 9. The eGFP may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 3.

In an embodiment, the protein coding ORF may encode an mCherry fluorescent protein comprising an amino acid sequence with at least 70, 72, 75, 80, 85, 90, 91, 92, 93, 94, 95, 96, 97, 98, 99, or 100% identity to the reference sequence as set forth in SEQ ID NO: 10. The mCherry fluorescent protein may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 4.

In an embodiment, the protein coding ORF may encode an Influenza strain PR8 hemagglutinin (HA) protein comprising an amino acid sequence with at least 70, 72, 75, 80, 85, 90, 91, 92, 93, 94, 95, 96, 97, 98, 99, or 100% identity to the reference sequence as set forth in SEQ ID NO: 11. The Influenza strain PR8 HA protein may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 5.

As used herein, hemagglutinin, a transmembrane protein embedded on the surface of the viral envelope of Influenza viruses, is a trimeric glycoprotein that participates in receptor recognition and membrane fusion that is the primary antigen of interest in the production of influenza vaccines.

In an embodiment, the protein coding ORF may encode a "regulated on activation, normal T cell expressed and secreted" (RANTES) protein comprising an amino acid sequence with at least 70, 72, 75, 80, 85, 90, 91, 92, 93, 94, 95, 96, 97, 98, 99, or 100% identity to the reference sequence as set forth in SEQ ID NO: 12. The RANTES protein may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 6. The term "RANTES" protein refers to a CC chemokine that recruits leukocytes to the site of inflammation. RANTES is chemotactic for T cells, eosinophils, and basophils, but also for monocytes, natural-killer (NK) cells, dendritic cells and mastocytes. With the help of particular cytokines (i.e., IL-2 and IFN-γ) that are released by T cells, RANTES also induces the proliferation and activation of certain NK cells to form CHAK (CC-Chemokine-activated killer) cells. RANTES is also an HIV-suppressive factor released from CD8+ T cell. The co-expression of cytokines such as RANTES that attract leukocytes in concert with expression of pathogen or cancer antigens can enhance innate and adaptive immune responses against the antigen to drive better immune-mediated disease outcomes.

In an embodiment, the protein coding ORF may encode an antibody. The antibody may comprise a heavy chain of trastuzumab comprising an amino acid sequence with at least 70, 72, 75, 80, 85, 90, 91, 92, 93, 94, 95, 96, 97, 98, 99, or 100% identity to the reference sequence as set forth in SEQ ID NO: 21. The trastuzumab heavy chain may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 19. The antibody may comprise a light chain of trastuzumab comprising an amino acid sequence with at least 70, 72, 75, 80, 85, 90, 91, 92, 93, 94, 95, 96, 97, 98, 99, or 100% identity to the reference sequence as set forth in SEQ ID NO: 22. The trastuzumab light chain may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 20.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity is measured by the Smith Waterman algorithm (Smith T F, Waterman M S 1981 "Identification of Common Molecular Subsequences," J Mol Biol 147: 195-197, which is incorporated herein by reference as if fully set forth).

In an embodiment, the tail-tail RNA conjugate may comprise a non-coding RNA region. For example, non-coding regions may include intervening untranslated yet transcribed sequences. The intervening non-coding sequence may comprise a promoter for RNA-dependent RNA transcription. The intervening non-coding sequence may be a sequence of 1000 nt or less.

In an embodiment, the RNA molecule of the tail-tail RNA conjugate may comprise a second ORF.

In an embodiment, the 5' untranslated region (UTR) may comprise an IRES sequence. Alternatively, the 5' untranslated region (UTR) may not comprise an IRES sequence. If present, the IRES sequence may be an IRES sequence of *Taura* syndrome virus, *Triatoma* virus, Theiler's encephalomyelitis virus, simian Virus 40, *Solenopsis invicta* virus 1, *Rhopalosiphum padi* virus, Reticuloendotheliosis virus, fuman poliovirus 1, *Plautia stali* intestine virus, Kashmir bee virus, Human rhinovirus 2, *Homalodisca* coagulate virus-1, Human Immunodeficiency Virus type 1, *Homalodisca* coagulate virus-1, Himetobi P virus, *Hepatitis* C virus, *Hepatitis* A virus, *Hepatitis* GB virus, foot and mouth disease virus, Human enterovirus 71, *Equine* rhinitis virus, *Ectropis oblique* picorna-like virus, Encephalomyocarditis virus (EMCV), *Drosophila* C Virus, *Crucifer* tobarno virus, Cricket paralysis virus, Bovine viral diarrhea virus 1, Black Queen Cell Virus, Aphid lethal paralysis virus, Avian encephalomyelitis virus, Acute bee paralysis virus, *Hibiscus* chlorotic ringspot virus, Classical swine fever virus, Human FGF2, Human SFTPA1, Human AMLURUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, Salivirus, Cosavirus, Parechovirus, *Drosophila* hairless, *S. cerevisiae* TFIID, *S. cerevisiae* YAP1, Human c-src, Human FGF-1, Simian picomavirus, Turnip crinkle virus, an aptamer to eIF4G, Coxsackievirus B3 (CVB3) or Coxsackievirus A (CVB1/2). In yet another embodiment, the IRES may be an IRES sequence of Coxsackievirus B3 (CVB3). In a further embodiment, the IRES may be an IRES sequence of Encephalomyocarditis virus.

In an embodiment, the 3' UTR region of the operably linked elements of the RNA molecules included in the tail-tail RNA conjugate may comprise a poly-A tail. Alternatively, the 3' UTR region may not comprise a poly-A tail.

As used herein, the terms "operably linked" or "operably connected," refer to an arrangement of elements that are configured to perform, function or be structured in such a manner as to be suitable for an intended purpose. For example, a promoter operably connected to a coding sequence is capable of effecting the expression of the sequence coding for a protein. Expression is meant to include the transcription of any one or more of a recombinant nucleic acid encoding the RNA molecules included in the tail-tail RNA conjugate from a DNA or RNA template and may further include translation of a protein from a recombinant RNA molecules comprising an IRES sequence. Thus, for example, intervening untranslated yet transcribed sequences may be present between a promoter sequence and a coding sequence and the promoter sequence may still be considered to be "operably linked" to the coding sequence.

In an embodiment, the RNA molecules may be translatable and/or biologically active in eukaryotic cells. The biologically active RNA may be, for example, an mRNA, shRNA, siRNA, miRNA, self-amplifying RNA (saRNA), miRNA sponge, lariat RNA, or long non-coding RNA (lncRNA).

In an embodiment, the RNA molecule may be a self-amplifying RNA. The terms "self-amplifying RNA" and "RNA replicon" may be used interchangeably herein and refer to nucleic acid molecules capable of self-copying when introduced to the appropriate intracellular environment. Because they self-copy, RNA replicons may substantially amplify the production of an encoded protein, leading to sustained translation of a desired protein in vivo.

In an embodiment, the tail-tail RNA conjugate may comprise a self-amplifying, or "replicon", RNA molecules. Each of the self-amplifying RNA molecules may comprise operably connected elements as follows: i) a 5' cap, ii) a 5' untranslated region (UTR) which may or may not include an IRES sequence, iii) a protein coding or noncoding open reading frame (ORF), iv) an intervening non-coding sequence less than 1000 nt in length that serves as a promoter for RNA-dependent RNA transcription, iv) a second ORF, v) a 3' UTR, which may or may not include a poly-A tail, and vi) a terminal 3' nucleotide containing a chemically reactive moiety not present in natural replicon RNA resulting from transcription within a cell. The terminal 3' nucleotide containing a chemically reactive moiety may be also referred to herein as "3' RNA modification", or simply "3' modification."

In an embodiment, the RNA may be a messenger RNA (mRNA). mRNA may be any RNA that encodes at least one protein and may be translated to produce the encoded protein in vivo, in vitro or in situ. The person skilled in the art would appreciate that nucleic acid sequences set forth in the instant application may recite "T"s in DNA sequences but in RNA sequences (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

In an embodiment, the RNA molecule may comprise nucleobase chemical modifications. The RNA molecule may be partially modified. Alternatively, the RNA molecule may be completely modified.

In an embodiment, the precursor of the RNA molecule, or RNA precursor, may contain at least one nucleoside modification. In an embodiment, up to 100% of the nucleosides of the precursor RNA may be modified. The modification may comprise one or more nucleoside modification. Nucleoside modification may be a uridine modification or an adenosine modification. Some non-limiting examples of acceptable nucleoside base modification are N6-methyladenosine (m6A), pseudouridine (ψ), N1-methylpseudouridine (m1ψ), and 5-methoxyuridine (5moU). In an embodiment, the precursor RNA may be modified with methylpseudouridine (m1ψ).

In an embodiment, the terminal 3' nucleotide of the RNA molecules of the tail-tail RNA conjugate may comprise a chemically reactive moiety through which the RNA molecules are linked to each other. The chemically reactive moieties are described herein in methods of production the tail-tail RNA conjugates.

In an embodiment, the plurality of the RNA molecules may comprise two, three or four RNA molecules.

When the tail-tail RNA conjugate comprises two RNA molecules, these molecules may be linked via terminal 3' nucleotides comprising chemical moieties to create a 3'-to-3', or "tail-to-tail", RNA dimer. The RNA molecules may be linked to one another by a covalent bond to form an RNA dimer.

In an embodiment, the RNA molecules may comprise a linker that connects the terminal 3' nucleotide of each of the plurality of the RNA molecules to one another through the chemically reactive moiety. The linker may be a bifunctional, trifunctionally or tetrafunctionally reactive linker that connects respectively two, three or four RNA molecules. The linker may be a peptide, a nucleic acid molecule, a linear or branched polysaccharide chain, or a biocompatible polymer.

In an embodiment, the linker may be a peptide comprising one or more reactive side chains. The peptide may comprise a reactive N- or C-termini, or both. The peptide linker may be a branched peptide and comprise one, two, three, four or five branches. Each branch of the branch peptide may carry a terminal or side-chain reactive group.

The linker may be an RNA or DNA molecule comprising reactive nucleobases. The linker may be a DNA linker. The DNA linker may be a dA6 phospholinker. The sequence of the dA6 phospholinker may be p-(5')-dA-p-dA-p-dA-(3')-p-(3')-dA-p-dA-p-dA-(5')-p, where the lowercase "p" indicates a phosphate group. The sequence may consist of six deoxyadenosine (dA) residues in sequence connected by phosphodiester bonds, wherein the first three dA's may be in typical 5'-to-3' sequence, followed by an atypical phosphodiester bond that connects the 3' hydroxyls of the third and fourth dA residues. The fourth through sixth dA residues may be connected by typical phosphodiester bonds, but are oriented 3'-to-5' relative to the first three dA residues.

The linker may be an RNA linker. The RNA linker may be a A6 phospholinker. The sequence of the A6 phospholinker may be p-(5') A-p-A-p-A-(3')-p-(3')-A-p-A-p-A-(5')-p, where the lowercase "p" indicates a phosphate group. The sequence may consist of six adenosine (A) residues in sequence connected by phosphodiester bonds, wherein the first three A's may be in typical 5'-to-3' sequence, followed by an atypical phosphodiester bond that connects the 3' hydroxyls of the third and fourth A residues. The fourth through sixth A residues may be connected by typical phosphodiester bonds, but are oriented 3'-to-5' relative to the first three A residues.

The linker may a biocompatible polymer selected from the group consisting of: poly(ethylene glycol) (PEG), poly(glycerol) (PG), poly(N-vinylpyrrolidone) (PVP), and poly(N-(2-Hydroxypropyl) methacrylamide) (PHPMA). The biocompatible polymer linker component may have a molecular mass of 0.1-20.0 kDa, which is understood to be determined by the number of repeating units (represented by n in Drawings herein) comprising the polymer product. For example, the mass range of 0.1-20.0 represents n=~2-455 repeating oxyethylene groups.

In an embodiment, the tail-tail RNA conjugate may comprise two RNA linked via their final 3' nucleotides connected to a bifunctional linker to create a 3'-to-3', or "tail-to-tail", RNA dimer. The bifunctional linker may be a peptide comprising amino acids with reactive side-chains or N- or C-termini. The bifunctional linker may be a third nucleic acid molecule (RNA or DNA) comprising nucleotides with reactive nucleobases or 5'- or 3'-termini. The bifunctional linker may be a linear or branched polysaccharide chain with reactive moieties incorporated into the constituent sugar monomers. The bifunctional linker may comprise any one of the biocompatible polymers described herein. The bifunctional linker may possess a contour length of between 0.2 nm and 200 nm. The contour length herein refers to the maximum end-to-end distance of the extended polymer.

In an embodiment, the plurality of the RNA molecules may comprise three RNA molecules. Each one of the RNA molecules may be conjugated to another RNA molecule via final 3' nucleotides connected to a trifunctionally reactive linker. The plurality of the RNA molecule may comprise four RNA molecules, and each RNA molecule may be conjugated to another RNA molecule via final 3' nucleotides connected to a tetrafunctionally reactive linker. The linker may be any linker described herein.

In an embodiment, the RNA molecules linked together may be the same RNA molecule with identical sequence. The RNA molecules linked together may be different RNA molecules that differ by at least 1 nucleotide in sequence. For example, two RNA molecules linked together as a dimer by chemical reaction of the addressable chemical moieties to each other or to a bifunctional linker may be different RNA molecules that are the same length (number of nucleotides) but that differ by at least 1 nucleotide in sequence. The RNA molecules linked together may be different RNA molecules that differ in length (number of nucleotides) and in sequence.

In an embodiment, a nucleic acid comprising a DNA sequence encoding an RNA molecule is provided. The nucleic acid may be, for example, a DNA plasmid or a fragment of a linearized DNA plasmid. The nucleic acid may further comprise a promoter, such as a T7 promoter, operably linked to the 5'-end of the DNA sequence. The nucleic acid may be used for the production of an RNA molecules of the application using a method known in the art in view of the present disclosure. For example, a synthetic RNA molecule may be obtained by in vivo or in vitro transcription of the nucleic acid.

In an embodiment, the DNA sequence may be a DNA plasmid. The plasmid may be a common cloning plasmid such as one derived from pUC19, pGEM-T, pET, pBluescript, pBAD, pETite, or pDEST vectors. In an embodiment, the plasmid may be derived from a common mammalian expression vector such as pCMV, pEF1alpha, pAdenoV5, pAAV, pMAX, pcDNA3.1, or pGL4.

Methods of Production

An embodiment provides a method for preparing a plurality of the tail-conjugated RNA molecules linked to one another by chemical modification. The method may comprise providing two or more linear RNAs. The linear RNA may be any RNA molecule comprising operably connected elements as described herein.

The method may comprise modifying the linear RNA molecule by incorporating the terminal 3' nucleotide into the sequence of the linear RNA by an RNA polymerase, DNA polymerase, RNA ligase, DNA ligase, terminal nucleotidyl transferase, poly-A polymerase, nuclear or cytosolic tRNA-modifying enzyme, mitochondrial tRNA-modifying enzyme, or ribozyme.

In an embodiment of the method, the terminal 3' nucleotide may be incorporated into the linear RNA sequence as a part of a short terminal RNA oligonucleotide of less than 30 nucleotides in length. The short terminal RNA oligonucleotide may be added to the 3' end of the RNA molecule by an RNA polymerase, DNA polymerase, RNA ligase, DNA ligase, terminal nucleotidyl transferase, poly-A polymerase, nuclear or cytosolic tRNA-modifying enzyme, mitochondrial tRNA-modifying enzyme, or ribozyme.

In an embodiment of the method, the terminal 3' nucleotide reacted to be incorporated into the linear RNA sequence may be a locked or "bridged" nucleotide (LNA, alternatively "BNA"), 2' O-methylated, or phosphorothioated. A variety of chemical moieties may take the place of the 3' nucleotide. A ribonucleotide or deoxyribonucleotide may be present at the 3' terminus of the RNA sequence. The nucleotide or organic substituent may be, but is not limited to, a 2-Aminopurine, 2-MethoxyEthoxy A, 2-MethoxyEthoxy G, 2-MethoxyEthoxy MeC, 2-MethoxyEthoxy T, 2, 6-Diaminopurine, 2'-Fluoro A, 2'-Fluoro C, 2'-Fluoro G, 2'-Fluoro U, 5-Me dC, 5-Nitroindole, 5-Octadiynyl dU, 6-FAM™, 6-FAM™ (NHS Ester), ALEXA FLUOR® 488 (NHS Ester) (v3), ALEXA FLUOR® 532 (NHS Ester) (v3), ALEXA FLUOR® 546 (NHS Ester) (v3), ALEXA FLUOR® 594 (NHS Ester) (v3), ALEXA FLUOR® 647 (NHS Ester) (v3), ALEXA FLUOR® 750 (NHS Ester) (v3), Amino Modifier, UNI-LINK™ Amino Modifier, Amino Modifier C6 dT, ATTO™ 488 (NHS Ester), ATTO™ 532 (NHS Ester), ATTO™ 550 (NHS Ester), ATTO™ 565 (NHS Ester), ATTO™ 590 (NHS Ester), ATTO™ 633 (NHS Ester), ATTO™ 647N (NHS Ester), ATTO™ Rho101 (NHS Ester), Azide (via NHS Ester coupling), Biotin, Biotin dT, Biotin-TEG, BLACK HOLE QUENCHER® 1, 5-Bromo dU, C3 Spacer, Cholesterol-TEG, CY3™, CY5™, Dabcyl, deoxyInosine, deoxyUridine, Desthiobiotin-TEG, Dideoxy-C, Digoxigenin (NHS Ester), Dithiol, dSpacer, Fluorescein dT, Hexanediol, Inverted dT, IOWA BLACK® FQ, iso-C, iso-G, iso-dC, iso-dG, IOWA BLACK® RQ-Sp, JOE (NHS Ester), LIGHTCYCLER® 640 (NHS Ester) (v3), MAX (NHS Ester), Phosphorylation, RHODAMINE GREEN™-X (NHS Ester) (v3), RHODAMINE RED™-X (NHS Ester) (v3), ROX™ (NHS Ester) (v3), PC Spacer, Spacer 18, Spacer 9, SUPER G®, SUPER T®, TAMRA (via NHS Ester coupling), TAMRA (via azide coupling), TEX 615, TEXAS RED®-X (NHS Ester) (v3), Thiol Modifier C3 S-S, TYE™ 563, halogenated uridine, halogenated pseudouridine, halogenated adenosine, halogenated cytidine, halogenated thymidine, halogenated guanosine, the cordycepin derivative 3'-dATP, Cytidine-5'/3'-phosphate, CpG, pCp-Amine, vinyl-U, vinyl-A, vinyl-C, vinyl-G, vinyl-T, or any dideoxynucleotide.

In an embodiment of the method, the terminal 3' nucleotide reacted to be incorporated into the linear RNA sequence may possess a chemically reactive moiety that is specifically a bio-orthogonal click reaction handle, such as an azide or alkyne. The nucleotide may be added as a part of a short RNA oligonucleotide reacted to the 3' end of the RNA molecule. The terminal 3' nucleotide or nucleotides may be, but are not limited to, 5-Azidomethyl-UTP, 5-Azido-C3-UTP, 5-Azido-PEG4-UTP, 5-Ethynyl-UTP, DBCO-PEG4-UTP,3'-Azido-3'-dUTP, 3'-Azido-2',3'-ddUTP, Azide-PEG4-aminoallyl-dUTP, 3'-(O-Propargyl)-UTP, 5-Ethynyl-UTP (5-EUTP), 5-Ethynyl-dUTP (5-EdUTP), 5-DBCO-PEG4-UTP, 5-DBCO-PEG4-dUTP 5-Vinyl-UTP, 5-Vinyl-dUTP, 5-TCO-PEG4-dUTP, 8-Azido-AMP, 8-Azido-ADP, 8-Azido-ATP, 2'-Azido-2'-dATP, 3'-Azido-2',3'-ddATP, 3'-Azido-3'-dATP, N6-Azidohexyl-3'-dATP, N6-(6-Azido) hexyl-dATP, N6-(6-Azido)hexyl-3'-dATP, 3'-(O-Propargyl)-ATP, 2-Ethynyl-ATP (2-EATP), N6-Propargyl-ATP (N6pATP), 3'-Azido-3'-dGTP, 3'-Azido-2',3'-ddGTP, 3'-(O-Propargyl)-GTP, 5-Azido-PEG4-CTP, 5-Azido-PEG4-dCTP, 3'-Azido-3'-dCTP, 3'-(O-Propargyl)-CTP, 5-DBCO-PEG4-CTP5-DBCO-PEG4-dCTP, AzTTP, pCp-Azide, pCp-Alkyne, or 5-DBCO-PEG4-dCpG.

In an embodiment, the method may comprise linking together two RNA molecules carrying 3' modifications by chemical reaction of the chemically reactive moieties to create a 3'-to-3', or "tail-to-tail", linked RNA dimer.

In an embodiment, the method may comprise linking together two RNA molecules carrying 3' modifications by chemical reaction of the chemically reactive moieties to an intervening bifunctional linker to create a 3'-to-3', or "tail-to-tail", linked RNA dimer.

In an embodiment, the method may comprise linking together three RNA molecules carrying 3' modifications by chemical reaction of the of the chemically moieties to a trifunctionally reactive linker to create trimeric 3'-to-3', or "tail-to-tail", linked RNAs.

In an embodiment, the method may comprise linking together four RNA molecules carrying 3' modifications by chemical reaction of the of the chemically reactive moieties to a tetrafunctionally reactive linker to create tetrameric 3'-to-3', or "tail-to-tail", linked RNAs.

In an embodiment of the method, the chemical reaction that couples the 3' chemically reactive moieties to each other or to an intervening linker may be, but is not limited to, copper(I)-catalyzed azide-alkyne cycloaddition (CuAAC), strain-promoted azide-alkyne cycloaddition (SPAAC), strain-promoted alkyne-nitrone cycloaddition (SPANC), alkene and azide [3+2] cycloaddition, alkene and tetrazine inverse electron-demand Diels-Alder reaction (IEDDA), alkene and tetrazole photoclick reaction, cross coupling like Pd-catalyzed (Suzuki-Miyaura, Sonogashira, and Stille-Migita) coupling, oxidative Heck reaction, or amine coupling.

In another embodiment of the method, two RNA molecules carrying identical 3' reactive groups may be linked via an intervening bifunctional linker that reacts at its two ends to that reactive group. The two RNA molecules may be mixed in a 1:1 molar ratio in the presence of linker such that the molar ratio of total RNA reactive 3' ends to bifunctional linker may be 2:1 or more, resulting in efficient generation of RNA dimers. The RNA molecules may be identical or different, and only the 3' reactive group may need to be the same in this method.

In a further embodiment of the method, 3 or more linked RNA molecules as described above may be a combination of different RNAs linked by the same chemical mechanism to a trifunctional or tetrafunctional linker to produce a heterotrimer or heterotetramer. The desired final product may comprise a specific ratio of the different RNAs, which may be determined by the stoichiometry of the reagent RNAs reacted to the polyfunctional linker. The defined reagent ratio may result in a desirable ratio of linked RNAs. In an embodiment, the molar ratio of three different RNA molecules may be 1:1:1 to achieve RNA conjugates that are predominantly heterotrimers each carrying all three of the different RNAs. In an embodiment, two RNAs may be conjugated to generate a heterotrimer by reacting them in a 2:1 molar ratio to create heterotrimers predominantly carrying two copies of one RNA and one copy of the other. The desired product may or may not be further purified by Size Exclusion Chromatography (SEC) or similar method to isolate the desired product species. The product may be defined as a "heterofunctional RNA multimer".

Expression in Host Cells

In an embodiment, an expression system for expression of the tail-tail RNA conjugate is provided. The expression system may comprise any one of the synthetic tail-tail RNA conjugates described herein and a host cell or cells.

The host cells may be, but is not limited to, hamster ovary (CHO) cells, tumor cell lines, BHK cells, human cell lines, for example, HEK293 cells, PER.C6 cells. The host cells may be yeast, fungi, insect cells, animal or plant cells. Untransformed primary normal cells from humans or any mammalian species may be used, such as fibroblasts, stem cells, or cells of lymphoid or myeloid lineage.

In an embodiment, the production of one or more proteins in a host cell may comprise the introduction of the tail-tail RNA conjugate comprising RNA regions encoding the one or more proteins to be expressed the host cell, culturing the host cell under conditions suitable for expression of the nucleic acid molecules and allowing expression of the one or more proteins in the host cell.

For expression in the host cell, a synthetic tail-tail RNA conjugate comprising RNA regions encoding the one or more proteins may be included in an expression cassette that comprises regulatory sequences required for or promoting expression of the nucleic acid sequences. The regulatory sequences may include promoter, enhancer, promoter, and/or polyadenylation signal, and the like. The various promoters known in the art may be used for expressing nucleic acids disclosed herein in host cells. The promoters may be constitutive or inducible promoters. The promoters may be derived from prokaryotic or eukaryotic organisms, or may be designed artificially. The host cells may be cultured in suitable culture media commercially available for culturing cells for expressing the one or more proteins.

An embodiment provides a method of expressing one or more proteins in a cell. The method may comprise transfecting the tail-modified RNAs into the cell. In an embodiment, the method may comprise transfecting using lipofection or electroporation. In another embodiment, the method may comprise transfecting the tail-modified RNA into a cell using a nanocarrier comprising a lipid, a polymer, a dendrimer, or a combination of the same.

Method of Producing at Least One Heterologous Protein

In some embodiments, the two-or-more linked RNA molecules as described above may be used to drive expression of a protein encoded in their open reading frame sequences in a cell. The initiation of protein translation in the cell due to the presence of the 5' cap structures on the mRNAs or IRES elements in the 5' regions of the nucleic acid molecules. The conjugated RNAs may be mRNAs or saRNAs, or a combination thereof, encoding for either the same or different proteins. The proteins encoded may be of eukaryotic or prokaryotic origin. In an embodiment, the protein coding region may encode an antibody. The antibody may be encoded such that the heavy chain moiety is encoded on the first mRNA, and the light chain moiety is encoded on a second mRNA conjugated to the first as described above, to promote equimolar expression of the two chains which is necessary for efficient antibody expression. In an embodiment, the antibody encoded may be an anti-HIV or other antiviral antibody. In another embodiment, the antibody may be a bispecific antibody. The bispecific antibody may, for example, be specific for CD19 and CD22, or for CD3 and CLDN6. In an embodiment, the conjugated mRNAs may encode and express a protein that ameliorates a disease state. Examples of such therapeutic proteins include hFIX, SP-B, VEGF, human methylmalonyl-CoA mutase (hMUT), CFTR, cancer-associated self-antigens or neoantigens, and additional gene editing components such as Cpfl, CRISPR-Cas9 systems, zinc finger nucleases (ZFNs), and transcription activator-like effector nucleases (TALENs). In one embodiment, the RNA open reading frames may encode a reporter gene to enable detection of the nucleic acid. Reporter genes may include secreted embryonic alkaline phosphatase (SEAP), *Gaussia* luciferase (Gluc), Firefly luciferase (Fluc), enhanced green fluorescent protein (eGFP), green fluorescent protein (GFP), and human erythropoietin (hEPO).

In some embodiments, the two-or-more linked RNA molecules as described above may be delivered in combination with another nucleic acid or protein that serves to enhance the function encoded in one or more of the tail-linked RNA molecules.

For example, the RNA conjugates may encode a physiological signaling protein that increases or decreases the activity of a host organism's immune system. The proteins may comprise a pattern recognition receptor or effector protein that stimulates an innate immune response. The encoded protein may be an extracellular signaling molecule such as a cytokine, membrane surface receptor, membrane channel, or integrin or other glycoprotein affecting immune cell recognition. The immunogenic proteins may comprise an intracellular signaling protein such as STING protein. The stimulator of interferon genes (STING) plays a central role in innate immunity during infection and cancer. STING is endogenously activated by 2',3'-cyclic-GMP-AMP (cGAMP), a cyclic dinucleotide synthesized by cGAMP synthase (cGAS) in response to cytosolic DNA as a danger signal. Activation of STING mediates a multifaceted type I interferon (IFN-I) response that promotes the maturation and migration of dendritic cells, and primes cytotoxic T lymphocytes and nature killer cells for spontaneous immune responses. The signaling protein may be encoded on a first RNA that is conjugated to a second RNA that encodes a pathogen- or host-derived protein, thus modifying signaling activities within the same cell where the pathogen- or host-derived protein is translated. For example, mRNA encoding an influenza antigen such as hemagglutinin (HA) may be conjugated to an mRNA encoding an immunogenic cytokine such as RANTES to drive greater innate immune responses against the influenza virus.

Compositions

In an embodiment, the tail-tail RNA conjugates or proteins described herein may be administered in a composition.

In an embodiment, the composition may comprise the tail-tail RNA conjugates for expressing a target-specific antigen. The target-specific antigen may be a tumor antigen. The tumor antigen may be a neoantigen arising from mutations in the genome of the cell. Cancer-specific antigen may be derived from either one of: total mRNA isolated from target cell(s), one or more specific target mRNA molecules, protein lysates of target cell(s), specific proteins from target cell(s), or a synthetic target-specific peptide or protein and synthetic mRNA or DNA encoding a target-specific antigen or its derived peptides. Non-limiting examples may be one or more of the following cancer or tumor-specific antigens: WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase3 (PR1), Bcr-abl, Tyrosinase, Survivin, PSA, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic Acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-beta, MAD-CT-2, or Fos-related antigen 1.

In an embodiment, the composition may be a treatment for cancer. The treatment may comprise any one of tail-tail RNA conjugates comprising heterologous proteins described herein that express factors that inhibit or otherwise reduce growth or proliferation of tumor cells in the body of a human or animal.

The composition may further comprise a tail-tail RNA conjugate comprising mRNAs encoding an antibody. The composition may comprise a dimer comprise mRNAs encoding the heavy and light chains of trastuzumab antibody. The dimer may comprise a nucleic acid sequence encoding a heavy chain trastuzumab antibody and having a sequence with at least 70, 72, 75, 80, 85, 90, 91, 92, 93, 94, 95, 96, 97, 98, 99, or 100% identity to the sequence as set forth in SEQ ID NO: 19 and a nucleic acid sequence encoding the light chain of trastuzumab antibody and having a sequence with at least 70, 72, 75, 80, 85, 90, 91, 92, 93, 94, 95, 96, 97, 98, 99, or 100% identity to the sequence as set forth in SEQ ID NO: 20.

In an embodiment, the composition may comprise RNAs encoding one or more pathogen- or disease-derived protein antigen. As used herein, the term "antigenic protein" refers to a protein comprising one or more antigenic determinants that triggers an immune response. The immune response may involve either antibody production, or the activation of specific immunologically active cells, or both. The antigenic protein may be a structural or signaling component of a pathogen, or a cancer cell. The antigenic protein may be synthesized, produced recombinantly in a host, or may be derived from a biological sample, including but not limited to a tissue sample, cell, or a biological fluid. The pathogen from which the antigen is derived may be a virus of from the family of Adenoviridae, Papovaviridae, Parvoviridae, Herpesviridae, Poxviridae, Anelloviridae, Pleolipoviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae, Retroviridae, Caulimoviridae, or Hepadnaviridae. For example, the viral pathogen may be adenovirus, rhinovirus, rotavirus, West Nile virus, Zika virus, herpes, filovirus, or coronavirus (CoV). The coronavirus may be one of MERS CoV, SARS-CoV, and SARS-CoV-2. The antigenic protein may be, but is not limited to, a parasite antigenic protein, bacterial antigenic protein, tumor antigenic protein, environmental antigenic protein, therapeutic antigenic protein, or an allergen. The antigenic protein may be a protein comprising one or more antigenic determinants of the viral pathogen described herein. Such composition may be used to induce or detect immune responses against the antigen, such as humoral or cellular immune responses directed against the pathogen or disease cell of interest.

In an embodiment, the composition may be a vaccine. The vaccine may comprise any one of tail-tail RNA conjugates comprising coding sequences for antigenic proteins described herein. The term "vaccine" refers to an agent or composition containing an active component effective to induce a certain degree of immunity in a subject against a certain pathogen or disease, which will result in at least a decrease of the severity, duration, other manifestation, or elimination of symptoms associated with infection by the pathogen or the disease.

In an embodiment, the vaccine may comprise an Influenza strain PR8 HA mRNA. The vaccine may further comprise RANTES mRNA. The vaccine may comprise a dimer comprising an Influenza strain PR8 HA mRNA and RANTES mRNA. The dimer may comprise a nucleic acid sequence encoding Influenza strain PR8 HA and having a sequence with at least 70, 72, 75, 80, 85, 90, 91, 92, 93, 94, 95, 96, 97, 98, 99, or 100% identity to the sequence as set forth in SEQ ID NO: 5 and a nucleic acid sequence encoding the RANTES protein and having a sequence with at least 70, 72, 75, 80, 85, 90, 91, 92, 93, 94, 95, 96, 97, 98, 99, or 100% identity to the sequence as set forth in SEQ ID NO: 6. Such vaccine may be used to induce immune responses against Influenza viruses.

In an embodiment, the tail-tail RNA conjugates disclosed in any one of the embodiments herein may be encapsulated in a carrier system for in vivo administration. The carrier may be, but is not limited to, lipid an anionic liposome, a cationic liposome, a dendrimer, lipid nanoparticle, lipoplex, emulsion, polymeric nanoparticle, or a hybrid composition of the same. The RNA conjugates encapsulated in the carrier system may be administered to a human or animal subject by parenteral administration, such as intradermal, intramuscular, subcutaneous, transcutaneous, or mucosal administration, e.g., intranasal, oral, and the like. In one embodiment, a composition may be administered by intramuscular injection.

The term "anionic liposomes" refers to liposomes that include lipids comprising an anionic group. Anionic liposomes may be formed by anionic phospholipids. The term "cationic liposomes" refers to liposomes that are made in whole or part from positively charged lipids, or more specifically a lipid that comprises both a cationic group and a lipophilic portion. The positively charged moieties of cationic lipids used in cationic liposomes provide advantageous structural features. For instance, the lipophilic portion of the cationic lipid is hydrophobic and thus may direct itself away from the aqueous interior of the liposome and associate with other nonpolar and hydrophobic species, or conversely, the cationic moiety may associate with polar molecules and species with which it can complex in the aqueous interior of the cationic liposome. The positively charged liposomes may interact with the negatively charged nucleic acid molecules to form a stable complex.

Liposomes may include zwitterionic lipids. As used herein the term "zwitterionic" refers to a molecule that contains both positive and negative charges, but have a net neutral charge.

Liposomes may be formed from a single lipid or from a mixture of lipids. The hydrophilic portion of a lipid can be PEGylated, i.e., modified by covalent attachment of a polyethylene glycol to increase stability and prevent nonspecific adsorption of the liposomes (Heyes et al. (2005) J Controlled Release 107:276-87, which is incorporated herein by reference as if fully set forth).

The term "dendrimer" refers to a highly branched macromolecule with a spherical shape. The surface of the dendrimer molecule may be modified in many ways, and many of the properties of the resulting construct may be determined by its surface. The dendrimers may be modified to have a positive surface charge, i.e., to be cationic dendrimers. The cationic dendrimers may form temporary association with the nucleic acids. Upon reaching its destination the dendrimer-nucleic acid complex may be then taken into the cell via endocytosis.

An exemplary size for a single dendrimer-nucleic acid complex, also referred to herein as modified dendrimer nanoparticles (MDNPs), may be in the range of 30 nm to 1,000 nm in the longest dimension. MDNPs may have an average size from 30 nm to 450 nm, inclusive, from 50 nm to 300 nm, inclusive, or more from 60 nm to 250 nm, inclusive. MDNPS may be alkyl-modified dendrimer nanoparticles. Nanoparticle size may be influenced by the length of the alkyl chain that substitutes the core dendrimer. Methods of making and formulating modified dendrimer nanoparticles are described in WO2021207020, published Oct. 14, 2021; US 20210330600, published Oct. 28, 2021; and US 20210338789, published Nov. 4, 2021; all of which are incorporated herein by reference as if fully set forth.

In an embodiment, the composition may further comprise one or more adjuvants. The term "adjuvant" refers to one or more substances that cause stimulation of the immune system. An adjuvant may be used to enhance an immune response to the heterologous proteins used for immunizing a subject against a disease. The one or more adjuvants may include aluminum, e.g., as aluminum hydroxide and/or aluminum phosphate; oil-emulsion compositions or oil-in-water compositions, for example, squalene-water emulsions, such as MF59; saponin formulations, for example, QS21 and Immunostimulating Complexes (ISCOMS); bacterial or microbial derivatives, for example, monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, nucleic acids and other TLR agonists, for example poly(I:C); and the like; eukaryotic proteins, e.g., antibodies or fragments thereof, and ligands to receptors, which stimulate immune response upon interaction with recipient cells.

In an embodiment, the composition described herein may be utilized without adjuvants.

In an embodiment, the composition may be administered in a pharmaceutically acceptable carrier or excipient. As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zincstearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: sugars, such as lactose, glucose and sucrose; starches, such as corn starch and potato starch; cellulose, and its derivatives, such as sodium carboxymethyl cellulose, methylcellulose, ethyl cellulose, microcrystalline cellulose and cellulose acetate; powdered tragacanth; malt; gelatin; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol (PEG); esters, such as ethyl oleate and ethyllaurate; agar; buffering agents, such as magnesium hydroxide and aluminum hydroxide; alginic acid; pyrogen-free water; isotonic saline; (IS) Ringer's solution; ethyl alcohol; pH buffered solutions; polyesters, polycarbonates and/or polyanhydrides; bulking agents, such as polypeptides and amino acids, serum component, such as serum albumin, HDL and LDL; C2-C12 alchols, such as ethanol; and other non-toxic compatible substances employed in pharmaceutical formulations. Wetting agents, coloring agents, release agents, coating agents, sweetening agents, flavoring agents, perfuming agents, preservative and antioxidants may also be present in the formulation. The terms such as "excipient", "carrier", "pharmaceutically acceptable carrier" or the likes are used interchangeably herein. The pharmaceutically acceptable carriers and excipients are known in the art (Remington's Pharmaceutical Sciences, 18th edition, A. R. Gennaro, Ed., Mack Publishing Company, 1990; Pharmaceutical Formulation Development of Peptides and Proteins, S. Frokjaer and L. Hovgaard, Eds., Taylor & Francis, 2000; Handbook of Pharmaceutical Excipients, 3rd edition, A. Kibbe, Ed., Pharmaceutical Press, 2000). The synthetic tail-tail RNA conjugates described herein may be formulated and administered as a sterile and/or lyophilized solution. Sterile solutions may be prepared by sterile filtration or by any other known methods. The solutions may be then lyophilized or filled into pharmaceutical dosage containers. The pH of the solution generally may be in the range of pH 3.0 to 9.5, e.g., pH 5.0 to 7.5. In an embodiment, a stabilizing agent may be added, such as albumin or additional sugars (e.g., sucrose). In an embodiment, detergent may be added. In an embodiment, the nucleic acid mixtures comprising any of the tail-tail RNA conjugates described herein may be formulated into an injectable preparation.

An embodiment provides the use of a preparation of tail-tail RNA conjugates generated by the method disclosed herein in the manufacture of a vaccine capable of eliciting an immune response against Influenza viruses in a patient in need thereof.

In an embodiment, a method of inducing an immune response in a subject is provided. The method may comprise administering to the subject a therapeutically effective amount of a vaccine comprising any one of the synthetic tail-tail RNA conjugates described herein.

In an embodiment, a method for preventing and/or treating a subject against a disease or condition is provided. The method may comprise utilizing any one of compositions and vaccines described herein. The method may comprise administering to a subject in need thereof a therapeutically effective amount of a composition or vaccine comprising the synthetic tail-tail RNA conjugates described herein as described above. In connection with treating cancer, the "therapeutically effective amount" is that amount effective for preventing further development of a cancer or transformed growth, and even to effect regression of the cancer or solid tumor.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

Administration of the compositions or vaccines described herein may be performed using known routes of administration. The compositions or vaccines may be administered by using parenteral administration, such as intradermal, intramuscular, subcutaneous, transcutaneous, or mucosal administration, e.g., intranasal, oral, and the like. In one embodiment a composition may be administered by intramuscular injection. As used herein, the term "administer" refers to the placement of a composition into a subject by a method or route which results in at least partial localization of the composition at a desired site such that desired effect is produced. A compound or composition described herein may be administered by any appropriate route known in the art including, but not limited to, oral or parenteral routes, including intravenous, intramuscular, subcutaneous, transdermal, airway (aerosol), pulmonary, nasal, rectal, or topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, trans tracheal, subcutaneous, subcuticular, intraarticular, sub capsular, subarachnoid, intraspinal, intracerebro spinal, and intrastemal injection and infusion. In an embodiment, the compositions may be administered by intravenous infusion or injection.

Vaccines described herein may be administered by any known routes in order to induce an immune response to the antigen(s) in the vaccine.

In an embodiment, methods of administration or delivery may not be limited to the above described methods, and any means for intracellular delivery may be used.

A therapeutically effective amount refers to an amount of a protein, or nucleic acid molecule, which is effective for preventing, ameliorating and/or treating a disease or condition resulting from infection by a pathogen. Prevention encompasses inhibiting or reducing the spread of pathogen or inhibiting or reducing the onset, development, or progression of one or more of the symptoms associated with infection by pathogen. Amelioration, as used in herein, refer to the reduction of visible or perceptible disease symptoms, viremia, or any other measurable manifestation of the infection induced by pathogen.

In connection with treating cancer, the "therapeutically effective amount" is that amount effective for preventing further development of a disease, and even to effect regression of the disease.

Determination of a therapeutically effective amount is generally well within the capability of those skilled in the art. Generally, a therapeutically effective amount can vary with the subject's history, age, condition, sex, as well as the severity and type of the medical condition in the subject, and administration of other agents alleviate the disease or disorder to be treated.

Toxicity and therapeutic efficacy may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. As used herein, the term ED denotes effective dose and is used in connection with animal models. The term EC denotes effective concentration and is used in connection with in vitro models.

The data obtained from the cell culture assays and animal studies may be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose may be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage may be monitored by a suitable bioassay.

The dosage may be determined by a physician and adjusted, as necessary, to suit observed effects of the treatment. Generally, the compositions may be administered so that the active agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In an embodiment, the compositions may be administered at a dosage so that the active agent has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hours, 2 hours, 2.5 hours, 3 hours, 4 hours, 5 hours, 6 hours, 7 hours, 8 hours, 9 hours, 10 hours, 11 hours, 12 hours or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule may vary from once a week to daily depending on a number of clinical factors, such as the subject's sensitivity to the polypeptides. The desired dose may be administered every day or every third, fourth, fifth, or sixth day. The desired dose may be administered at one time or divided into subdoses, e.g., 2-4 subdoses and administered over a period of time, e.g., at appropriate intervals through the day or other appropriate schedule. Such sub-doses may be administered as unit dosage forms. In an embodiment, administration may be chronic, e.g., one or more doses daily over a period of weeks or months. Examples of dosing schedules may include administration daily, twice daily, three times daily or four or more times daily over a period of 1 week, 2 weeks, 3 weeks, 4 weeks, 1 month, 2 months, 3 months, 4 months, 5 months, or 6 months or more.

In an embodiment, a method of preparing a vaccine or a therapeutic composition against a disease or condition is provided. The method may comprise providing a vaccine or therapeutic composition described herein and formulating it into a pharmaceutically acceptable composition. The vaccine composition may comprise an effective amount of the heterologous immunogenic protein and/or a nucleic acid molecule encoding the protein, which results in an immune response against the disease.

In an embodiment, the disease may be caused by a viral pathogen. The pathogen may be a viral pathogen. The viral pathogen may be an Influenza virus, adenovirus, rhinovirus, rotavirus, West Nile virus, Zika virus, herpes, or coronavirus (CoV). The coronavirus may be one of MERS CoV, SARS-CoV and SARS-CoV-2 viruses.

The "vaccine" described herein may be provided as a pharmaceutical composition. The composition may include a pharmaceutically acceptable diluent, carrier or excipient. The composition may comprise further active ingredients. The administration may be provided at a single dose or in a prime-boost setting. The prime-boost setting may involve "priming" and "boosting" immunization regimes, in which the immune response induced by a prime vaccine may be boosted by a boost vaccine. For example, following priming (at least once) with any one of polynucleotides encoding a first heterologous protein, a boost vaccine comprising an effective amount of a second heterologous antigenic protein, or a subunit thereof, may be administered to boost the immune response in the primed host.

Compositions described herein may be administered to a subject, e.g., a human subject. The total dose of the heterologous immunogenic proteins in a composition for a single administration may, for instance, be about 0.01 µg to about 10 mg, e.g., 1 µg-1 mg, e.g., 10 µg-100 µg. Determining the recommended dose may be carried out by experimentation and is routine for those skilled in the art.

The terms "subject" and "individual" are used interchangeably herein, and mean a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In an embodiment, the subject may be a mammal, e.g., a primate, e.g., a human. The terms, "patient" and "subject" are used interchangeably herein. The terms, "patient" and "subject" are used interchangeably herein. Preferably, the subject is a mammal. The mammal may be a human, non-human primate, mouse, rat, dog, cat, horse, or cow, but are not limited to these examples.

The following list includes particular embodiments of the present invention. But the list is not limiting and does not exclude alternate embodiments, or embodiments otherwise described herein. Percent identity described in the following embodiments list refers to the identity of the recited sequence along the entire length of the reference sequence.

EMBODIMENTS

1. A tail-tail RNA conjugate comprising a plurality of RNA molecules, each of which comprises operably connected elements comprising: a 5' untranslated region (UTR), a coding or non-coding RNA region, a 3' UTR, and a terminal 3' nucleotide, wherein each RNA molecule is connected to one another through the terminal 3' nucleotide.

2. The tail-tail RNA conjugate of embodiment 1, wherein the operably connected elements further comprise a 5' cap.

3. The tail-tail RNA conjugate of one or both embodiments 1 and 2, wherein the coding RNA region comprises a protein coding open reading frame (ORF).

4. The tail-tail RNA conjugate of any one or more of embodiments 1-3, wherein the open reading frame (ORF) encodes a reporter protein.

5. The tail-tail RNA conjugate of one or more of embodiments 1-4, wherein the reporter protein is selected from the group consisting of: a secreted embryonic alkaline phosphatase (SEAP), *Gaussia* luciferase (Gluc), Firefly luciferase (Fluc), green fluorescent protein (GFP), enhanced green fluorescent protein (eGFP), and human erythropoietin (hEPO).

6. The tail-tail RNA conjugate of one or more of embodiments 1-5, wherein the coding RNA region comprises a nucleic acid sequence with at least 90% identity to the sequence selected from the group consisting of SEQ ID NOs: 1-4.

7. The tail-tail RNA conjugate of any one or more of embodiments 1-3 wherein the open reading frame (ORF) encodes a virus-derived protein, mammalian cell-derived regulator of immune, or signaling function.

8. The tail-tail RNA conjugate of any one or more of embodiments 1-3 and 7, wherein the virus-derived protein comprises an influenza strain PR8 hemagglutinin.

9. The tail-tail RNA conjugate of any one or more embodiments 1-3 and 7-8, wherein the coding RNA region comprises a nucleic acid sequence with at least 90% identity to the sequence of SEQ ID NO: 5.

10. The tail-tail RNA conjugate of any one or more embodiments 1-3 and 7-9, wherein the mammalian cell-derived regulator of immune, or signaling function comprises RANTES protein.

11. The tail-tail RNA conjugate of any one or more embodiments 1-3 and 7-10, wherein the coding RNA region comprises a nucleic acid sequence with at least 90% identity to the sequence of SEQ ID NO: 6.

12. The tail-tail RNA conjugate of any one or more of embodiments 1-3, wherein the open reading frame (ORF) encodes an antibody.

13. The tail-tail RNA conjugate of any one or more of embodiments 1-3, and 12, wherein the antibody comprises a heavy chain and/or light chain of trastuzumab.

14. The tail-tail RNA conjugate of any one or more of embodiments 1-3, and 12-13, wherein the coding RNA region comprises a nucleic acid sequence encoding the heavy chain of trastuzumab with at least 90% identity to the sequence of SEQ ID NO: 19.

15. The tail-tail RNA conjugate of any one or more of embodiments 1-3, and 12-14, wherein the coding RNA region comprises a nucleic acid sequence encoding the light chain of trastuzumab with at least 90% identity to the sequence of SEQ ID NO: 20.

16. The tail-tail RNA conjugate of any one or more embodiments 1-15 comprising the noncoding RNA region.

17. The tail-tail RNA conjugate of any one or more embodiments 1-16, wherein the 5' untranslated region (UTR) comprises an IRES sequence.

18. The tail-tail RNA conjugate of any one or more embodiments 1-17, wherein the 3' UTR comprises a poly-A tail.

19. The tail-tail RNA conjugate of any one or more embodiments 1-18, wherein the RNA molecule is selected from the group consisting of: an mRNA, shRNA, siRNA, miRNA, self-amplifying RNA (saRNA), miRNA sponge, lariat RNA, and long non-coding RNA (lncRNA) 20. The tail-tail RNA conjugate of any one or more embodiments 1-19, wherein the RNA molecule comprises a self-amplifying RNA.

21. The tail-tail RNA conjugate of any one or more embodiments 1-20, wherein the self-amplifying RNA further comprises at least one of an intervening non-coding sequence and a second ORF.

22. The tail-tail RNA conjugate of any one or more embodiments 1-21, wherein the intervening non-coding sequence comprises a promoter for RNA-dependent RNA transcription, and comprises a sequence of 1000 nt or less.

23. The tail-tail RNA conjugate of any one or more embodiments 1-22, wherein the terminal 3' nucleotide comprises a chemically reactive moiety.

24. The tail-tail RNA conjugate of any one or more embodiments 1-23, wherein the plurality of the RNA molecules comprises two, three or four RNA molecules.

25. The tail-tail RNA conjugate of any one or more embodiments 1-24, wherein the plurality of the RNA molecules comprises two RNA molecules.

26. The tail-tail RNA conjugate of any one or more embodiments 1-25, wherein each RNA molecule is linked to one another by a covalent bond to form an RNA dimer.

27. The tail-tail RNA conjugate of any one or more embodiments 1-25 further comprising a linker that connects the terminal 3' nucleotide of each of the plurality of the RNA molecules to one another through the chemically reactive moiety.

28. The tail-tail RNA conjugate of claim any one or more embodiments 1-25 and 27, wherein the linker is selected from the group consisting of: a bifunctional, trifunctionally or tetrafunctionally reactive linker.

29. The tail-tail RNA conjugate of any one or more embodiments 1-25 and 27-28, wherein the linker is selected from the group consisting of: a peptide, a nucleic acid molecule, a linear or branched polysaccharide chain, and a biocompatible polymer.

30. The tail-tail RNA conjugate of any one or more embodiments 1-25 and 27-29, wherein the linker is a peptide comprising one or more reactive side chains.

31. The tail-tail RNA conjugate of any one or more embodiments 1-25 and 27-30, wherein the linker is a peptide comprising a reactive N- or C-termini, or both.

32. The tail-tail RNA conjugate of any one or more embodiments 1-25 and 27-31, wherein the peptide linker is a branched peptide.

33. The tail-tail RNA conjugate of any one or more embodiments 1-25 and 27-32, wherein the branched peptide comprises one, two, three, four or five branches, and each branch carries a terminal or side-chain reactive group.

34. The tail-tail RNA conjugate of any one or more embodiments 1-25 and 27-29, wherein the linker is an RNA or DNA molecule comprising reactive nucleobases.

35. The tail-tail RNA conjugate of any one or more embodiments 1-25, 27-29 and 34, wherein the RNA molecule comprises an A6 phospholinker.

36. The tail-tail RNA conjugate of any one or more embodiments 1-25, 27-29 and 34, wherein the DNA molecule comprises a dA6 phospholinker.

37. The tail-tail RNA conjugate of any one or more embodiments 1-25 and 27-29, wherein the linker is a biocompatible polymer selected from the group consisting of: poly(ethylene glycol) (PEG), poly(glycerol) (PG), poly(N-vinylpyrrolidone) (PVP), and poly(N-(2-Hydroxypropyl) methacrylamide) (PHPMA).

38. The tail-tail RNA conjugate of any one or more embodiments 1-25 and 27-37, wherein the plurality of the RNA molecules comprises two RNA molecules, and each RNA molecule is conjugated to another RNA molecule through a bifunctional reactive linker.

39. The tail-tail RNA conjugate of any one or more embodiments 1-25, 27-38, wherein the length of the bifunctional linker is within a range from 0.2 nm to 200 nm.

40. The tail-tail RNA conjugate of any one or more embodiments 1-6, 16-19, 21-25, 27-28, 36 and 38, wherein one RNA molecule comprises a sequence with at least 90% identity to SEQ ID NO: 1, another RNA molecule comprises a sequence with at least 90% identity to SEQ ID NO: 2, and each RNA molecule is conjugated to another RNA molecule through a dA6 phospholinker.

41. The tail-tail RNA conjugate of any one or more embodiments 1-6, 16-19, 21-25, 27-28, 36 and 38, wherein one RNA molecule comprises a sequence with at least 90% identity to SEQ ID NO: 3, another RNA molecule comprises a sequence with at least 90% identity to SEQ ID NO: 4 and each RNA molecule is conjugated to another RNA molecule through a dA6 phospholinker.

42. The tail-tail RNA conjugate of any one or more embodiments 1-3, 7-11, 16-19, 21-25, 27-28, 36 and 38, wherein one RNA molecule comprises a sequence with at least 90% identity to SEQ ID NO: 5, another RNA molecule comprises a sequence with at least 90% identity to SEQ ID NO: 6, and each RNA molecule is conjugated to another RNA molecule through a dA6 phospholinker.

43. The tail-tail RNA conjugate of any one or more embodiments 1-3, 12-19, 21-25, 27-28, 36 and 38, wherein one RNA molecule comprises a sequence with at least 90% identity to SEQ ID NO: 19, another RNA molecule comprises a sequence with at least 90% identity to SEQ ID NO: 20, and each RNA molecule is conjugated to another RNA molecule through a dA6 phospholinker.

44. The tail-tail RNA conjugate of any one or more embodiments 1-24, 27-34, and 37, wherein the plurality of the RNA molecule comprises three RNA molecules, and each RNA molecule is conjugated to another RNA molecule through a trifunctionally reactive linker.

45. The tail-tail RNA conjugate of any one or more embodiments 1-24, 27-34, and 37, wherein the plurality of the RNA molecule comprises four RNA molecules, and each RNA molecule is conjugated to another RNA molecule through a tetrafunctionally reactive linker.

46. The tail-tail RNA conjugate of any one or more embodiments 1-45, wherein each of the RNA molecules comprises the identical sequence.

47. The tail-tail RNA conjugate of any one or more embodiments 1-46, wherein each of the RNA molecules comprises the sequence that differs from one another.

48. A method of preparing the tail-tail RNA conjugate of claim 1 comprising:
    providing two or more linear DNA plasmids;
    transcribing DNA plasmids to produce linear RNA sequences and
    linking terminal 3' nucleotides comprising chemically reactive moieties of the RNA sequences to produce a tail-tail RNA conjugate.

49. The method of embodiment 48 further comprising, prior to linking, incorporating each one of the 3' nucleotides into the linear RNA sequences by an enzyme selected from the group consisting of: an RNA polymerase, DNA polymerase, RNA ligase, DNA ligase, terminal nucleotidyl transferase, poly-A polymerase, nuclear or cytosolic tRNA-modifying enzyme, mitochondrial tRNA-modifying enzyme, and ribozyme.

50. The method of one or both embodiments 48 and 49, further comprising, prior to linking, incorporating into each one of the 3' nucleotides a chemically reactive moiety selected from the group consisting of: 5-Azidomethyl-UTP, 5-Azido-C3-UTP, 5-Azido-PEG4-UTP, 5-Ethynyl-UTP, DBCO-PEG4-UTP,3'-Azido-3'-dUTP, 3'-Azido-2',3'-ddUTP, Azide-PEG4-aminoallyl-dUTP, 3'-(O-Propargyl)-UTP, 5-Ethynyl-UTP (5-EUTP), 5-Ethynyl-dUTP (5-EdUTP), 5-DBCO-PEG4-UTP, 5-DBCO-PEG4-dUTP 5-Vinyl-UTP, 5-Vinyl-dUTP, 5-TCO-PEG4-dUTP, 8-Azido-AMP, 8-Azido-ADP, 8-Azido-ATP, 2'-Azido-2'-dATP, 3'-Azido-2',3'-ddATP, 3'-Azido-3'-dATP, N6-Azidohexyl-3'-dATP, N6-(6-Azido)hexyl-dATP, N6-(6-Azido)hexyl-3'-dATP, 3'-(O-Propargyl)-ATP, 2-Ethynyl-ATP (2-EATP), N6-Propargyl-ATP (N6pATP), 3'-Azido-3'-dGTP, 3'-Azido-2',3'-ddGTP, 3'-(O-Propargyl)-GTP, 5-Azido-PEG4-CTP, 5-Azido-PEG4-dCTP, 3'-Azido-3'-dCTP, 3'-(O-Propargyl)-CTP, 5-DBCO-PEG4-CTP5-DBCO-PEG4-dCTP, AzTTP, pCp-Azide, pCp-Alkyne, and 5-DBCO-PEG4-dCp.G.

51. The method of any one or more embodiments 48-50, wherein the length of each one of the 3' nucleotides is 30 nucleotides or less.

52. The method of any one or more embodiments 48-51, wherein each one of the 3' nucleotides is selected from the group consisting of: a locked (LNA) nucleotide, "bridged" (BNA) nucleotide, 2' O-methylated nucleotide, and phosphorothioated nucleotide.

53. The method of any one or more embodiments 48-52, wherein each one of the 3' nucleotides is replaced with a chemical moiety.

54. The method of any one or more embodiments 48-53, wherein the chemical moiety is selected from the group consisting of: a 2-Aminopurine, 2-MethoxyEthoxy A, 2-MethoxyEthoxy G, 2-MethoxyEthoxy MeC, 2-MethoxyEthoxy T, 2, 6-Diaminopurine, 2'-Fluoro A, 2'-Fluoro C, 2'-Fluoro G, 2'-Fluoro U, 5-Me dC, 5-Nitroindole, 5-Octadiynyl dU, 6-FAM™, 6-FAM™ (NHS Ester), ALEXA FLUOR® 488 (NHS Ester) (v3), ALEXA FLUOR® 532 (NHS Ester) (v3), ALEXA FLUOR® 546 (NHS Ester) (v3), ALEXA FLUOR® 594 (NHS Ester) (v3), ALEXA FLUOR® 647 (NHS Ester) (v3), ALEXA FLUOR 0 750 (NHS Ester) (v3), Amino Modifier, UNI-LINL™ Amino Modifier, Amino Modifier C6 dT, ATTO™ 488 (NHS Ester), ATTO™ 532 (NHS Ester), ATTO™ 550 (NHS Ester), ATTO™ 565 (NHS Ester), ATTO™ 590 (NHS Ester), ATTO™ 633 (NHS Ester), ATTO™ 647N (NHS Ester), ATTO™ Rho101 (NHS Ester), Azide (via NHS Ester coupling), Biotin, Biotin dT, Biotin-TEG, BLACK HOLE QUENCHER® 1, 5-Bromo dU, C3 Spacer, Cholesterol-TEG, CY3™, CY5™, Dabcyl, deoxyInosine, deoxyUridine, Desthiobiotin-TEG, Dideoxy-C, Digoxigenin (NHS Ester), Dithiol, dSpacer, Fluorescein dT, Hexanediol, Inverted dT, IOWA BLACK® FQ, iso-C, iso-G, iso-dC, iso-dG, IOWA BLACK® RQ-Sp, JOE (NHS Ester), LIGHT CYCLER® 640 (NHS Ester) (v3), MAX (NHS Ester), phosphate group, RHODAMINE GREEN™-X (NHS Ester) (v3), RHODAMINE RED™-X (NHS Ester) (v3), ROX™ (NHS Ester) (v3), PC Spacer, Spacer 18, Spacer 9, SUPER G®, SUPER T®, TAMRA (via NHS Ester coupling), TAMRA (via azide coupling), TEX 615, TEXAS RED®-X (NHS Ester) (v3), Thiol Modifier C3 S-S, TYE™ 563, halogenated uridine, halogenated pseudouridine, halogenated adenosine, halogenated cytidine, halogenated thymidine, halogenated guanosine, the cordycepin derivative 3'-dATP, Cytidine-5'/3'-phosphate, CpG, pCp-Amine, vinyl-U, vinyl-A, vinyl-C, vinyl-G, vinyl-T, and dideoxynucleotide.

54. The method of any one or more embodiments 48-53, wherein each one of the 3' nucleotides comprise a ribonucleotide or deoxyribonucleotide.

55. The method of any one or more embodiments 48-54, wherein each one of the 3' nucleotides comprise an azide or alkyne.

56. The method of any one or more embodiments 48-55, wherein each one of the 3' nucleotides is selected from the group consisting of: 5-Azidomethyl-UTP, 5-Azido-C3-UTP, 5-Azido-PEG4-UTP, 5-Ethynyl-UTP, DBCO-PEG4-UTP,3'-Azido-3'-dUTP, 3'-Azido-2',3'-ddUTP, Azide-PEG4-aminoallyl-dUTP, 3'-(O-Propargyl)-UTP, 5-Ethynyl-UTP (5-EUTP), 5-Ethynyl-dUTP (5-EdUTP), 5-DBCO-PEG4-UTP, 5-DBCO-PEG4-dUTP 5-Vinyl-UTP, 5-Vinyl-dUTP, 5-TCO-PEG4-dUTP, 8-Azido-AMP, 8-Azido-ADP, 8-Azido-ATP, 2'-Azido-2'-dATP, 3'-Azido-2',3'-ddATP, 3'-Azido-3'-dATP, N6-Azidohexyl-3'-dATP, N6-(6-Azido)hexyl-dATP, N6-(6-Azido)hexyl-3'-dATP, 3'-(O-Propargyl)-ATP, 2-Ethynyl-ATP (2-EATP), N6-Propargyl-ATP (N6pATP), 3'-Azido-3'-dGTP, 3'-Azido-2',3'-ddGTP, 3'40-Propargyl)-GTP, 5-Azido-PEG4-CTP, 5-Azido-PEG4-dCTP, 3'-Azido-3'-dCTP, 3'-(O-Propargyl)-CTP, 5-DBCO-PEG4-CTP5-DBCO-PEG4-dCTP, AzTTP, pCp-Azide, pCp-Alkyne, and 5-DBCO-PEG4-dCpG.

57. The method of any one or more embodiments 48-56, wherein linking comprises reacting the chemically reactive moieties of the 3' nucleotides of two RNA molecules to create an RNA dimer.

58. The method of any one or more embodiments 48-57, wherein linking comprises conjugating the chemically reactive moieties of the 3' nucleotides of two RNA molecules to a bifunctional linker.

59. The method of any one or more embodiments 48-56, wherein linking comprises conjugating the chemically reactive moieties of the 3' nucleotides of three RNA molecules to a trifunctionally reactive linker.

60. The method of claim any one or more embodiments 48-56 wherein linking comprises conjugating the chemically reactive moieties of the 3' nucleotides of four RNA molecules to a tetrafunctionally reactive linker.

61. The method of any one or more embodiments 48-60, wherein linking comprises the chemical reaction that couples the chemically reactive moieties to each other or to an intervening linker is selected from the group consisting of: copper(I)-catalyzed azide-alkyne cycloaddition (CuAAC), strain-promoted azide-alkyne cycloaddition (SPAAC), strain-promoted alkyne-nitrone cycloaddition (SPANC), alkene and azide [3+2] cycloaddition, alkene and tetrazine inverse electron-demand Diels-Alder reaction (IEDDA), alkene and tetrazole photoclick reaction, cross coupling like Pd-catalyzed (Suzuki-Miyaura, Sonogashira, and Stille-Migita) coupling, oxidative Heck reaction, and amine coupling.

62. A method of producing a polypeptide comprising expressing the tail-tail RNA conjugate of any one or more embodiments 1-47 in a host cell.

63. A method of preventing, inhibiting, or treating the symptoms of a disease or condition in a subject comprising: providing a tail-tail RNA conjugate comprising a plurality of RNA molecules, each of which comprises operably connected elements comprising: a 5' untranslated region (UTR), a coding or non-coding RNA region, a 3' UTR, and a terminal 3' nucleotide, wherein each RNA molecule is connected to one another through the terminal 3' nucleotide; and administering a therapeutically effective amount of the tail-tail RNA conjugate to a subject. 64. The method of embodiment 63, wherein the open reading frame (ORF) encodes a virus-derived protein, mammalian cell-derived regulator of immune, or signaling function.

65. The method of one or both embodiments 63 and 64, wherein the virus-derived protein comprises an influenza strain PR8 hemagglutinin.

66. The method of any one or more embodiments 63-65, wherein the coding RNA region comprises a nucleic acid sequence with at least 90% identity to the sequence of SEQ ID NO: 5.

67. The method of any one or more embodiments 63-65, wherein the mammalian cell-derived regulator of immune, or signaling function comprises RANTES protein.

68. The method of any one or more embodiments 63-67, wherein the coding RNA region comprises a nucleic acid sequence with at least 90% identity to the sequence of SEQ ID NO: 6.

69. The method of any one or more embodiments 63-68, wherein one RNA molecule comprises a sequence with at least 90% identity to SEQ ID NO: 5, another RNA molecule comprises a sequence with at least 90% identity to SEQ ID NO: 6, and each RNA molecule is conjugated to another RNA molecule through a dA6 phospholinker.

70. The method of embodiment 63, wherein the open reading frame (ORF) encodes an antibody. 71. The method of any one or both of embodiments 63 and 70, wherein the antibody comprises a heavy chain and/or light chain of trastuzumab.

72. The method of of any one or more of embodiments 63 and 70-71, wherein the coding RNA region comprises a nucleic acid sequence encoding the heavy chain of trastuzumab with at least 90% identity to the sequence of SEQ ID NO: 19.

73. The of any one or more of embodiments 63, and 70-72, wherein the coding RNA region comprises a nucleic acid sequence encoding the light chain of trastuzumab with at least 90% identity to the sequence of SEQ ID NO: 20.

74. The method of any one or more embodiments 63 and 70-73, wherein one RNA molecule comprises a sequence with at least 90% identity to SEQ ID NO: 19, another RNA molecule comprises a sequence with at least 90% identity to SEQ ID NO: 20, and each RNA molecule is conjugated to another RNA molecule through a dA6 phospholinker.

75. The method of any one or more embodiments 63-74, wherein the step of administering results in preventing, treating, reducing the severity or slowing the progression of the disease in the subject.

76. The method of any one or more embodiments 63-75, wherein the subject is a mammal. 77. The method of any one or more embodiments 63-76, wherein the mammal is a human. 78. A pharmaceutically acceptable composition comprising the tail-tail RNA conjugate of any one or more of embodiments 1-47 and a pharmaceutically acceptable carrier or excipient.

Further embodiments herein may be formed by supplementing an embodiment with one or more elements from any one or more other embodiments herein, and/or substituting one or more elements from one embodiment with one or more elements from one or more other embodiments.

EXAMPLES

The following non-limiting examples are provided to illustrate particular embodiments. The embodiments throughout may be supplemented with one or more details from one or more examples below, and/or one or more elements from an embodiment

Example 1. Design of RNAs Molecules Connected "Tail-to-Tail"

There is a need to develop RNAs with protected 3' ends that remain capable of binding a eukaryotic ribosome by classical eIF4F-mediated translation initiation in eukaryotic cells, thereby enabling production of large amounts of desired polypeptides as an experimental, vaccine, or therapeutic tool. Therefore, this disclosure, provides two or more RNA molecules connected "tail-to-tail" or 3'-to-3' by using novel biorthogonal chemistry approaches. Among other benefits, the product RNA will be more stable since they will escape 3-5' exonuclease activity owing to the absence of free RNA 3' ends.

FIGS. 1A-1D are schematic diagrams showing methods of creation of tail-tail RNA conjugates according to embodiments disclosed herein.

FIG. 1A is a schematic diagram showing an example of a conventional linear mRNA molecule. In the figure, the 5' cap, 5' untranslated region (UTR), protein-coding open reading frame (ORF), 3' UTR, and poly-A tail are labeled.

FIG. 1B is a schematic diagram showing an example of two linear mRNA molecules comprising 3' reactive moieties, which is present on the terminal 3' nucleotide. mRNA 1 and mRNA 2 may be different or identical, and the reactive moieties 1 and 2 may be reactive with each other, or alternatively with a third reactive moiety.

Figure 10:
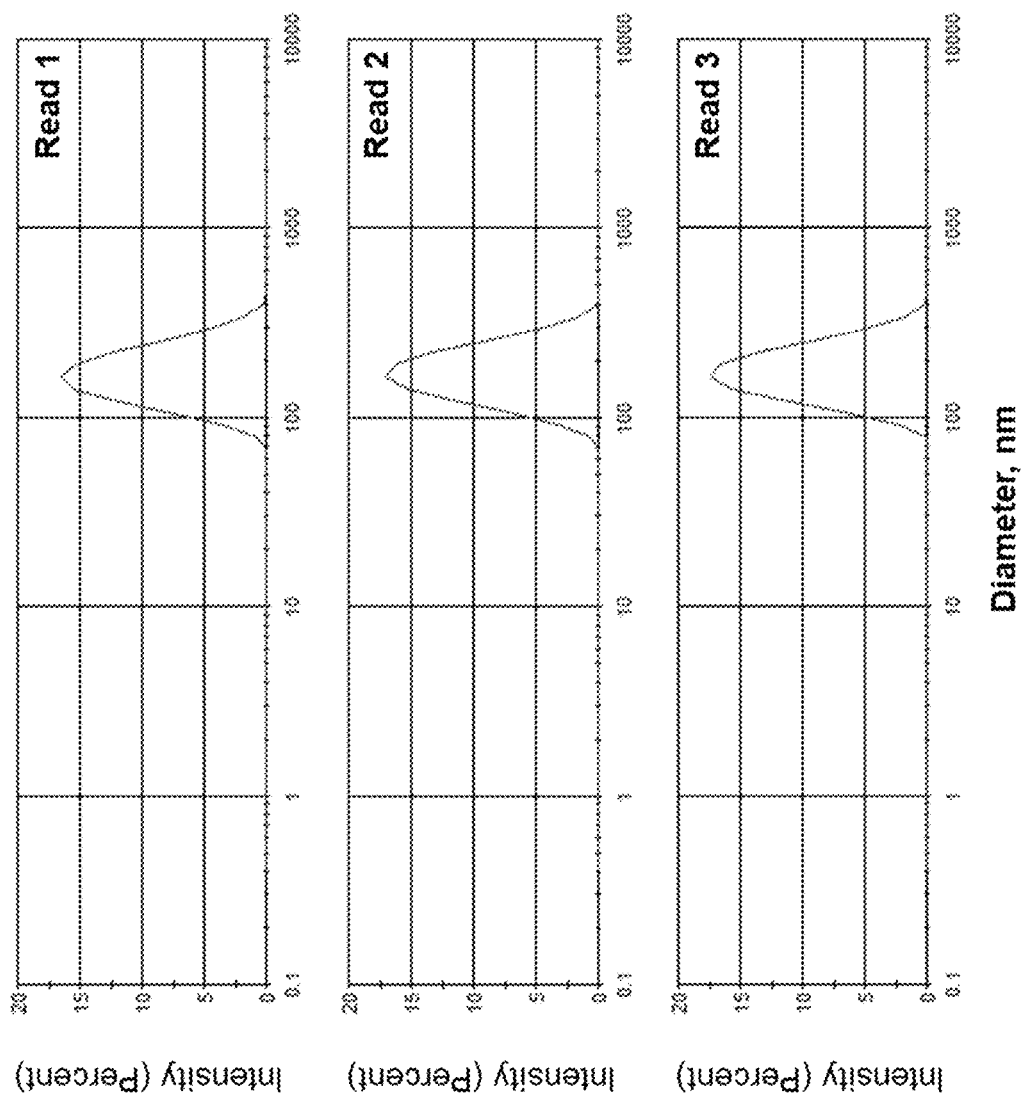
FIG. 10 are the dynamic light scattering profiles (3 reads) of nanoparticles generated from dimerized mRNA encoding SEAP on the first mRNA and Luciferase on the second mRNA. The data depicts the particle size distribution, and the results of three separate read cycles on a Malvern Zetasizer Nano ZS are shown.

FIG. 10 is a schematic diagram showing an exemplary method of creating a tail-to-tail mRNA dimer by directly reacting the chemically reactive moieties present at the mRNA 3' termini to each other. If mRNA 1 and 2 are identical, this reaction yields a homodimer. If mRNA 1 and 2 are different, this reaction yields a heterodimer.

Figure 1D:
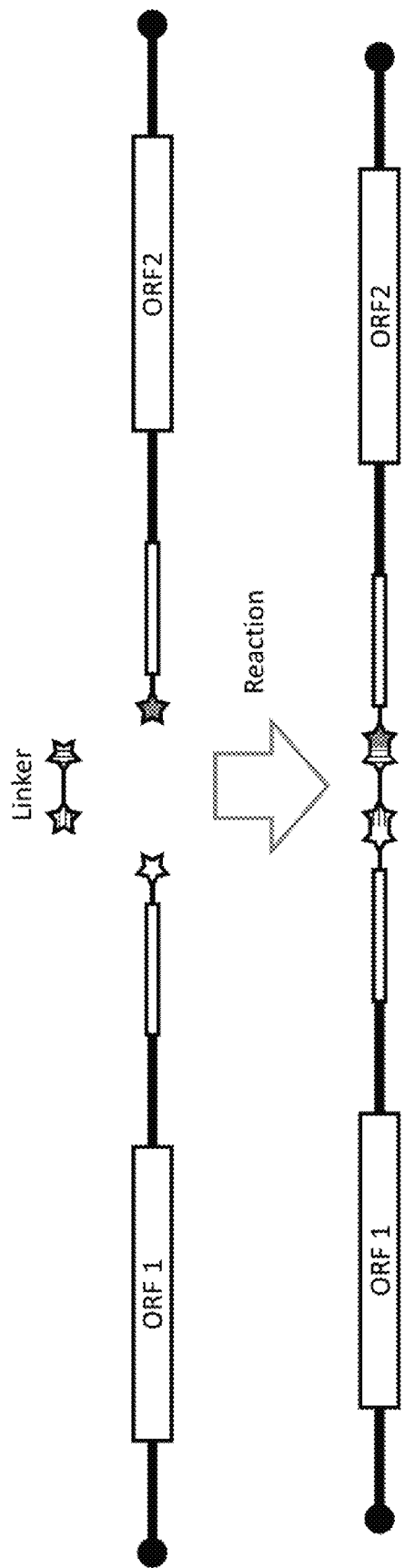
FIG. 1D is a schematic diagram showing an exemplary method of creating a tail-to-tail mRNA dimer by reacting the chemically addressable reactive moieties present at the mRNA 3' termini to a bifunctional linker. The two functionalities on the linker (illustrated as stars) may be identical or different in chemical nature from each other. If mRNA 1 and 2 are identical, this reaction yields a homodimer. If mRNA 1 and 2 are different, this reaction yields a heterodimer.

FIG. 1D is a schematic diagram showing an exemplary method of creating a tail-to-tail mRNA dimer by reacting the chemically reactive moieties present at the mRNA 3' termini to a bifunctional linker. The two functionalities on the linker (illustrated as stars) may be identical or different in chemical nature from each other. If mRNA 1 and 2 are identical, this reaction yields a homodimer. If mRNA 1 and 2 are different, this reaction yields a heterodimer.

Example 2. Method of Producing a Heterofunctional RNA Multimer

Multiple different mRNAs may be attached tail-to-tail in a desired ratio in order to mediate certain desired biological effects in a cell. Delivery of transcripts in specific ratios is critical to enabling the assembly of complex structures, or mediating complex biochemical reactions. For example, assembly of a functional adeno-associated virus capsid requires proteins VP1, VP2, and VP3 in an estimated ratio of 1:1:10 (Worner et al. 2020, Adeno-associated virus capsid assembly is divergent and stochastic, bioRxiv.

As another example, coronavirus virions are composed of an estimated 1100 Membrane (M2) proteins and 270 Spike (S) proteins, representing approximately 4:1 ratio of these vital structural components (Bar-On et al. 2020, SARS-CoV-2 (COVID-19) by the numbers, eLife; 9: e57309).

As a final example, production of a heterodimeric scFv-Fab-Fc ("triple F") antibody molecule such as XENP13551 for the treatment of hematopoietic malignancies requires the precise molecular assembly of two Ig heavy chains and one Ig light chain (WO2015149077A1). An exemplary method of producing a heterofunctional RNA multimer is to chemically functionalize the 3' end of two or more RNA molecules as described above with a reactive chemical moiety that is the same for each RNA. The RNAs are then reacted in a selected ratio to a linker carrying a number of chemical moieties (for example, 3 to 5) that react with those installed on the mRNA molecules nonselectively. The ratio of RNA molecules conjugated covalently by their 3' tail-ends to the linker will reflect the molar ratio of RNAs present at the onset of the reaction, and thus the stoichiometry of the reaction will favor a specific product. To eliminate undesired side-products of the reaction, the correct product can be purified by a method such as size exclusion chromatography (SEC).

Figure 2A:
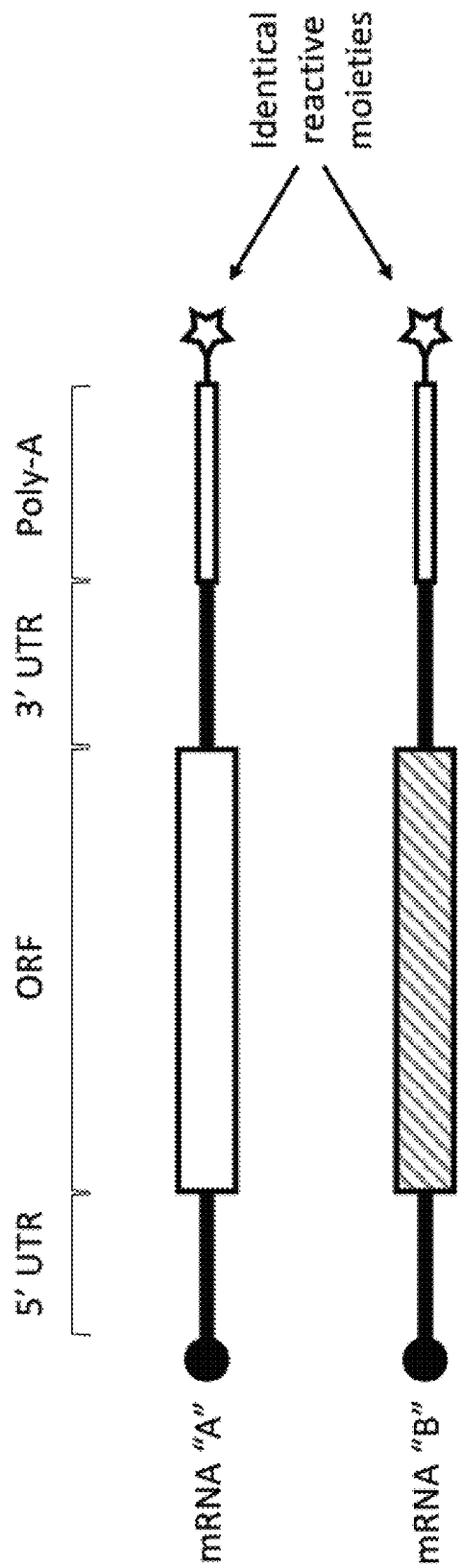
FIGS. 2A-2B are schematic diagrams showing creation of a dimer (FIG. 2A) and trimer (FIG. 2B) of tail-tail RNA conjugates disclosed herein.

FIG. 2A is a schematic diagram showing an example of two linear mRNA molecules comprising identical reactive moieties on their terminal 3' nucleotides. mRNA "A" and mRNA "B" encode different proteins in this example and thus the ORFs differ. The 5' UTR and 3'UTR/poly-A tails may or may not be identical in sequence, and the poly-A tail is optional depending on the specific application.

Figure 2B:
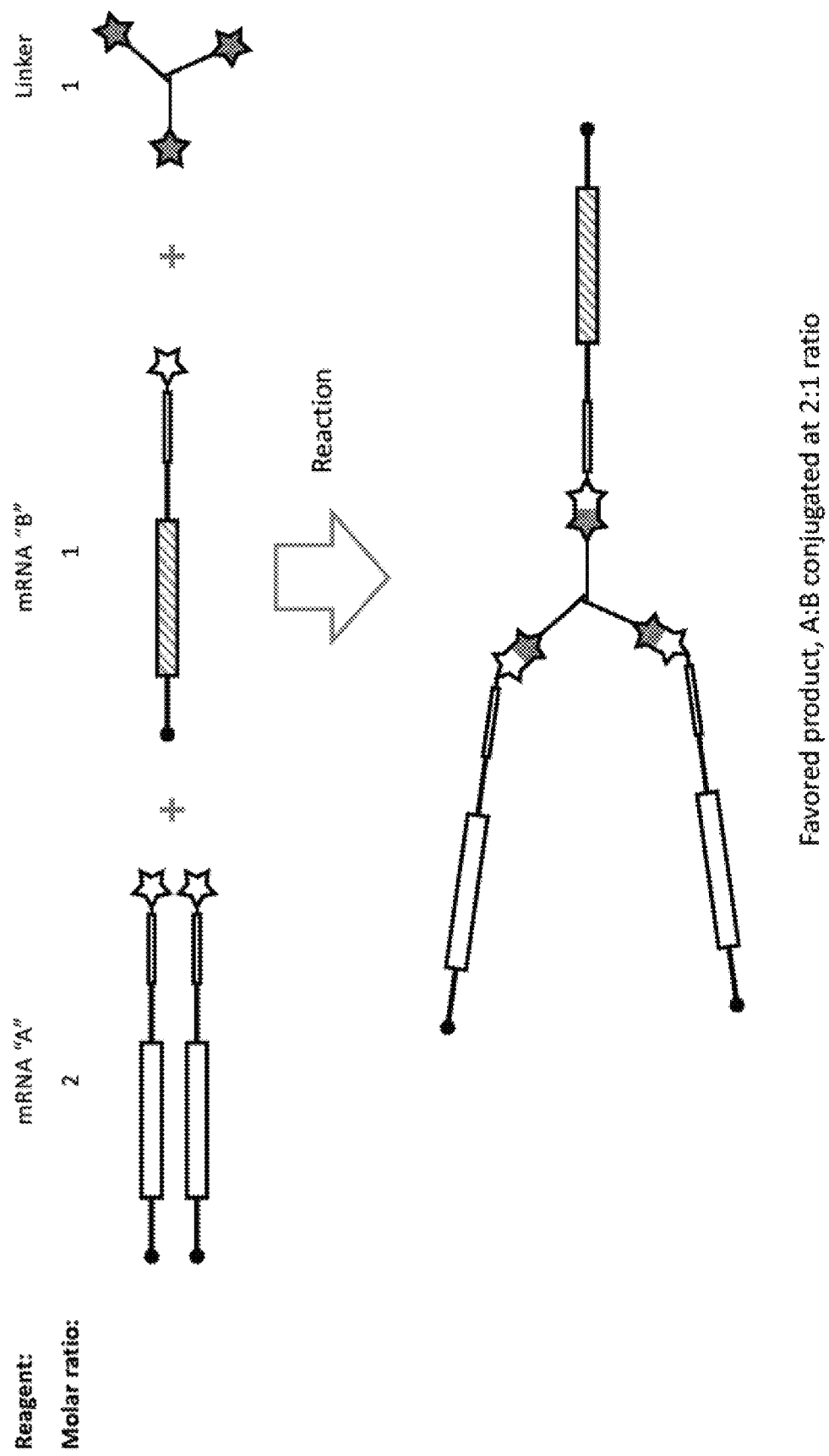

FIG. 2B is a schematic diagram showing an exemplary method of creating a heterofunctional mRNA trimer by reacting a defined molar ratio of 3' chemically functionalized RNAs to a trifunctional linker. This reaction favors yield of a heterotrimer carrying a ratio of mRNA A and B defined by the input molarity of each nucleic acid. The list of the sequences included in this application is presented in Table 1.

TABLE 1

Description of the sequences

| SEQ ID NO | Description | DNA/RNA/AA |
|---|---|---|
| 1 | SEAP mRNA | RNA |
| 2 | Luciferase mRNA | RNA |
| 3 | eGFP mRNmA | RNA |
| 4 | mCherry mRNA | ENA |
| 5 | Influenza strain PR8 hemagglutinin (HA) mRNA | RNA |
| 6 | RANTES mRNA | RNA |
| 7 | SEAP protein | AA |
| 8 | Luciferase protein | AA |
| 9 | eGFP | AA |
| 10 | mCherry protein | AA |
| 11 | Influenza strain PR8 hemagglutinin (HA) protein | AA |
| 12 | RANTES | Aa |
| 13 | SEAP mRNA + 3dAS | RNA/DNA |
| 14 | Luciferase mRNA + 3dAS | RNA/DNA |
| 15 | eGFP mRNA + 3dAs | RNA/DNA |
| 16 | mCherry mRNA + 3dAs | RNA/DNA |
| 17 | Influenza strain PR8 hemagglutinin (HA) mRNA+3dAs | RNA/DNA |
| 18 | RANTES mRNA + 3dAS | RNA/DNA |
| 19 | Trastuzumab heavy chain mRNA | RNA |
| 20 | Trastuzumab light chain mRNA | RNA |
| 1 | SEAP mRNA | RNA |

Example 3. Tail-Tail mRNA Dimer of Two Identical mRNAs

To demonstrate the advantages of an mRNA conjugate comprising a first mRNA linked by its 3' to second mRNA molecule identical in sequence, an mRNA encoding a secreted embryonic alkaline phosphatase (SEAP) protein was used as the monomer in a reaction to generate an mRNA dimer. The sequence of this SEAP mRNA is provided as SEQ ID NO: 1. To generate the dimer, a short custom nucleotide linker was commercially synthesized (Integrated DNA Technologies, Inc., Coralville, IA, USA) to crosslink the 3' hydroxyl groups.

FIGS. 3A-3E illustrate creation of a tail-tail RNA conjugated dimer including two identical mRNA molecules encoding a secreted embryonic alkaline phosphatase (SEAP) protein.

The sequence of the resulting dimer is shown below. In this sequence, the RNA residues (SEQ ID NO: 1) are denoted in capital letters and the DNA residues of the phospholinker are underlined small letters. Two RNA/DNA sequences of SEQ ID NO: 13 are connected at their 3' end by phosphate "p".

(SEQ ID NO: 13)
5' GGGAGACCCAAGCUAAUGGACUACGACAUAGUCUAGU

CCGCCAAGUCUAGGCCGCCACCAUGCUGGGGCCCUGCAUG

CUGCUGCUGCUGCUGCUGGGGCCUGAGGCUACAGCUCU

CCCUGGGCAUCAUCCCAGUUGAGGAGGAGAACCCGGACUU

CUGGAACCGCGAGGCAGCCGAGGCCCUGGGUGCCGCCAAG

AAGCUGCAGCCUGCACAGACAGCCGCCAAGAACCUCAUCA

UCUUCCUGGGCGAUGGGAUGGGGGUGUCUACGGUGACAGC

UGCCAGGAUCCUAAAAGGGCAGAAGAAGGACAAACUGGGG

CCUGAGAUACCCCUGGCCAUGGACCGCUUCCCAUAUGUGG

CUCUGUCCAAGACAUACAAUGUAGACAAACAUGUGCCAGA

CAGUGGAGCCACAGCCACGGCCUACCUGUGCGGGUCAAG

GGCAACUUCCAGACCAUUGGCUUGAGUGCAGCCGCCCGCU

UUAACCAGUGCAACACGACACGCGGCAACGAGGUCAUCUC

CGUGAUGAAUCGGGCCAAGAAAGCAGGGAAGUCAGUGGGA

```
GUGGUAACCACCACACGAGUGCAGCACGCCUCGCCAGCCG
GCACCUACGCCCACACGGUGAACCGCAACUGGUACUCGGA
CGCCGACGUGCCUGCCUCCGCCCGCCAGGAGGGGUGCCAG
GACAUCGCUACGCAGCUCAUCUCCAACAUGGACAUUGACG
UGAUCCUAGGUGGAGGCCGAAAGUACAUGUUUCGCAUGGG
AACCCCAGACCCUGAGUACCCAGAUGACUACAGCCAAGGU
GGGACCAGGCUGGACGGGAAGAAUCUGGUGCAGGAAUGGC
UGGCGAAGCGCCAGGGUGCCCGGUAUGUGUGGAACCGCAC
UGAGCUCAUGCAGGCUUCCCUGGACCCGUCUGUGACCCAU
CUCAUGGGUCUCUUUGAGCCUGGAGACAUGAAAUACGAGA
UCCACCGAGACUCCACACUGGACCCCUCCCUGAUGGAGAU
GACAGAGGCUGCCCUGCGCCUGCUGAGCAGGAACCCCCGC
GGCUUCUUCCUCUUCGUGGAGGGUGGUCGCAUCGACCAUG
GUCAUCAUGAAAGCAGGGCUUACCGGGCACUGACUGAGAC
GAUCAUGUUCGACGACGCCAUUGAGAGGGCGGGCCAGCUC
ACCAGCGAGGAGGACACGCUGAGCCUCGUCACUGCCGACC
ACUCCCACGUCUUCUCCUUCGGAGGCUACCCCCUGCGAGG
GAGCUCCAUCUUCGGGCUGGCCCCUGGCAAGGCCCGGGAC
AGGAAGGCCUACACGGUCCUCCUAUACGGAAACGGUCCAG
GCUAUGUGCUCAAGGACGGCGCCCGGCCGGAUGUUACCGA
GAGCGAGAGCGGGAGCCCCGAGUAUCGGCAGCAGUCAGCA
GUGCCCUGGACGAAGAGACCCACGCAGGCGAGGACGUGG
CGGUGUUCGCGCGCGGCCCGCAGGCGCACCUGGUUCACGG
CGUGCAGGAGCAGACCUUCAUAGCGCACGUCAUGGCCUUC
GCCGCCUGCCUGGAGCCCUACACCGCCUGCGACCUGGCGC
CCCCCGCCGGCACCACCGACGCCGCGCACCCGGGGUGAAU
ACAGCAGCAAUUGGCAAGCUGCUCUAGAGCUGCCUUCUGC
GGGGCUUGCCUUCUGGCCAUGCCCUUCUUCUCUCCCUUGC
ACCUGUACCUCUUGGUCUUUGAAUAAAGCCUGAGUAGGAA
GUGAGGGGCGCCAUUUCAAAAAAAAAAAAAAAAAAAAAA
AAAAAAAAAAAAAAAAAAAAAAAAAAAAAAAAAAAA
AAAAAAAAAAAAAAAAAAAAAAAAAAAAAAAAAa
aa-3'-p-3'aaaAAAAAAAAAAAAAAAAAAAAAAAAAA
AAAAAAAAAAAAAAAAAAAAAAAAAAAAAAAAAAAA
AAAAAAAAAAAAAAAAAAAAAAAAAAAACUUUACC
GCGGGGAGUGAAGGAUGAGUCCGAAAUAAGUUUCUGGUU
CUCCAUGUCCACGUUCCCUCUCUUCUUCCCGUACCGGUCU
UCCGUUCGGGGCGUCUUCCGUCGAGAUCUCGUCGAACGGU
UAACGACGACAUAAGUGGGGCCCACGCGCCGCAGCCACCA
CGGCCGCCCCCGCGGUCCAGCGUCCGCCACAUCCCGAGG
UCCGUCCGCCGCUUCCGGUACUGCACGCGAUACUUCCAGA
CGAGGACGUGCGGCACUUGGUCCACGCGGACGCCCGGCGC
GCGCUUGUGGCGGUGCAGGAGCGGACGCACCCAGAGAAGC
AGGUCCCCGUGACGACUGACGACGGCUAUGAGCCCCGAGG
GCGAGAGCGAGAGCCAUUGUAGGCCGGCCCGCGGCAGGAA
CUCGUGUAUCGGACCUGGCAAAGGCAUAUCCUCCUGGCAC
AUCCGGAAGGACAGGGCCCGGAACGGUCCCCGGUCGGGCU
UCUACCUCGAGGGAGCGUCCCCCAUCGGAGGCUUCCUCUU
CUGCACCCUCACCAGCCGUCACUGCUCCGAGUCGCACAGG
AGGAGCGACCACUCGACCGGGCGGGAGAGUUACCGCAGCA
GCUUGUACUAGCAGAGUCAGUCACGGGCCAUUCGGGACGA
AAGUACUACUGGUACCAGCUACGCUGGUGGGAGGUGCUUC
UCCUUCUUCGGCGCCCCCAAGGACGAGUCGUCCGCGUCCC
GUCGGAGACAGUAGAGGUAGUCCCUCCCCAGGUCACACCU
CAGAGCCACCUAGAGCAUAAAGUACAGAGGUCCGAGUUUC
UCUGGGUACUCUACCOAGUGUCUGCCCAGGUCCCUUCGGA
CGUACUCGAGUCACGCCAAGGUGUGUAUGGCCCGUGGGAC
CGCGAAGCGGUCGGUAAGGACGUGGUCUAAGAAGGGCAGG
UCGGACCAGGGUGGAACCGACAUCAGUAGACCCAUGAGUC
CCAGACCCCAAGGGUACGCUUUGUACAUGAAAGCCGGAGG
UGGAUCCUAGUGCAGUUACAGGUACAACCUCUACUCGACG
CAUCGCUACAGGACCGUGGGGAGGACCGCCCGCCUCCGUC
CGUGCAGCCGCAGGCUCAUGGUCAACGCCAAGUGGCACAC
CCGCAUCCACGGCCGACCGCUCCGCACGACGUGAGCACAC
CACCAAUGGUGAGGGUGACUGAAGGGACGAAAGAACCGGG
CUAAGUAGUGCCUCUACUGGAGCAACGGCGCACAGCACAA
CGUGACCAAUUUCGCCCGCCGACGUGAGUUCGGUUACCAG
ACCUUCAACGGGAACUGGGGCGUGUCCAUCCGGCACCGAC
ACCGAGGUGACAGACCGUGUACAAACAGAUGUAACAUACA
GAACCUGUCUCGGUGUAUACCCUUCGCCAGGUACCGGUCC
CCAUAGAGUCCGGGUCAAACAGGAAGAAGACGGGAAAAU
CCUAGGACCGUCGACAGUGGCAUCUGUGGGGUAGGGUAG
CGGGUCCUUCUACUACUCCAAGAACCGCCGACAGACACGU
CCGACGUCGAAGAACCGCCGUGGGUCCCGGAGCCGACGGA
GCGCCAAGGUCUUCAGGCCCAAGAGGAGGAGUUGACCCUA
CUACGGGUCCCUCUCGACAUCGGAGUCCGGGUCGUCGUCG
UCGUCGUCGUCGUACGUCCCGGGGUCGUACCACCGCCGGA
UCUGAACCGCCUGAUCUGAUACAGCAUCAGGUAAUCGAAC
CCAGAGGG 5'
(SEQ ID NO" 13)
```

Figure 3A:
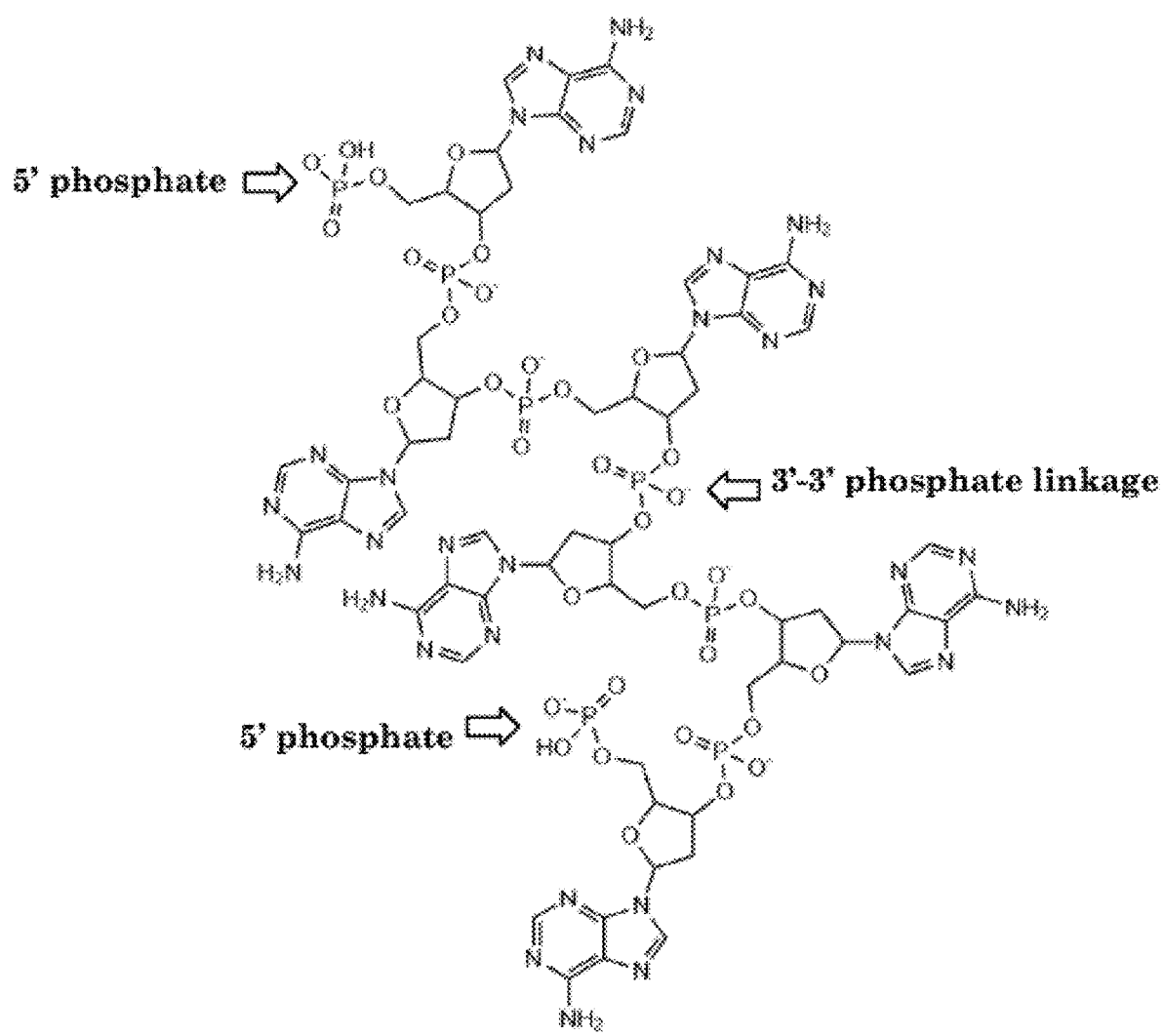
FIGS. 3A-3E illustrate creation of a tail-tail RNA conjugated dimer including two identical mRNA molecules encoding a secreted embryonic alkaline phosphatase (SEAP) protein.

FIG. 3A is a chemical formula of a DNA linker that includes six consecutive deoxyadenosine (dA) residues connected by phosphodiester bonds. This figure shows the linker that consists of six deoxyadenosine (dA) residues in sequence connected by phosphodiester bonds, wherein the first three dA's are in typical 5'-to-3' sequence, followed by an atypical phosphodiester bond that connects the 3' hydroxyls of the third and fourth dA residues. The fourth through sixth dA residues are connected by typical phosphodiester bonds, but are oriented 3'-to-5' relative to the first three dA residues. The sequence of the linker is p-(5')-dA-p-dA-p-dA-(3')-p-(3')-dA-p-dA-p-dA-(5')-p, where the lowercase "p" indicates a phosphate group. This is henceforth referred to as a "dA6 phospholinker".

Figure 3B:
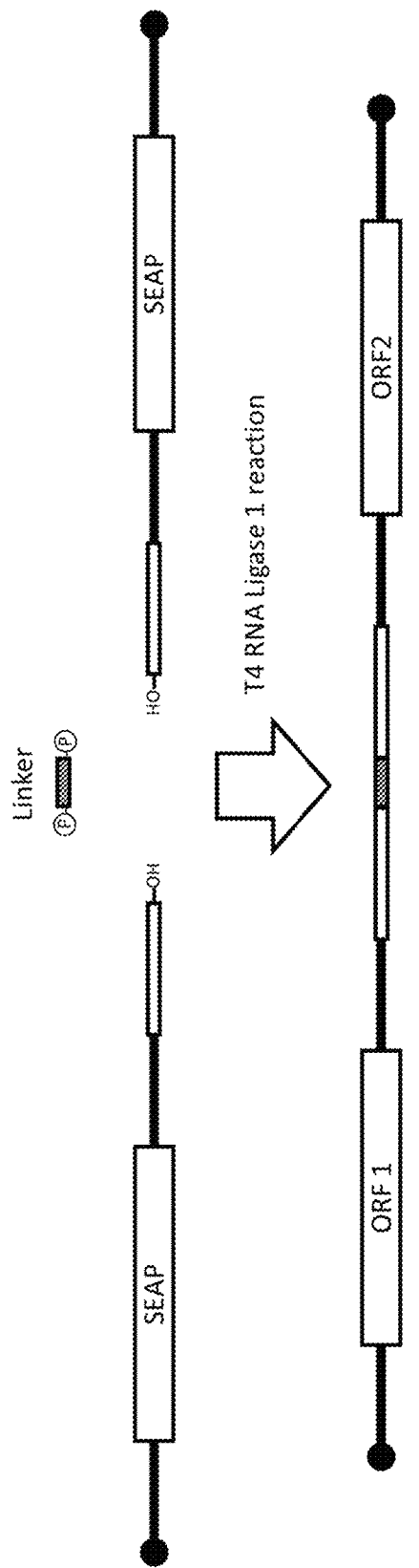
Figure 3C:
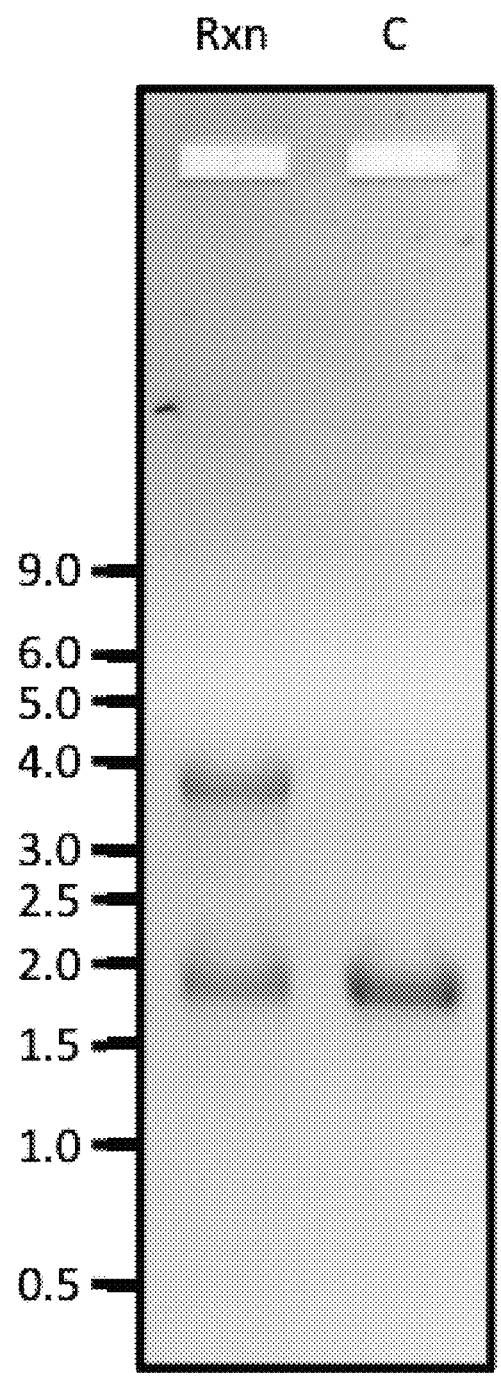
Figure 3D:
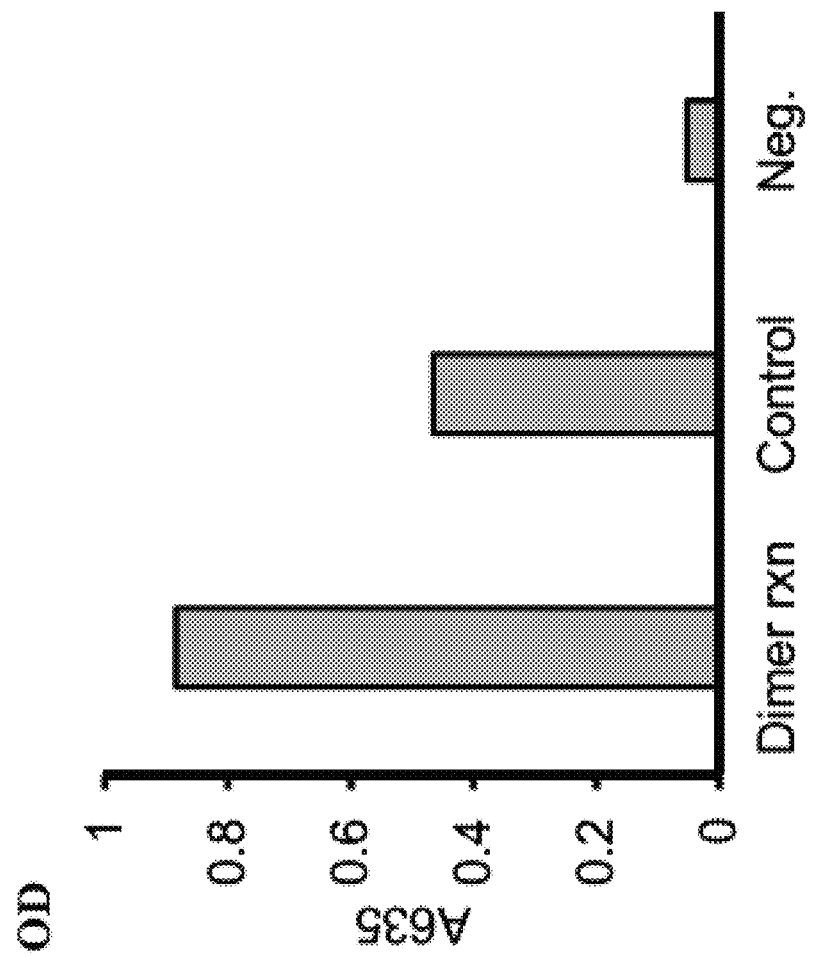

To synthesize the dimer, the SEAP mRNA, which carries a 5' cap and 3' hydroxyl at its termini, was pretreated with alkaline phosphatase (New England Biolabs, Inc., Ipswich, MA, USA) to remove any extraneous 5' phosphate groups following the manufacturer's instructions. The mRNA was purified by LiCl precipitation using a 7.5M Precipitation Solution (Thermo Fisher Scientific, Waltham, MA, USA) according to the manufacturer's instructions. The purified, dephosphorylated mRNA was mixed with the dA6 phospholinker in a 2:1 molar ratio, in $H_2O$. The mRNA and linker solution were added to 20 µl of a T4 RNA Ligase 1 reaction mixture containing 50 mM Tris-HCl, pH 7.5, 10 mM $MgCl_2$, 1 mM DTT, 10% PEG8000, 1 mM ATP, and 30 units of T4 RNA Ligase 1 (New England Biolabs, Inc., Ipswich, MA, USA). The reaction contained 16 pmol of SEAP mRNA, and 8 pmol of the dA6 phospholinker. A negative control reaction was performed in parallel where no linker was included. The reaction was incubated at 37° C. for 2 hours. FIG. 3B is a schematic diagram showing creation of an RNA dimer including two mRNA molecules encoding the SEAP protein. As depicted in FIG. 3B, the reaction would be expected to over time produce an RNA species of double the length of the input mRNA. After 2 hours, 1 µl of the reaction was sampled and analyzed by formamide denaturing agarose gel electrophoreses. FIG. 3C is a photograph of an agarose gel showing an RNA species (top band) that doubles the length of the input RNA (lower band; Rxn lane) compared to the band corresponding to control mRNA monomer (C lane). In the control reaction, only the input monomer mRNA was detected at the expected mass, based on comparison to the RNA ladder. In the presence of the dA6 phospholinker, a new RNA species appeared that was double the length of the monomer, indicating that a tail-to-tail mRNA dimer had been successfully synthesized. The reaction was allowed to proceed overnight at reduced temperature (16° C.), and all reaction components except the mRNAs were removed by LiCl purification as described above. The mRNA was resuspended in $H_2O$, and used to transfect baby hamster kidney (BHK) cells in vitro to test for expression of the encoded SEAP protein. Transfection was performed using TransIT-mRNA reagent (Mirus Bio LLC, Madison, WI, USA), using 0.25 µg of mRNA on a well of cells in a 24 well plate, and a sample of the culture media at ~12 hours post-transfection was measured for SEAP concentration by colorimetric assay (Quanti-Blue reagent, InVivoGen, USA) according to the manufacturer's instructions. FIG. 3D is a bar graph showing the expression of the SEAP RNA dimer (Dimer rxn) in baby hamster kidney (BHK) cells 12 hours post transfection compared to control monomer mRNA (control) and culture medium (neg,). This figure shows that the mRNA that was reacted to produce a dimer exhibited greater SEAP expression than the negative control reaction mRNA, by a factor of 1.9×.

Figure 3E:
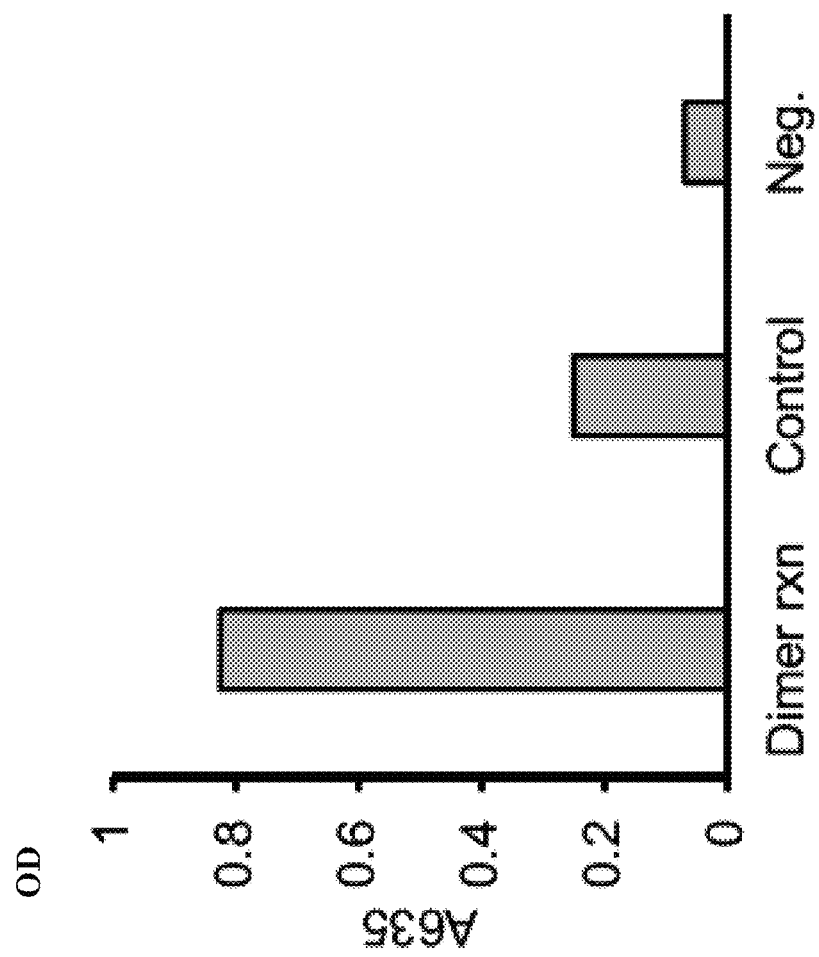

The medium on the cells was changed, and the cells were permitted to continue incubating, and after an additional 12 hours the measurement was repeated. FIG. 3E is a bar graph showing the expression of the SEAP RNA dimer (Dimer rxn) in baby hamster kidney (BHK) cells 24 hours post transfection compared to control monomer mRNA (control) and culture medium (neg,). As shown in FIG. 3E, the dimer SEAP mRNA transfection now exhibited a factor of 3.3× greater expression than the control mRNA, indicating that over time the decay of expression driven by dimerized mRNA was slower than for conventional monomeric mRNA.

Example 4. Tail-Tail mRNA Dimer of Two Different Reporter Gene mRNAs

Figure 4A:
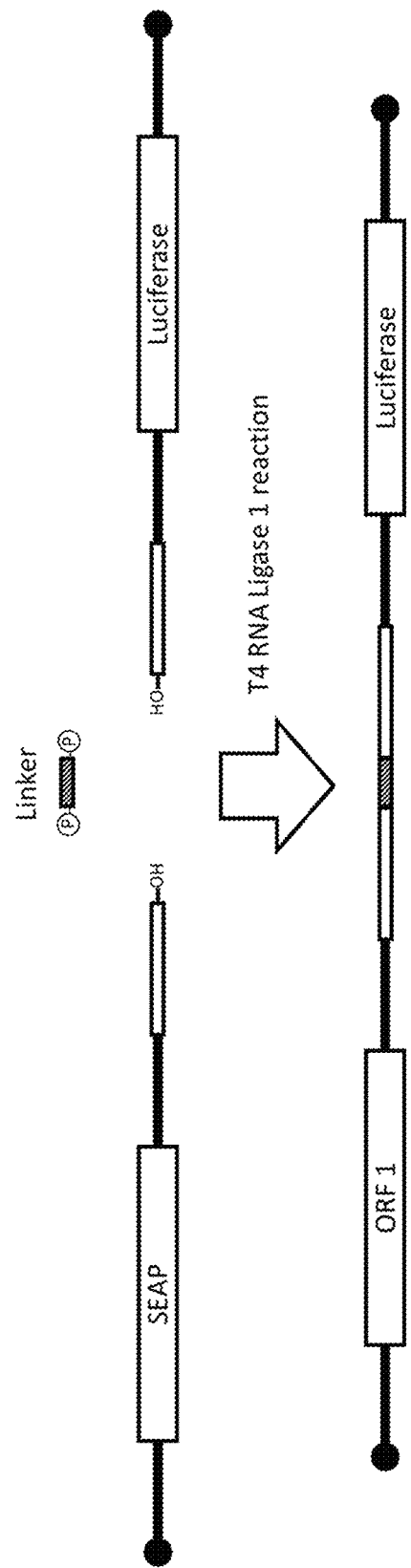
FIGS. 4A-4D illustrate creation of a tail-tail RNA conjugated dimer including two different mRNA molecules, one of which encodes a SEAP protein and another one encodes a Firefly luciferase protein.

Given the success of the SEAP homodimer mRNA and improved performance, a similar experiment was performed to evaluate the efficacy of two different mRNAs conjugated by the same method. FIGS. 4A-4D illustrate creation of a tail-tail RNA conjugated dimer including two different mRNA molecules, one of which encodes a SEAP protein and another one encodes a Firefly luciferase protein. FIG. 4A is a schematic diagram showing creation of an RNA dimer similar to the dimer shown in FIG. 2B but including two different mRNA molecules, one of which encodes the SEAP protein and another one encodes a Firefly luciferase protein (SEAP-Luc dimer).

Figure 4B:
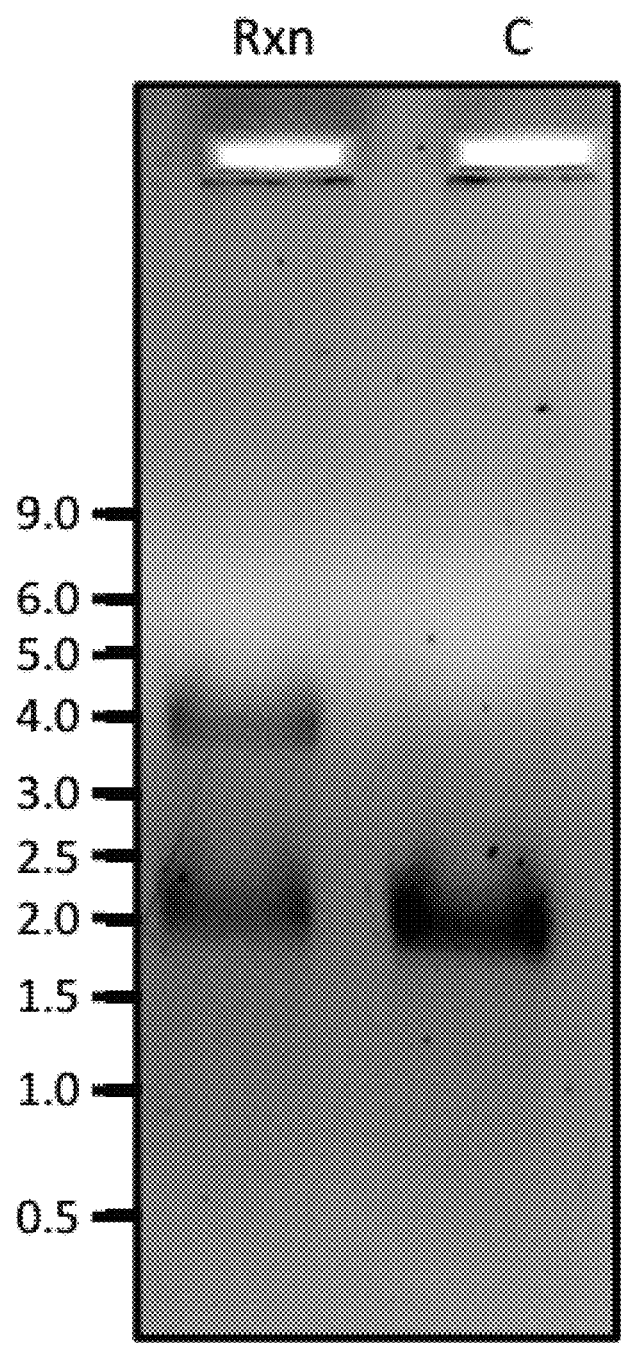

The same SEAP mRNA as in Example 3 was mixed in a 1:1 molar ratio with an mRNA of similar design (carrying a 5' cap and UTR, and 3' hydroxyl and UTR) but encoding a Firefly Luciferase (Luc) reporter gene; the sequence of this mRNA is set forth as SEQ ID NO: 2. These mRNAs were treated with alkaline phosphatase, purified, and mixed into 20 µl T4 RNA Ligase 1 reactions with or without the dA6 phospholinker following the same conditions as described for Example 1. The total mass of mRNA in a 20 µl reaction was again ~16 pmol, with ~8 pmol dA phospholinker. After 2 hours, samples were harvested and analyzed by formamide denaturing agarose gel electrophoresis, and in the presence of the dA phospholinker, again a new RNA species corresponding to double the size of the individual mRNAs was detected. FIG. 4B is a photograph of an agarose gel showing an RNA species (top band) that doubles the length of the input RNA (lower band; Rxn lane) compared to the band corresponding to control mRNA monomer (C lane) of the expected mass based on comparison to the RNA ladder. The control mRNA monomer is the starting material of the dimerization reaction, as this sample was taken from the control reaction wherein no dA6 phospholinker was included and therefore serves as an ideal comparator to prove that the double-length product in the Rxn lane was the result of dimerization by reaction with the linker. This control starting material is an equimolar mixture of SEAP mRNA and Luc mRNA, exactly the same as the input material in the dimerization reaction and subjected to the same conditions except without linker. The sequence of the resulting dimer is shown below. In this sequence, the RNA residues (SEQ ID NOs: 1 and 2) are denoted in capital letters and the DNA residues of the phospholinker are underlined small letters. Two RNA/DNA sequences of SEQ ID NOs: 13 and 14 are connected at their 3' end by phosphate "p".

(SEQ ID NO: 13)
5' GGGAGACCCAAGCUAAUGGACUACGACAUAGUCUAGU

CCGCCAAGUCUAGGCCGCCACCAUGCUGGGGCCCUGCAUG

CUGCUGCUGCUGCUGCUGCUGGGCCUGAGGCUACAGCUCU

-continued

CCCUGGGCAUCAUCCCAGUUGAGGAGGAGAACCCGGACUU
CUGGAACCGCGAGGCAGCCGAGGCCCUGGGUGCCGCCAAG
AAGCUGCAGCCUGCACAGACAGCCGCCAAGAACCUCAUCA
UCUUCCUGGGCGAUGGGAUGGGGGUGUCUACGGUGACAGC
UGCCAGGAUCCUAAAAGGGCAGAAGAAGGACAAACUGGGG
CCUGAGAUACCCCUGGCCAUGGACCGCUUCCCAUAUGUGG
CUCUGUCCAAGACAUACAAUGUAGACAAACAUGUGCCAGA
CAGUGGAGCCACAGCCACGGCCUACCUGUGCGGGGUCAAG
GGCAACUUCCAGACCAUUGGCUUGAGUGCAGCCGCCCGCU
UUAACCAGUGCAACACGACACGCGGCAACGAGGUCAUCUC
CGUGAUGAAUCGGGCCAAGAAAGCAGGGAAGUCAGUGGGA
GUGGUAACCACCACACGAGUGCAGCACGCCUCGCCAGCCG
GCACCUACGCCCACGGUGAACCGCAACUGGUACUCGGA
CGCCGACGUGCCUGCCUCCGCCCGCCAGGAGGGGUGCCAG
GACAUCGCUACGCAGCUCAUCUCCAACAUGGACAUUGACG
UGAUCCUAGGUGGAGGCCGAAAGUACAUGUUUCGCAUGGG
AACCCCAGACCCUGAGUACCAGAUGACUACAGCCAAGGU
GGGACCAGGCUGGACGGGAAGAAUCUGGUGCAGGAAUGGC
UGGCGAAGCGCCAGGGUGCCCGGUAUGUGUGGAACCGCAC
UGAGCUCAUGCAGGCUUCCCUGGACCCGUCUGUGACCCAU
CUCAUGGGUCUCUUUGAGCCUGGAGACAUGAAAUACGAGA
UCCACCGAGACUCCACACUGGACCCCUCCCUGAUGGAGAU
GACAGAGGCUGCCCUGCGCCUGCUGAGCAGGAACCCCCGC
GGCUUCUUCCUCUUCGUGGAGGGUGGUCGCAUCGACCAUG
GUCAUCAUGAAAGCAGGGCUUACCGGGCACUGACUGAGAC
GAUCAUGUUCGACGACGCCAUUGAGAGGGCGGGCCAGCUC
ACCAGCGAGGAGGACACGCUGAGCCUCGUCACUGCCGACC
ACUCCCACGUCUUCUCCUUCGGAGGCUACCCCCUGCGAGG
GAGCUCCAUCUUCGGGCUGGCCCCUGGCAAGGCCCGGGAC
AGGAAGGCCUACACGGUCCUCCUAUACGGAAACGGUCCAG
GCUAUGUGCUCAAGGACGGCGCCCGGCCGGAUGUUACCGA
GAGCGAGAGCGGGAGCCCCGAGUAUCGGCAGCAGUCAGCA
GUGCCCUGGACGAAGAGACCCACGCAGGCGAGGACGUGG
CGGUGUUCGCGCGCGGCCCGCAGGCGCACCUGGUUCACGG
CGUGCAGGAGCAGACCUUCAUAGCGCACGUCAUGGCCUUC
GCCGCCUGCCUGGAGCCCUACACCGCCUGCGACCUGGCGC
CCCCCGCCGGCACCACCGACGCCGCGCACCCGGGUGAAU
ACAGCAGCAAUUGGCAAGCUGCUCUAGAGCUGCCUUCUGC
GGGGCUUGCCUUCUGGCCAUGCCCUUCUUCUCUCCCUUGC
ACCUGUACCUCUUGGUCUUUGAAUAAAGCCUGAGUAGGAA

-continued

GUGAGGGGCGCCAUUUCAAAAAAAAAAAAAAAAAAAAAA
AAAAAAAAAAAAAAAAAAAAAAAAAAAAAAAAAAAAAAA
AAAAAAAAAAAAAAAAAAAAAAAAAAAAAAAAAAAAA<u>**aa
a-3'-p-3'-aaa**</u>AAAAAAAAAAAAAAAAAAAAAAAAAA
AAAAAAAAAAAAAAAAAAAAAAAAAAAAAAAAAAAAAAA
AAAAAAAAAAAAAAAAAAAAAAAAAAAAAAAACUUUACC
GCGGGGGAGUGAAGGAUGAGUCCGAAAUAAGUUUCUGGUU
CUCCAUGUCCACGUUCCCUCUCUUCUUCCCGUACCGGUCU
UCCGUUCGGGGCGUCUUCCGUCGAGAUCUCGUCGAACGGU
UAACGACGACAUACCGCGCAGUGUGCCGCUAGAACGGCGG
AAAGAACCGGAACUACUCCUAGAGAGACUAGAAAGACCGC
AGGUCGAACGGCCAGUCCGGAAAACCGUGGAGCAGGUGUU
UGUGGUGCGGCGGAGAGUCAAAGAACCGCCACCAGUGAAC
CGACCGGUGCAUCAGGUGCUAAAGAAAGAGCCAGUACCAG
AACGGCACAAGGUCGUGGUGGUGUCGUCGUCCGUCAAGCG
GUCGUAGUAGCAGUCCGUCAGGACGGUGCGGCCGUAGCUU
CUACAAUCCUACGACCUCGUCCUAUCUAAGGUCGAGCCGU
CCCCGGUGGACCAUCGGGAACAUGAACUAGUCCCUGAAGU
CAGACAGGUGCUACUUCUUCACGAGUAGAAGCAGGGUCAU
CCGUUACAGCGGCGACACGUCGGUAGGUAGGAACAGCUAG
UCUCGCAACCACCGGAGCCCCAACAAGUGCAUCGGCGAGU
ACUAGUAUCCCGGAGACUGUGUGUCGAGCGGGGAGACCAA
UUGCGGGUCACAAAAAGGCCACAGGUCCAGGUGGUGGAAC
CGGAGCUUCUUACCGUGGUGAAAAGGGUGUCGCGGUCCGA
AUAGCAGCGGGAGUCCACACUAGUCCUAUCGCGACCAACA
GAGCCAGUCAGGCAUCGGAACAGACUACGGUCCGUCUACC
UUGGAGAACCGCUGCCGAAGCGGGUGAAGAAAUCUGUCUC
CCCGAGGCGGUGAUCGCUAGAGCACGUCCAACGAGUCCAG
CAUGAAUAGCUAGUCCCACGAGAACCGUUUCUUCGACUUG
UCUCAUCCGUGGUCGUCCCGUCUGACCUAGAACAUCAGGA
CGUCCGAAGAGUCCUUGUCAAGAAGGAGCUUCGCCAUGUA
GUCGUGGUGAGACUUCGGCGUCUAGUCCAUCGGGUCACAC
CACUUGUACGGCUUCGGCACCACUUUUCCGUGGUGCGAGU
CCUACCGACACAGCCCCUACUAGACCAACGGCUUCUACCC
UAGAGACCGCACCGACUUAGACUGCGUCCGCCAAGACACU
CCGUCUCGUUGUGGAAACCCGUCAGGCCAUCUCGGCGACG
ACAAGUACUAGUCCCGCUAACAGAACAGAGACAGCUUCGA
GAGCCCGUGCUUCAGCAUGAGCAACUUCGGUCCACCGUCU
ACCGACCAGUGCUUCCACAUGUACGAGACCUUCGGGACCA
UCAGCCAGAACGACAGGUACUACUAAAAGACCUACUA
CCCGUCGAAGAAGACGUGCAAGUCCUAAAAGACGUCAGGG -continued

```
AAGAACCUGUGCUUGUGGUGCCACCCGACUCUCUACGGGU

ACGACAAGUCGUCGAGCGCGAGCAACAUCUACAGCAACCG

UCCUCGGUGUCGGUGAGGCUACUUGUCUCGCGGGUCGUGU

CCGUACUUCUUGACGUCCGACAAGAGCGACGUGUGCUGCU

AAGACACCAACCACAAGUCCGGCAUCGCGAAGUAUCGAAG

CCGGUCGGCGUGUCUGUAGAGCUUCAUGAGCCGCAUCCAC

UACAGGUGGAGCUACACUCGUAGACACUUCCGCUAACACG

GCCCGUGGUCUCGCAUAGAGAAGUACCGGAACACGUCGAC

GAGCGGCCGACAAGGUAGAAGGUCUCCCAUCUUACCUCGU

CCCGGGAAGAACUACAAGAACCGUAGAAGGUACCACCGCC

GGAUCUGAACCGCCUGAUCUGAUACAGCAUCAGGUAAUCG

AACCCAGAGGG-5'
(SEQ ID NO: 14)
```

Figure 4C:
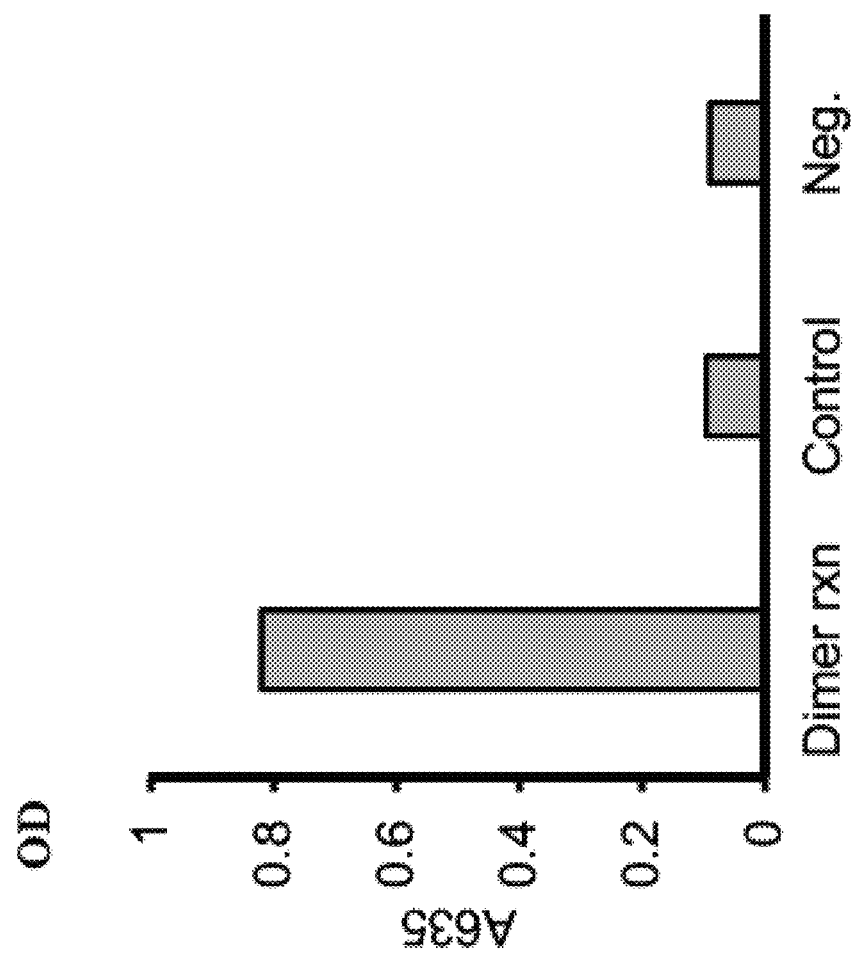

After additional overnight 16° C. incubation, the dimerization and control reactions were subjected to LiCl purification as above to isolate the mRNA, and BHK cells were transfected to study gene expression. Five days were allowed to elapse, with media changes performed daily to allow only measurement of SEAP accumulated within a specific 24 hr period. On day 6 post transfection, the cells and media were harvested. SEAP concentration in the medium was quantified as described in Example 2. FIG. 4C is a bar graph showing the SEAP expression of the SEAP-Luc RNA dimer (Dimer rxn) in baby hamster kidney (BHK) cells 5 days post transfection compared to control monomer mRNA (control) and culture medium (neg,).

Figure 4D:
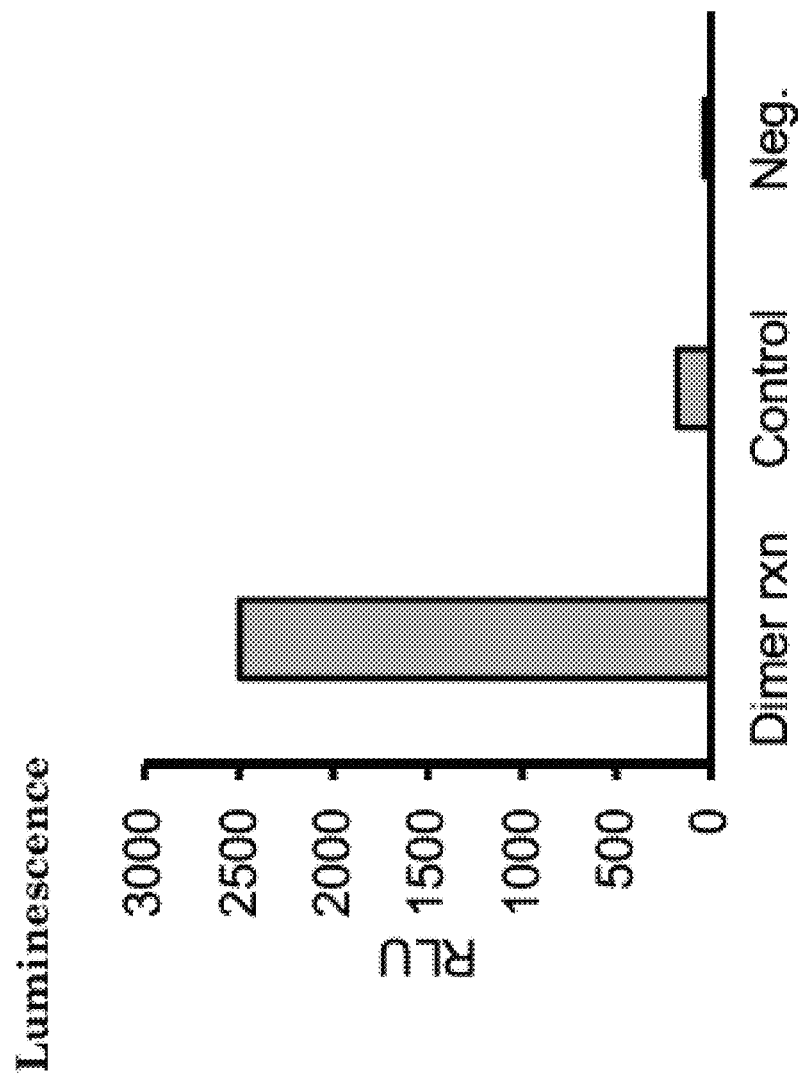

In line with the results seen for Example 2, SEAP expression using the products of the dimerization reaction was substantially greater (absorbance measured 0.82) than for the control monomeric mRNA mixture, which showed only slightly greater signal than background (0.095 absorbance, over background level of 0.09). Luc expression in the cell pellet was measured using the Pierce™ Firefly Luc One-Step Glow Assay Kit as a chemiluminescent assay (Thermo Fisher Scientific, Waltham, MA, USA). Luc expression was detected in both cell samples, but was ~14× higher in the case of the dimerized reaction sample. FIG. 4D is a bar graph showing the Luc expression of the SEAP-Luc RNA dimer (Dimer rxn) in baby hamster kidney (BHK) cells 5 days post transfection compared to control monomer mRNA (control) and culture medium (neg,).

Together, these results demonstrate that two different mRNAs covalently linked via their 3' hydroxyls to form dimers exhibit greater and more protracted gene expression potency than equivalent masses of standard unlinked monomeric mRNA controls.

Example 5. Tail-Tail mRNA Dimer of Two mRNAs Encoding Different Fluorescent Proteins Having determined that tail-to-tail conjugation of mRNAs extends the expression potential of the encoded proteins, next the level of co-delivery of conjugated mRNAs was studied. For many applications, it is desirable to simultaneously express two different proteins within a cell in order to mediate an intended biological effect. For example, one protein may enhance or otherwise regulate the activity or biological response to the other, or the two polypeptides may be required to form a complex such as in the case of antibodies (which comprise a heavy and light chain) or receptors such as EGFR, TGFβ receptor, IL-2R, PDGFR, or IGF-1R, which are composed of two different subunits. To demonstrate the efficiency of co-transfection, two mRNA molecules encoding easily-detected fluorescent proteins were selected for conjugation. The fluorescent proteins chosen were eGFP (SEQ ID NO: 3) and mCherry (SEQ ID NO: 4). FIGS. 5A-5D illustrate creation of a tail-tail RNA conjugated dimer including two different mRNA molecules, one of which encodes an eGFP protein and another one encodes an mCherry fluorescent protein.

Figure 5A:
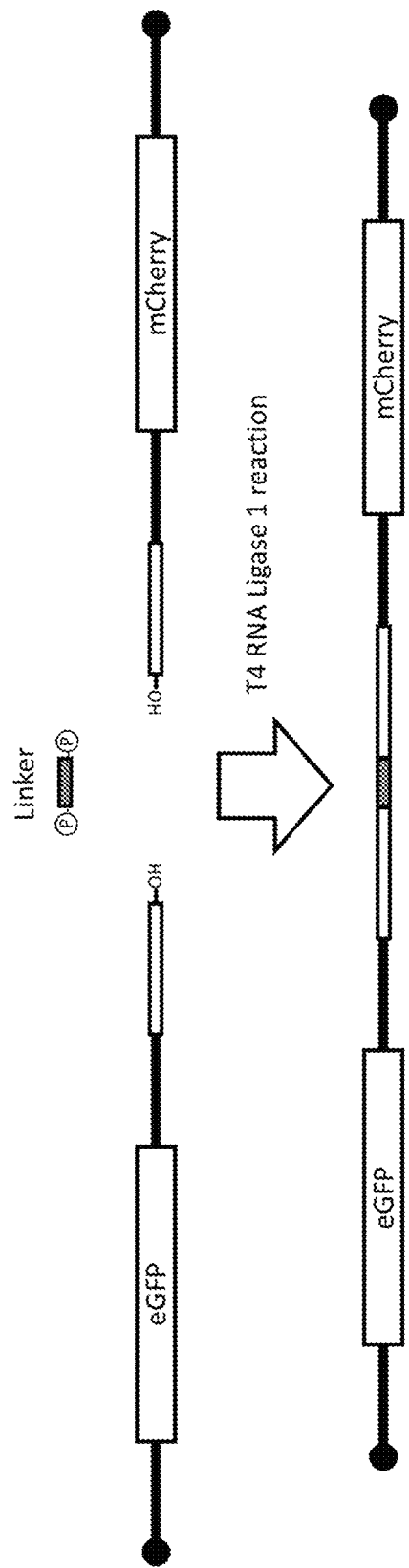
FIGS. 5A-5D illustrate creation of a tail-tail RNA conjugated dimer including two different mRNA molecules, one of which encodes an eGFP protein and another one encodes an mCherry fluorescent protein.
Figure 5B:
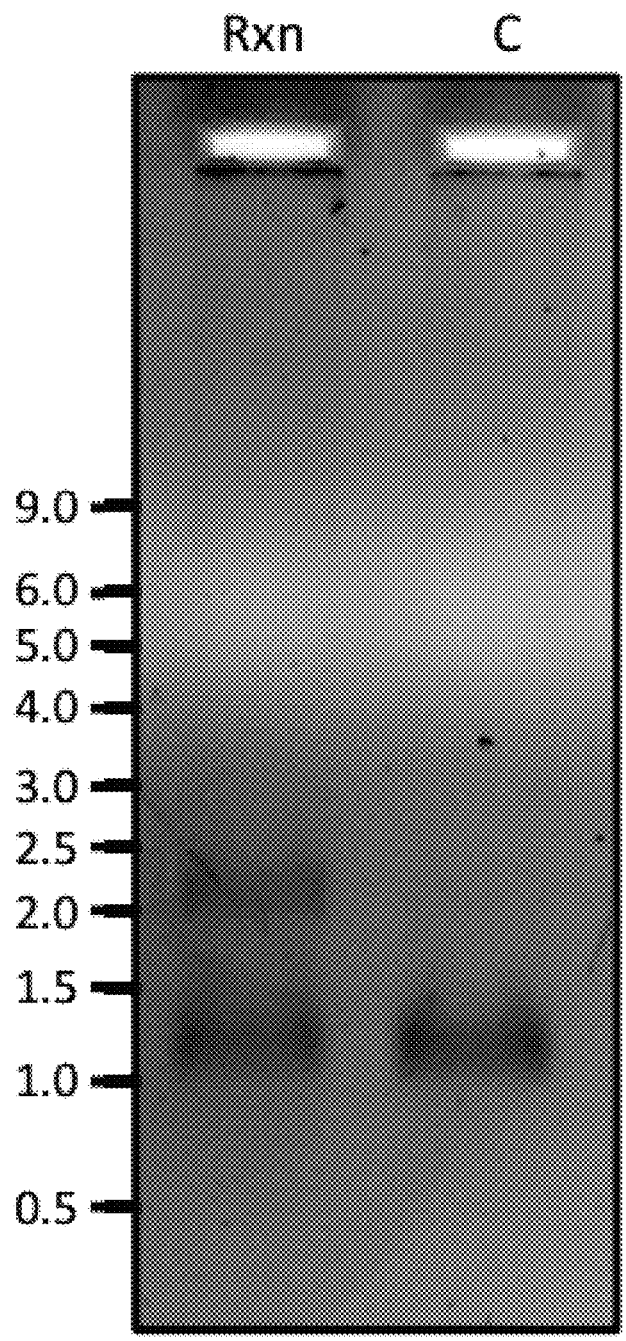
Figure 5C:
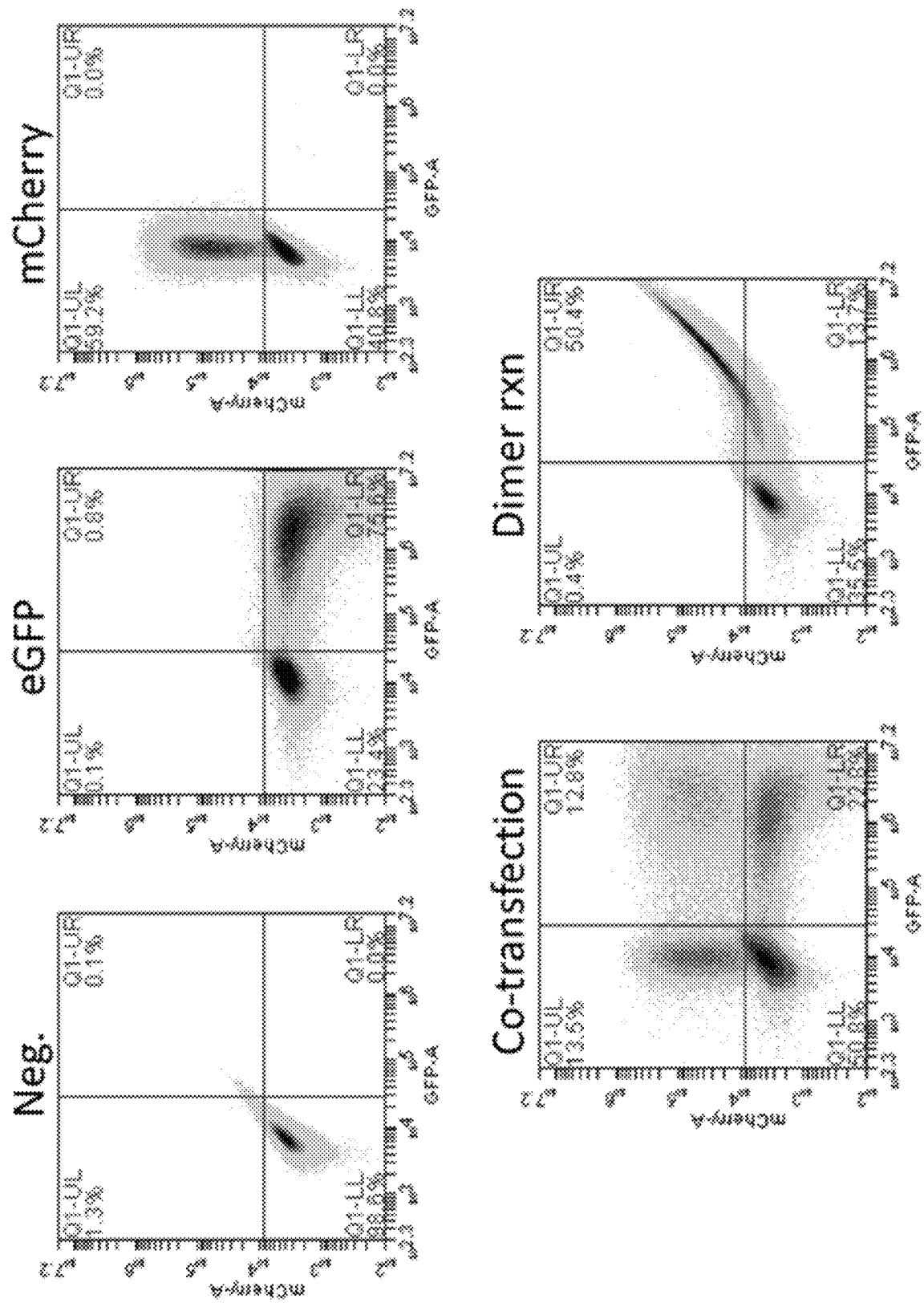
Figure 5D:
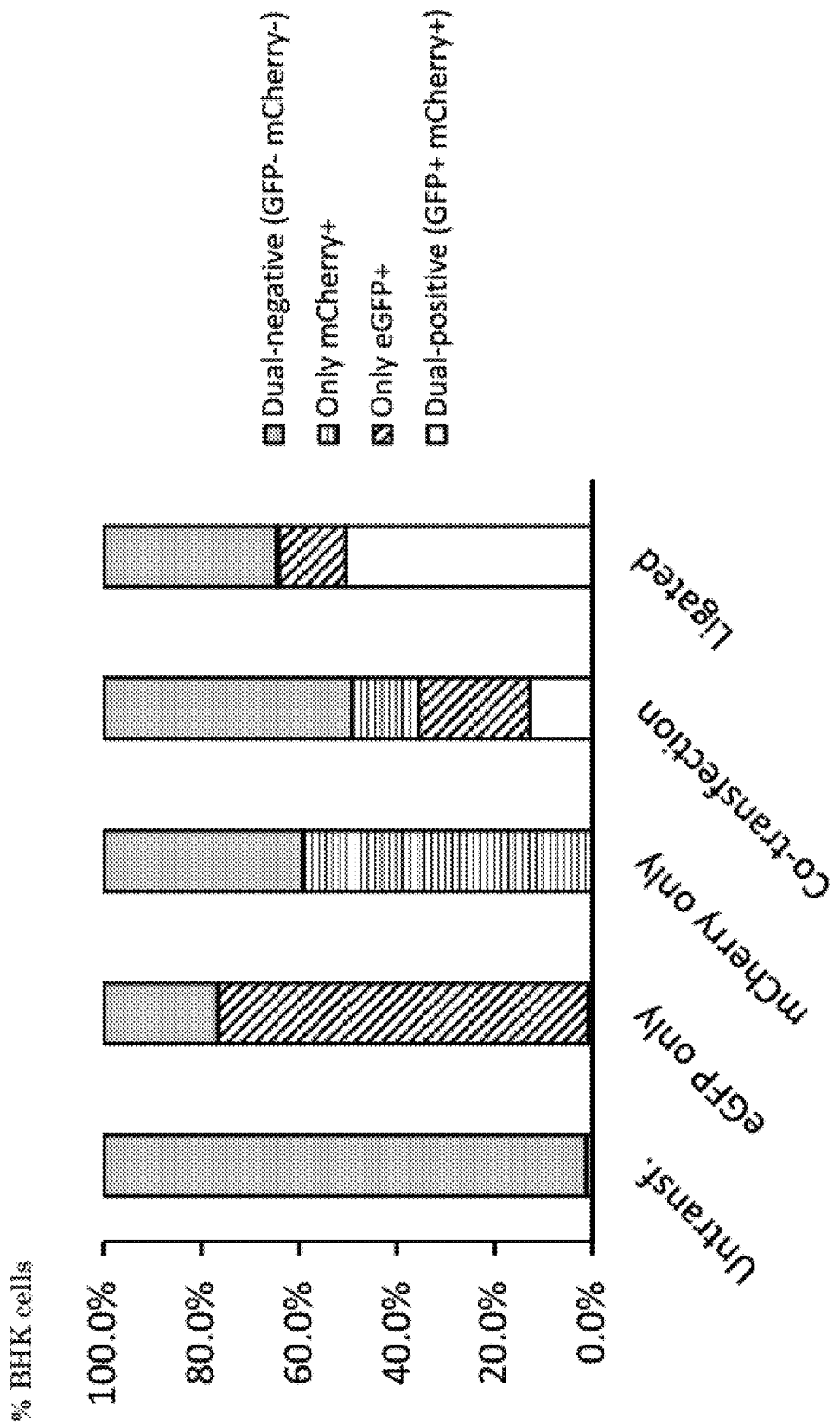

Following the method outlined in Example 3, the two mRNAs were covalently linked via their 3' hydroxyls using the dA6 phospholinker, with formamide denaturing gel analysis confirming generation of the desired dimer based on migration of an RNA of double the size of the monomer in comparison to a linkerless control reaction, which showed only monomeric mRNA. FIG. 5A is a schematic diagram showing creation of an RNA dimer similar to the dimer shown in FIG. 2B but including two different mRNA molecules, one of which encodes the eGFP protein and another one encodes an mCherry fluorescent protein (eGFP-mCherry dimer).

The sequence of the resulting dimer is shown below. In this sequence, the RNA residues (SEQ ID NOs: 3 and 4) are denoted in capital letters and the DNA residues of the phospholinker are underlined small letters. Two RNA/DNA sequences of SEQ ID NOs: 13 and 14 are connected at their 3' end by phosphate "p".

```
                                         (SEQ ID NO: 15)
5' GGGAGACCCAAGCUGCCGCCACCAUGGUGAGCAAGGGCGAGGAGCU

GUUCACCGGGGUGGUGCCCAUCCUGGUCGAGCUGGACGGCGACGUAAAC

GGCCACAAGUUCAGCGUGUCCGGCGAGGGCGAGGGCGAUGCCACCUACG

GCAAGCUGACCCUGAAGUUCAUCUGCACCACCGGCAAGCUGCCCGUGCC

CUGGCCCACCCUCGUGACCACCCUGACCUACGGCGUGCAGUGCUUCAGC

CGCUACCCCGACCACAUGAAGCAGCACGACUUCUUCAAGUCCGCCAUGC

CCGAAGGCUACGUCCAGGAGCGCACCAUCUUCUUCAAGGACGACGGCAA

CUACAAGACCCGCGCCGAGGUGAAGUUCGAGGGCGACACCCUGGUGAAC

CGCAUCGAGCUGAAGGGCAUCGACUUCAAGGAGGACGGCAACAUCCUGG

GGCACAAGCUGGAGUACAACUACAACAGCCACAACGUCUAUAUCAUGGC

CGACAAGCAGAAGAACGGCAUCAAGGUGAACUUCAAGAUCCGCCACAAC

AUCGAGGACGGCAGCGUGCAGCUCGCCGACCACUACCAGCAGAACACCC

CCAUCGGCGACGGCCCCGUGCUGCUGCCCGACAACCACUACCUGAGCAC

CCAGUCCGCCCUGAGCAAAGACCCCAACGAGAAGCGCGAUCACAUGGUC

CUGCUGGAGUUCGUGACCGCCGCCGGGAUCACUCUCGGCAUGGACGAGC

UGUACAAGUAACUAGAGCUGCCUUCUGCGGGCUUGCCUUCUGGCCAUG

CCCUUCUUCUCUCCCUUGCACCUGUACCUCUUGGUCUUUGAAUAAAGCC

UGAGUAGGAAGUGAGGGUAGGGAAAAAAAAAAAAAAAAAAAAAAAAAAA

AAAAAAAAAAAAAAAAAAAAAAAAAAAAAAAAAAAAAAAAAAAAAAAAA

AAAAAAAAAAAAAAAAAAAAAAAAAaaa-3'-p-3'aaaAAAAAAAAAAA

AAAAAAAAAAAAAAAAAAAAAAAAAAAAAAAAAAAAAAAAAAAAAAAAA
```

-continued

```
AAAAAAAAAAAAAAAAAAAAAAAAAAAAAAAAAAAAAAAAAAGGGAUGGGA

GUGAAGGAUGAGUCCGAAAUAAGUUUCUGGUUCUCCAUGUCCACGUUCC

CUCUCUUCUUCCCGUACCGGUCUUCCGUUCGGGGCGUCUUCCGUCGAGA

UCGAUGAACAUGUCGAGCAGGUACGGCGGCCACCUCACCGCCGGGAGCC

GCGCAAGCAUGACAAGGUGCUACCACAUCAGGAGCAACACCCUCCACUA

CAGGUUGAACUACAACUGCAACAUCCGCGCCCGUCGACGUGCCCGAAG

AACCGGAACAUCCACCAGAACUGGAGUCGCAGCAUCACCGGCGGCAGGA

AGUCGAAGUCGGAGACGAACUAGAGCGGGAAGUCCCGCGGCAGGAGCCC

CAUGUAGGCGAGCCUCCUCCGGAGGGUCGGGUACCAGAAGAAGACGUAA

UGCCCCGGCAGCCUCCCCUUCAACCACGGCGCGUCGAAGUGGAACAUCU

ACUUGAGCGGCAGGACGUCCCUCCUCAGGACCCAGUGCCAGUGGUGCGG

CGGCAGGAGCUUCAAGUAGUGCGCGAGGGUGAACUUCGGGAGCCCCUUC

CUGUCGAAGUUCAUCAGCCCCUACAGCCGCCCCACGAAGUGCAUCCGGA

ACCUCGGCAUGUACUUGACUCCCCUGUCCUACAGGGUCCGCUUCCCGUC

CCCCGGUGGGAACCAGUGGAAGUCGAACCGCCAGACCCACGGGAGCAUC

CCCGCCGGGAGCGGGAGCGGGAGCUAGAGCUUGAGCACCGGCAAGUGCC

UCGGGAGGUACACGUGGAACUUCGCGUACUUGAGGAACUACUACCGGUA

CAAUAGGAGGAGCGGGAACGAGUGGUACCACCGCCGUCG

-continued

UGGGCAACCCCGAGUGUGAUCCUCUGCUGCCUGUCAGAUC

CUGGUCCUACAUCGUGGAAACCCCUAACAGCGAGAACGGC

AUCUGCUACCCCGGCGACUUCAUCGACUACGAGGAACUGA

GAGAACAGCUGAGCAGCGUGUCCAGCUUCGAGAGAUUCGA

GAUCUUCCCCAAAGAGAGCAGCUGGCCCAACCACAACACC

AAUGGCGUGACAGCCGCCUGUUCUCACGAGGGCAAGAGCA

GCUUCUACCGGAACCUGCUGUGGCUGACCGAGAAAGAGGG

CAGCUACCCCAAGCUGAAGAACUCCUACGUGAACAAGAAA

GGCAAAGAGGUGCUGGUCCUCUGGGGCAUCCACCAUCCUC

CAAACAGCAAAGAGCAGCAGAACCUGUACCAGAACGAGAA

UGCCUACGUGUCCGUGGUCACCAGCAACUACAACCGGCGG

UUCACACCUGAGAUCGCCGAGAGGCCUAAAGUGCGCGAUC

AGGCCGGCAGAAUGAACUACUACUGGACCCUGCUGAAGCC

CGGCGACACCAUCAUCUUUGAGGCCAACGGCAACCUGAUC

GCCCCUAUGUACGCCUUCGCUCUGAGCAGAGGCUUUGGCA

GCGGCAUCAUCACCUCCAACGCCAGCAUGCACGAGUGCAA

CACCAAGUGUCAGACACCCCUGGGCGCUAUCAACAGCAGC

CUGCCUUACCAGAACAUUCACCCCGUGACCAUCGGCGAGU

GCCCCAAAUACGUCAGAUCCGCCAAGCUGAGAAUGGUCAC

CGGCCUGAGAAACAUCCCCAGCAUCCAGUCCAGAGGCCUG

UUUGGCGCCAUUGCCGGCUUUAUCGAAGGCGGCUGGACCG

GCAUGAUCGACGGAUGGUACGGAUACCACCACCAGAAUGA

GCAAGGCAGCGGCUACGCCGCCGAUCAGAAAAGCACACAG

AACGCCAUCAACGGCAUCACCAACAAAGUGAACACCGUGA

UCGAGAAGAUGAACAUCCAGUUCACCGCCGUGGGCAAAGA

GUUCAACAAGCUGGAAAAACGGAUGGAAAACCUCAACAAG

AAGGUGGACGACGGCUUCCUGGACAUCUGGACCUACAAUG

CCGAGCUGCUCGUGCUCCUGGAAAACGAGAGAACCCUGGA

CUUCCACGACAGCAACGUGAAGAAUCUGUACGAGAAAGUG

AAGUCCCAGCUCAAGAACAACGCCAAAGAGAUCGGCAACG

GCUGCUUCGAGUUCUACCACAAGUGCGACAACGAGUGCAU

GGAAAGCGUGCGGAACGGCACCUACGACUACCCCUAAGUAC

AGCGAGGAAAGCAAGCUGAACCGCGAAAAAGUGGACGGCG

UGAAGCUGGAAUCCAUGGGCAUCUACCAGAUUCUGGCCAU

CUACAGCACCGUGGCCUCUAGCCUGGUGCUUCUGGUUUCU

CUGGGCGCCAUCAGCUUUUGGAUGUGCAGCAAUGGCAGCC

UGCAGUGCCGGAUCUGCAUCUAGAUACAGCAGCAAUGGGC

AAGCUGCUCUAGAGCUGCCUUCUGCGGGGCUUGCCUUCUG

GCCAUGCCCUUCUUCUCUCCCUUGCACCUGUACCUCUUGG

UCUUUGAAUAAAGCCUGAGUAGGAAGUGAGGGGGCGCCAU

UUCAAAAAAAAAAAAAAAAAAAAAAAAAAAAAAAAAAAAA

AAAAAAAAAAAAAAAAAAAAAAAAAAAAAAAAAAAAAAAA

AAAAAAAAAAAAAAAAAAAAAAaaa-3'-p-3'aaaAAA

AAAAAAAAAAAAAAAAAAAAAAAAAAAAAAAAAAAAAAAA

AAAAAAAAAAAAAAAAAAAAAAAAAAAAAAAAAAAAAAAA

AAAAAAAAAAAAAAAAACUUUACCGCGGGGGAGUGAAGGA

UGAGUCCGAAAUAAGUUUCUGGUUCUCCAUGUCCACGUUC

CCUCUCUUCUUCCCGUACCGGUCUUCCGUUCGGGGCGTCT

TCCGTCGAGATCTCGTCGAACGGTTAACGACGACATAAAT

AGTCGAGTAGAGCTCCATCAACTACATGAGAACGTGGGTA

AAGAAGAGCCCCAATCGCGTGTGAACAGACAAGGCAGACC

AGTGCTTGTGGTGCCGGTCCAACGACGTGAACGACGACCA

CATCTTCATGAGAAAGTGCACTCGGGATCCGTCCCGGTCT

CTGTCTATCCGCTTCGTCGTTCCACACCACAGCGACGGCA

TACCTCTTCGACCTCGTCCCCACGTGTCTCGTCGTCGACA

GTCCTACTACCAGTCTCGCCGCCGTCTCTAGAAGTACCAC

CGCCGGATCTGAACCGCCTGATCTGATACAGCATCAGGTA

ATCGAACCCAGAGGG-5'

(SEQ ID NO: 18)

Figure 6A:
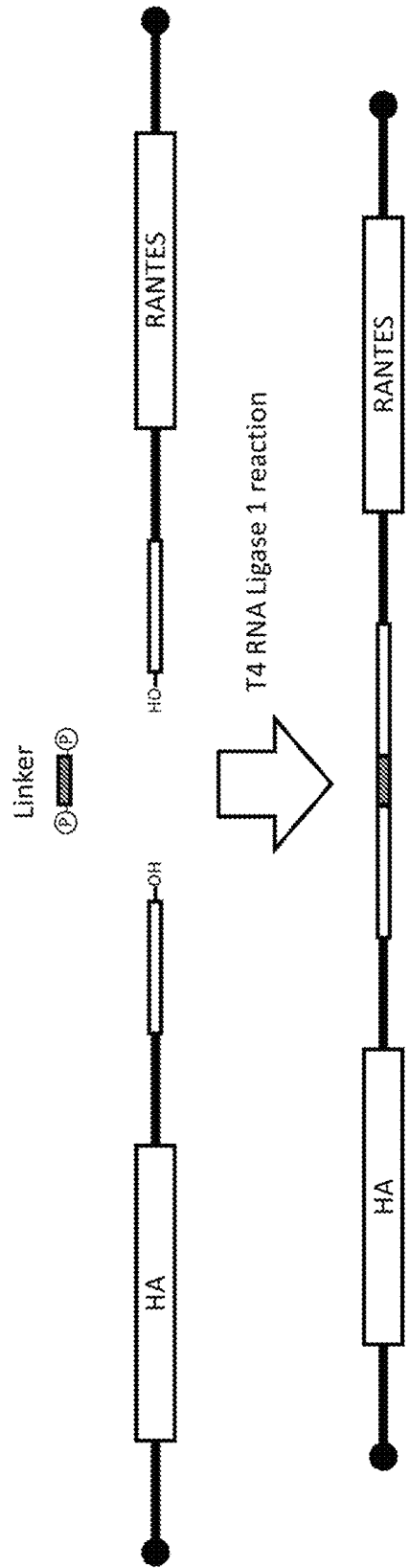
FIGS. 6A-6C illustrate creation of a tail-tail RNA conjugated dimer including two different mRNA molecules, one of which encodes an Influenza strain PR8 hemagglutinin (HA) protein and another one encodes a RANTES protein.
Figure 6B:
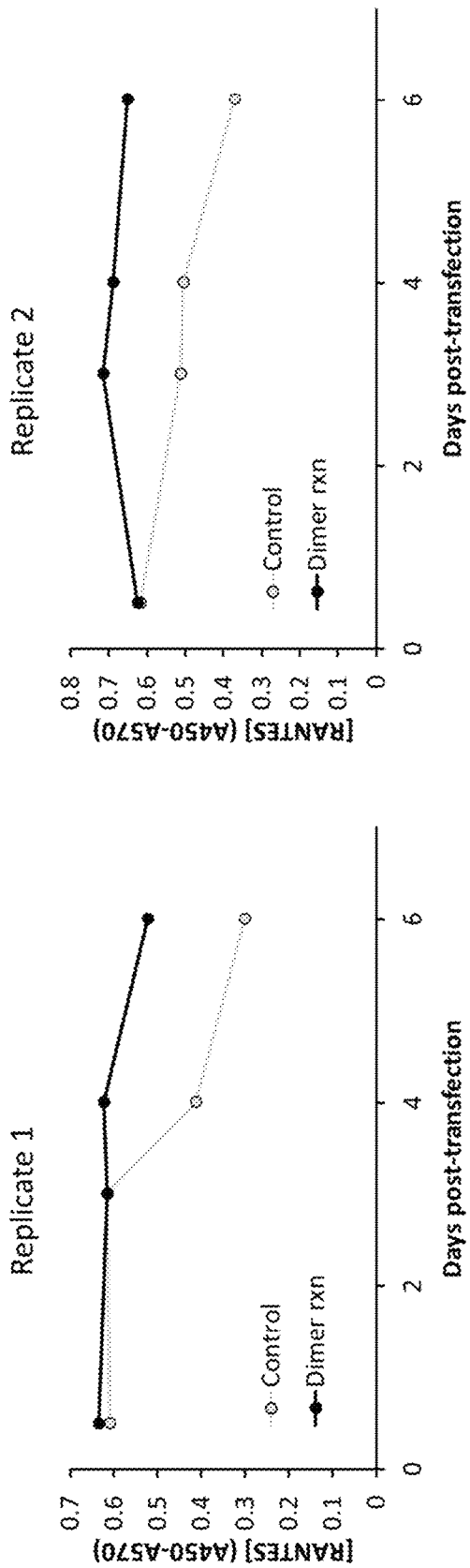
Figure 6C:
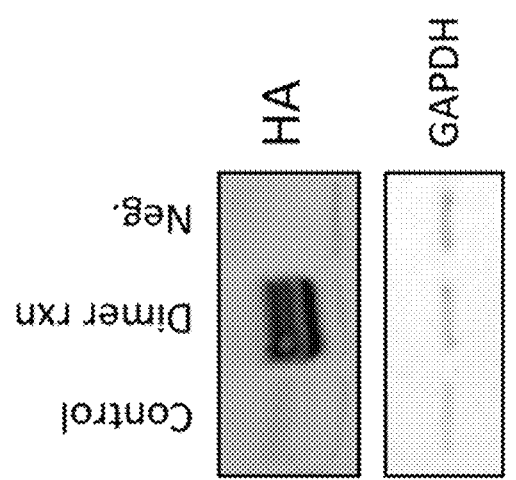

The methods described in Examples 3 and 4 were followed, and BHK cells transfected following the same techniques. On days 4 and 6 after transfection, media was sampled and RANTES concentration measured by sandwich ELISA using a commercial kit (R&D Systems, Inc., Minneapolis, MN, USA). This experiment was conducted in biological duplicate, and the results were analyzed and plotted separately and on day 6 the cell pellets were harvested and PR8 HA protein measured by immunoblot. FIG. 6B are two sets of line graphs Replicate 1 (left) and Replicate 2(right) showing the RANTES expression of the HA-RANTES RNA dimer (Dimer rxn) in baby hamster kidney (BHK) cells measured 2, 4 and 6 days post transfection compared to control monomer mRNA (control). FIG. 6C is a photograph of an immunoblot that shows the greater HA expression for the HA-RANTES RNA dimer (Dimer rxn) than for the control unligated RNA (Control) and culture medium (Neg.)

The RANTES concentration in culture media was better sustained by the tail-to-tail conjugated mRNA: by day 6, in one replicate of the experiment the HA-RANTES mRNA dimer expressed RANTES at a value 1.74×higher than control unligated mRNAs, and in the second replicate the value was similar with 1.76×greater expression. The phenomenon also held true for HA expression: the day 6 immunoblot showed greater HA expression by the cells for the tail-to-tail dimer than the control unligated mRNA mixture.

Example 7. Linker to Attach More than Two mRNAs by their 3' Ends

This disclosure has demonstrated means of attaching two mRNAs tail-to-tail, for example by using a short nucleotide linker bearing two single-stranded nucleic acid 5' ends, and demonstrated the increased potency and longevity of gene expression produced by these products. It would be useful in certain cases if more than two mRNAs could be ligated similarly by their 3' hydroxyl groups, as each mRNA conjugate could potentially carry 3, 4, or more distinct protein coding sequences and thus mediate more complex processes inside a cell. The production of, for example, a tetrameric mRNA (four mRNA molecules conjugated together by their 3' ends) can be performed by the same RNA ligase 1 reactions described above (see Examples 3-5) if, instead of a linker presenting two 5' nucleic acid ends, a linker presenting four 5' nucleic acid ends was used. FIGS. 7A-7D illustrate creation of a linker that can be used for generation of a tail-tail RNA conjugated tetramer including four mRNA molecules.

Figure 7A:
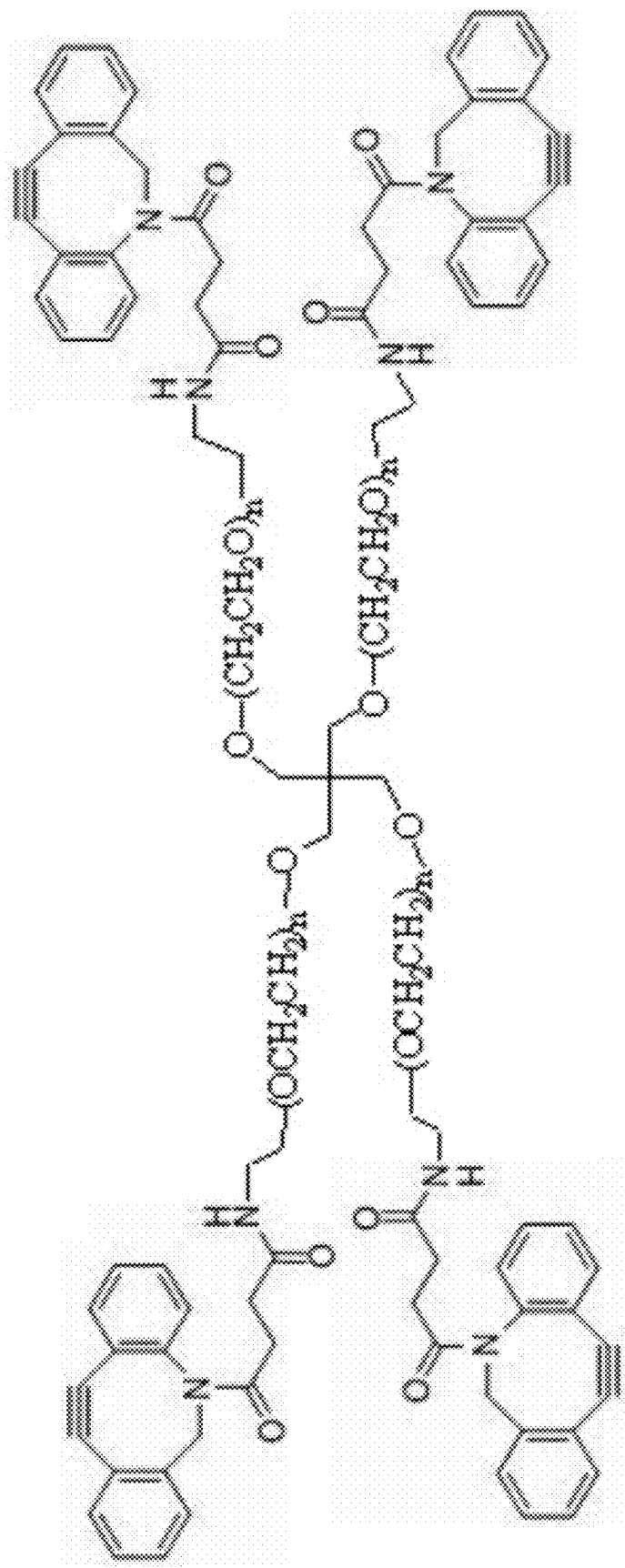
FIGS. 7A-7D illustrate creation of a linker that can be used for generation of a tail-tail RNA conjugated tetramer including four mRNA molecules.
Figure 7B:
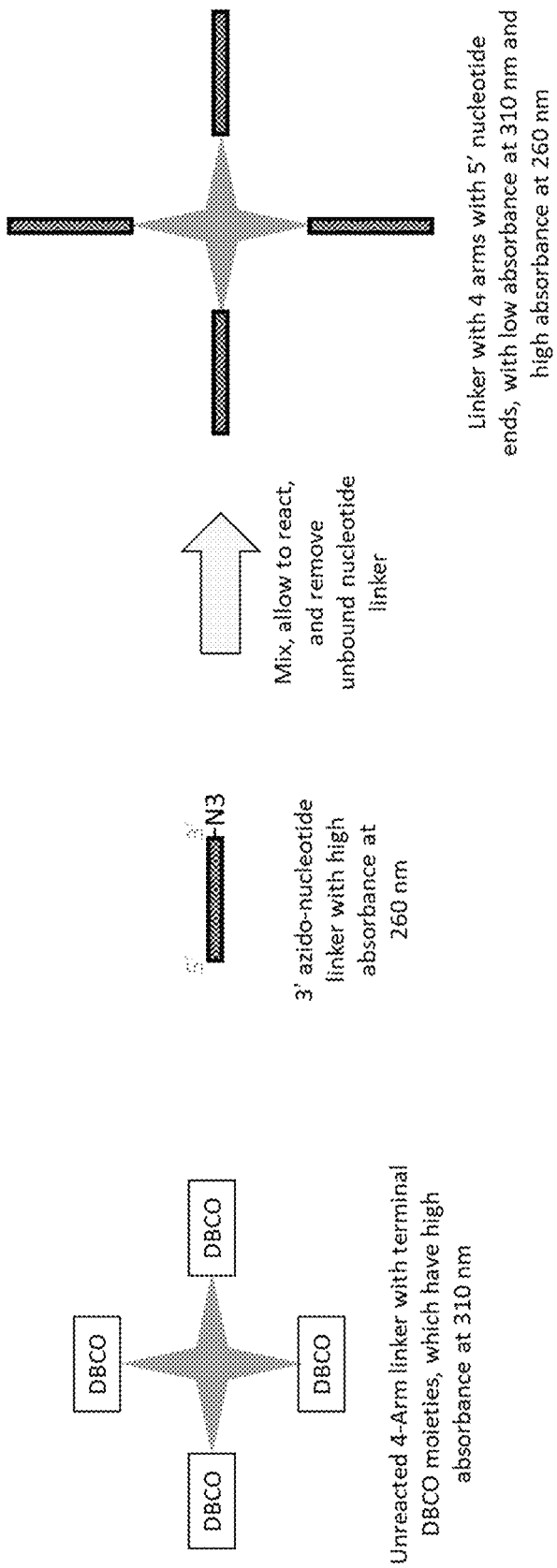
Figure 7C:
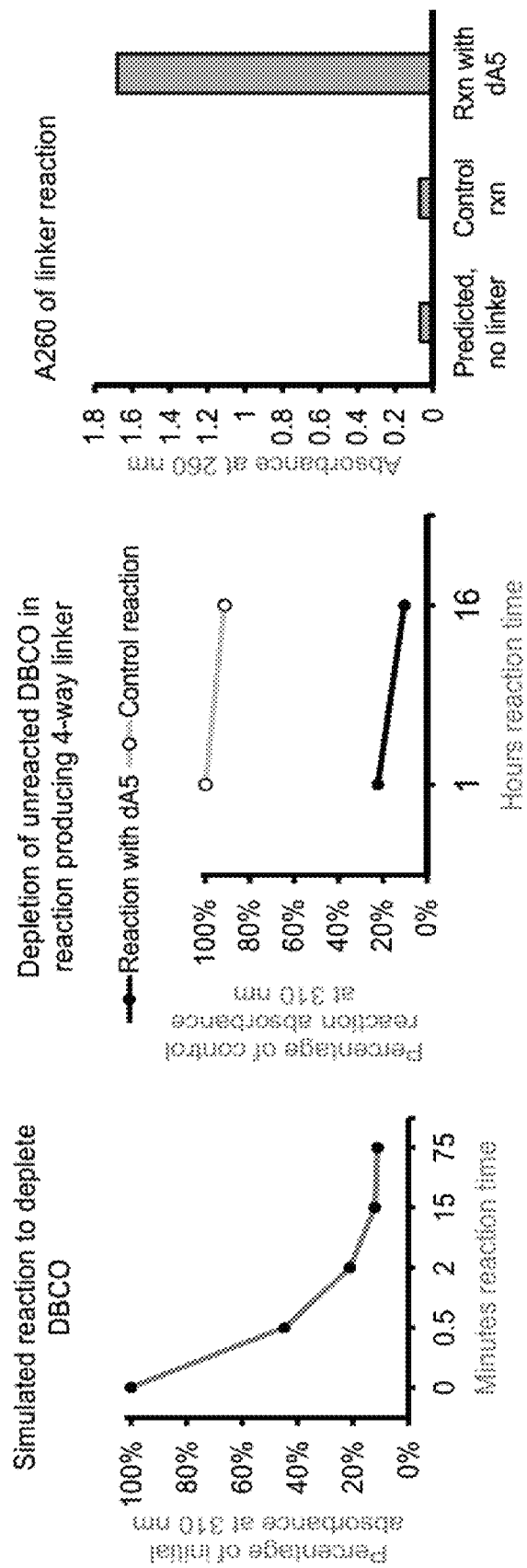
Figure 7D:
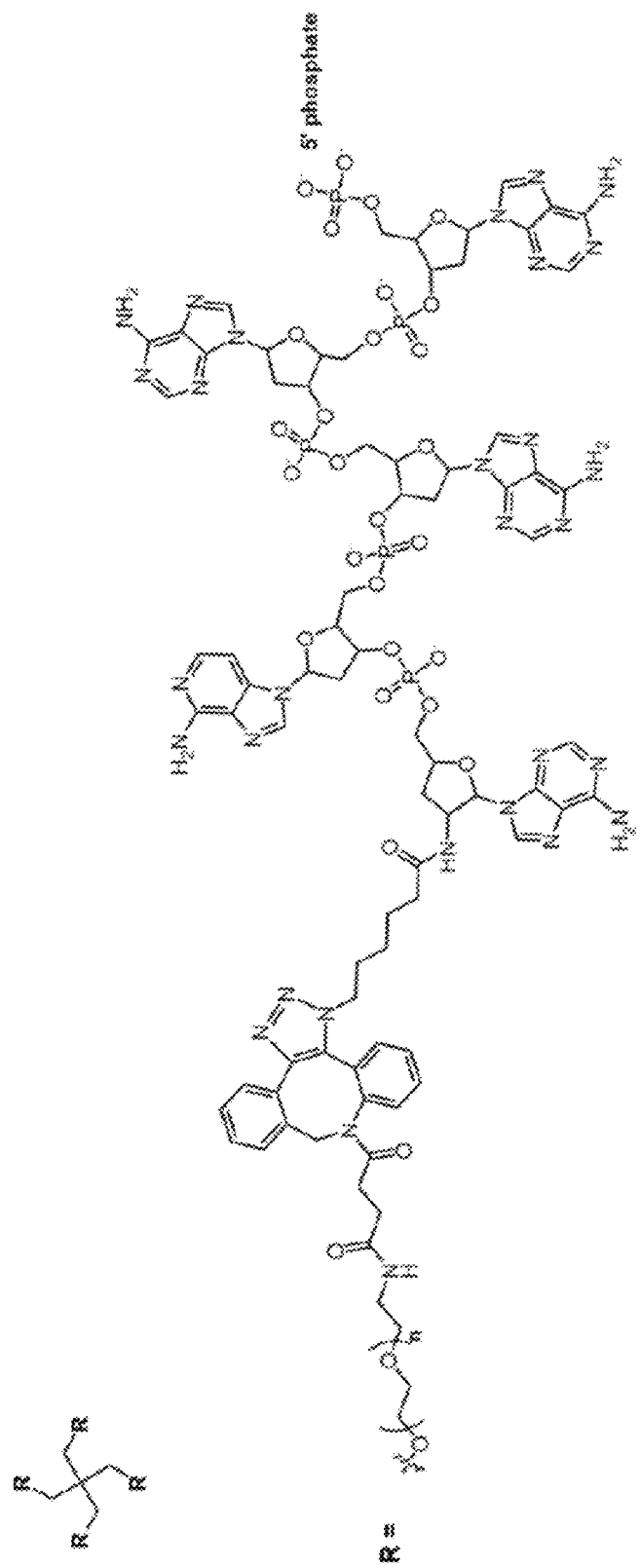

To produce such an exemplary linker, a four-directional branched PEG, terminated with dibenzocyclooctyne (DBCO) reactive groups (4-Arm PEG-DBCO, Creative PEGWorks, Chapel Hill, NC, USA), of 10 kDa nominal molecular weight was used as a starting material for synthesis. FIG. 7A is a structure of a four-directional branched PEG-dibenzocyclooctyne (DBCO) linker. A short custom nucleotide linker was commercially synthesized (Integrated DNA Technologies, Inc., Coralville, IA, USA), consisting of five dA residues in typical 5-3' sequence connected by phosphodiester bonds. The $5^{th}$ dA residue's 3' position carried a C5 linker terminated with an azide group, connected to the dA 3' via a peptide bond (resulting from NHS ester coupling). This nucleotide linker is henceforth referred to as a "dA5 azidolinker". This custom nucleic acid linker was mixed with the 4-Arm PEG-DBCO compound in molar excess to perform a strain-promoted azide-alkyne click chemistry (SPAAC) reaction. The reaction is illustrated, generically, in FIG. 7B. Briefly, 150 pmol of the 4-Arm PEG-DBCO was mixed in water with 16-fold excess (2.4 nmol) of the dA5 azidolinker, and the reaction monitored by measuring optical absorbance at 310 nm (which detects unreacted DBCO moieties due to the compound's distinctive, highly delocalized pi-electron system). The presence of dA5 azidolinker in the reaction was detected by the characteristic absorbance at 260 nm typical of all nucleic acids. To confirm that the absorbance measurement was an accurate reporter of reaction progression, a simulation of the reaction was carried out in parallel on 20 µl of a 4.6 mg/ml aqueous solution of 4-Arm PEG-DBCO by adding 0.5 µl of 43 mg/ml $NaN_3$ solution. DBCO reacts in the presence of the free azide in the same matter as it reacts in the cycloaddition reaction with the intended dA5 azidolinker. Before addition of $NaN_3$, the absorbance at 310 nm (A310) of the solution as measured by UV-Vis spectrometry was 19.9. Immediately the A310 dropped to 8.9, and after ~2 min it had further dropped to 4.2. By 15 min after $NaN_3$ addition, it had reached 2.4. After an additional 1 hr it had dropped to 2.2, and after further room-temperature incubation overnight (~16 hours) it remained at ~2.2. Therefore, the bottoming-out of the A310 reading to a floor of about 9-fold lower than the initial reading indicates progression of the cycloaddition to completion. In the reaction of the 4-Arm PEG-DBCO with the dA5 azidolinker, after 1 hr reaction at room temperature the A310 was 0.26, compared to an equivalent control reaction that was identical but lacked the dA azidolinker that exhibited an A310 value of 1.17. This ~4.5-fold drop in A310 suggested that the reaction was proceeding but was incomplete. The reaction was allowed to incubate overnight (~16 hours) at room temperature, and an A310 value of 0.11 was measured (compared to 1.07 for the negative control reaction). This 9.7-fold reduction in A310 indicates that the reaction had proceeded to completion. Buffer exchange was performed using a 3 kDa polyethersulfone (PES) Concentrator (Thermo Fisher Scientific, Waltham, MA, USA) by performing sequentially a first 40× and second 5× buffer changes, resulting in a 200× depletion of reaction components under the 3 kDa molecular weight cutoff. As the free dA azidolinker is ~1.8 kDa, only ~0.5% residual linker would remain. The A260 of a control solution of the dA azidolinker equivalent to the original reaction concentration was 13.31, and after 1:200 dilution would give a theoretical A260 value of 0.067. After the 200× buffer exchange however, the 4-Arm PEG-DBCO+dA5 azidolinker reaction A260 value was 1.68, which was ~25-fold higher than the theoretical A260 if no conjugation had occurred. This indicates that the dA5 nucleic acid segregated with and was therefore linked to the 4-Arm PEG-molecule. For comparison, the negative control reaction without conjugated dA5 yielded an A260 of only 0.07. The process and absorbance values illustrating the successful conjugation of the dA5 linker to the 4-Arm PEG are summarized in FIGS. 7B and 7C. FIG. 7C are line and bar graphs showing absorbance values illustrating the successful conjugation of the dA5 linker to the 4-Arm PEG as shown in FIG. 7B. The line graph on the left show absorbance at the simulated reaction to deplete DBCO; the line graph in the middle show absorbance at the depletion of unreacted DBCO in reaction producing 4-way linker (close circles represent reaction with dA5, and open circles represent control reaction); and the bar graph on the right shows absorbance at OD260 of the reaction with dA5 (dA5rxn) compared to control reaction (control rxn) and predicted reaction with no linker (predicted no linker). This 4-way linker can be phosphorylated by standard polynucleotide kinase reactions to phosphorylate the four 5' nucleotide ends per molecule. FIG. 7D is a generic structure of a 4-way linker obtained by this process is illustrated in FIG. 7B.

Example 8. Production of 3-, 4-, and 8-Way Tail-Conjugated mRNAs

Following the methods described above, an mRNA multimer is assembled by chemical ligation of their 3' hydroxyl groups to a 3-way, 4-way, or 8-way linker. FIGS. 8A-8D are structures of 3-, 4-, and 8-arm linkers.

Figure 8A:
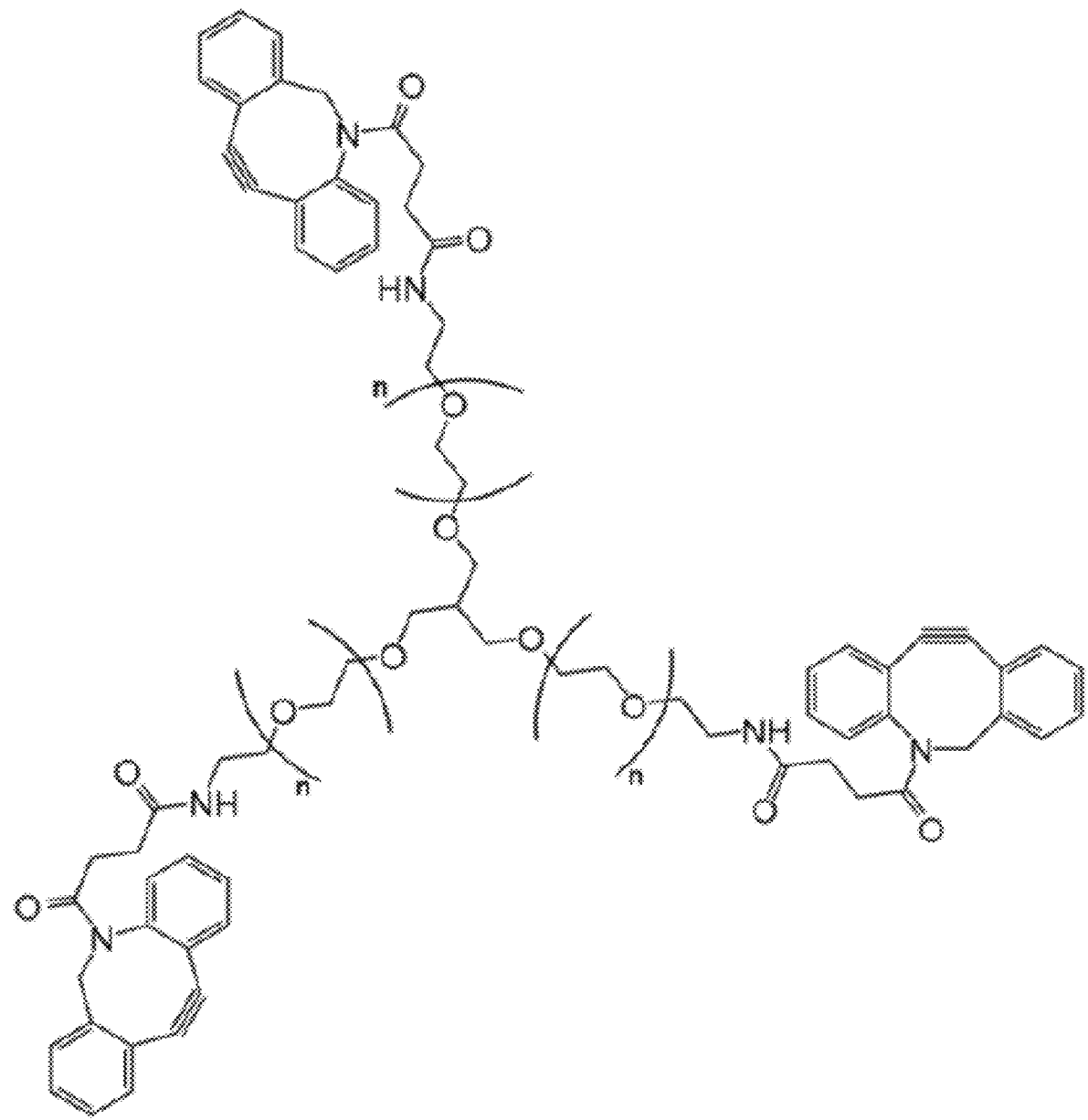
FIGS. 8A-8D are structures of 3-, 4-, and 8-arm linkers.
Figure 8B:
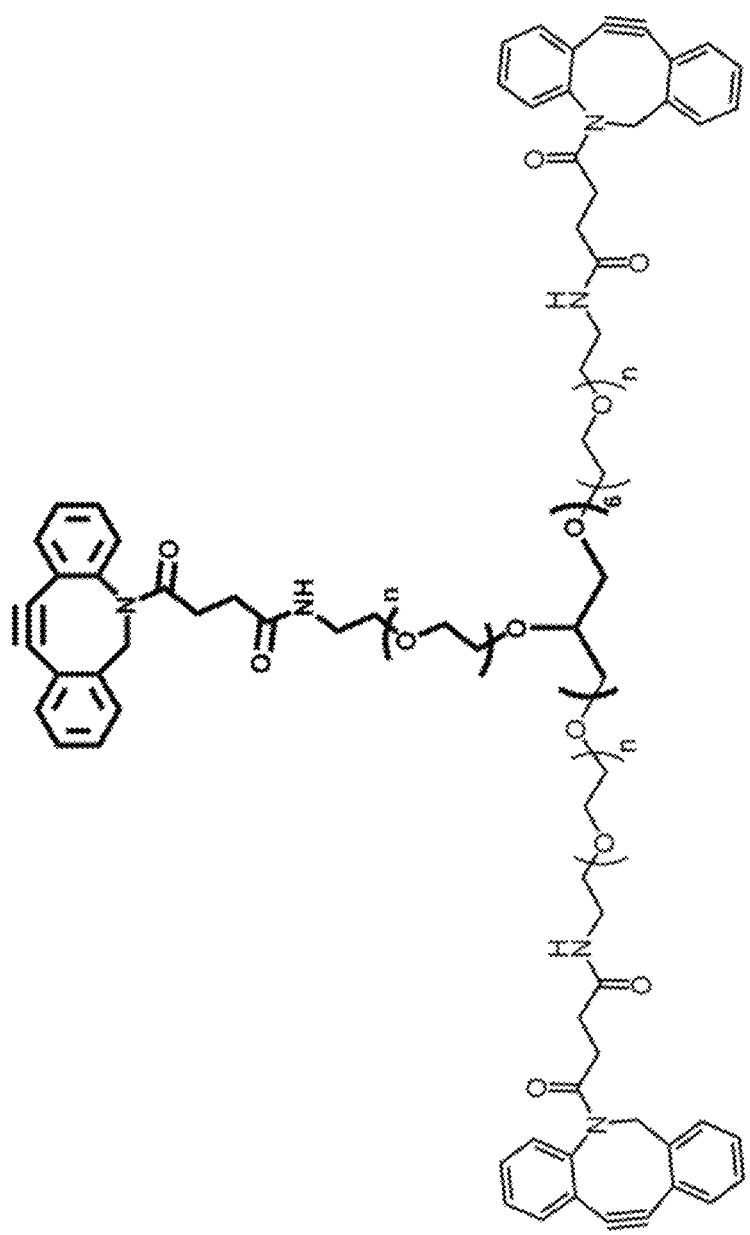
Figure 8C:
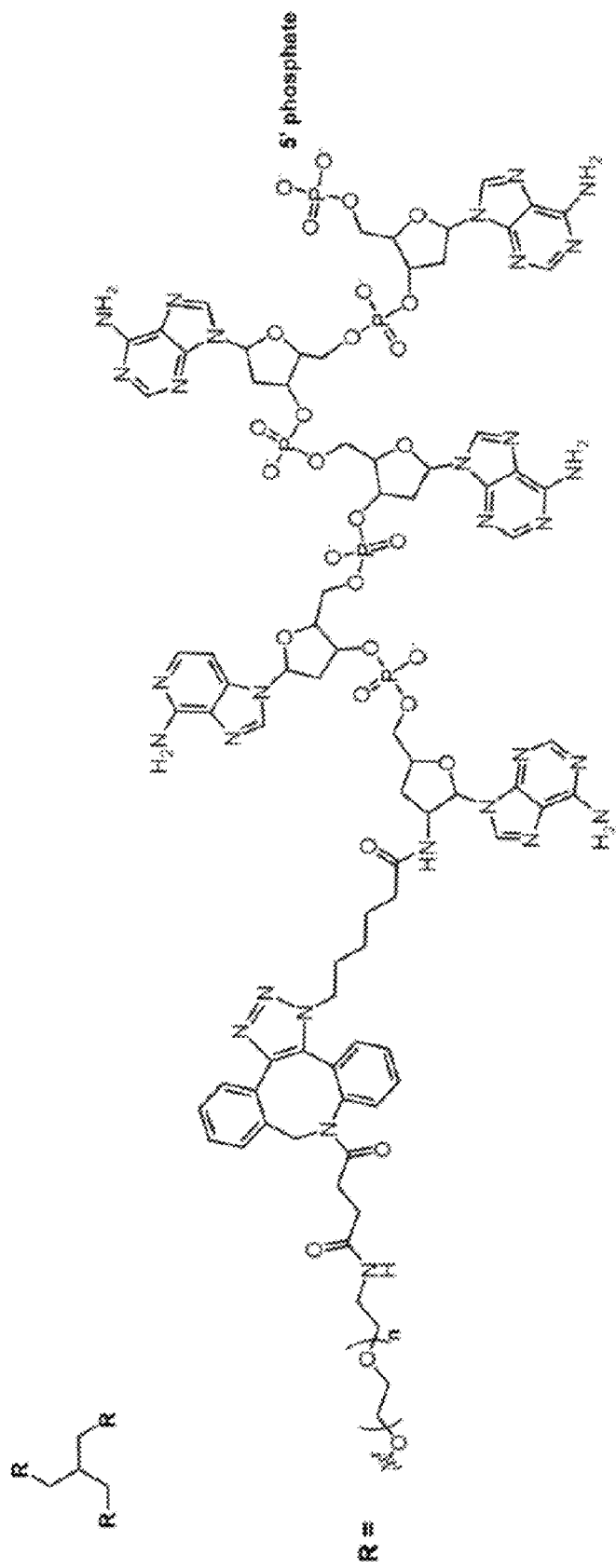
Figure 8D:
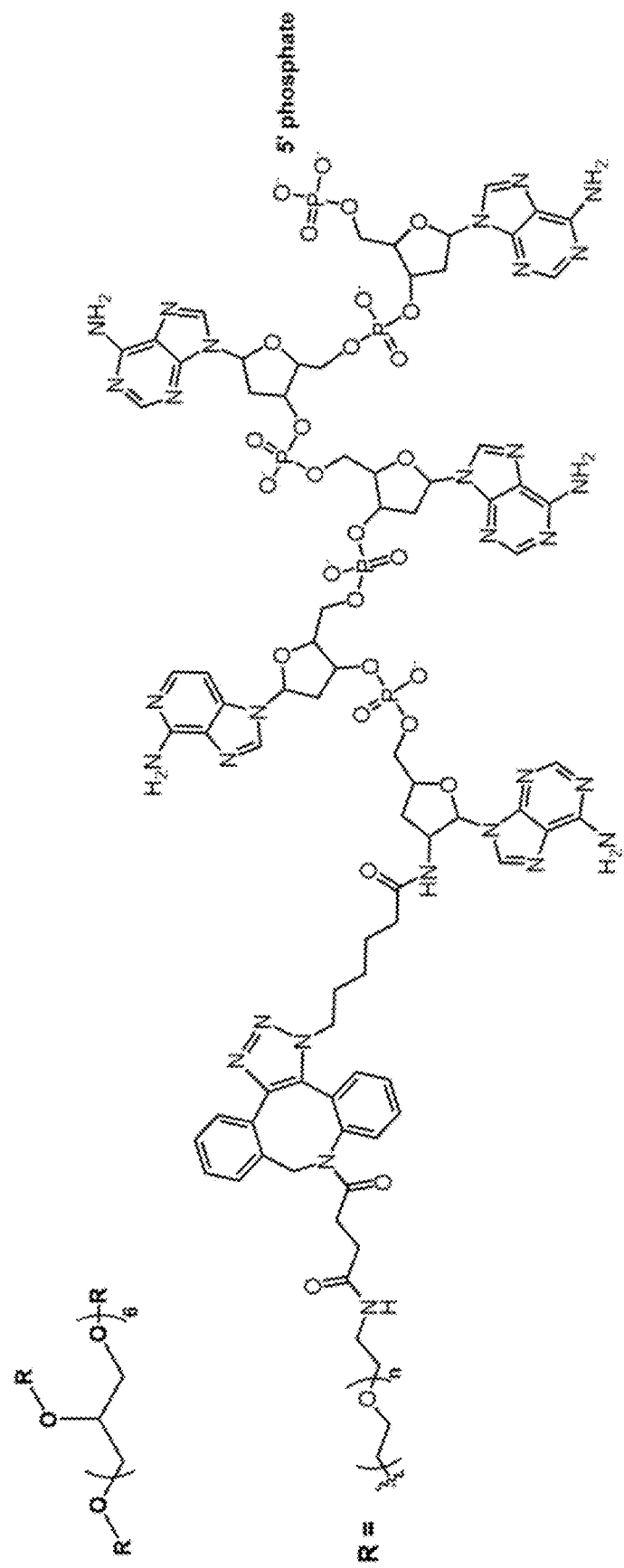

FIG. 8A is a structure of the 3-Arm PEG-DBCO that serves as the starting material to produce the 3-way tail-conjugated mRNA. FIG. 8B is a structure of an 8-Arm PEG-DBCO at serves as the starting material to produce the 8-way tail-conjugated mRNA. In this structure, the internal branch is repeated six times (and is shown in bold) The 4-Arm starting material is set forth in Example 7, as shown in FIG. 7A. These starting materials are available commercially. The DBCO-terminated PEG linkers are mixed with the short custom dA5 azidolinker detailed in Example 7. The dA5 azidolinker is mixed with 150 pmol of the branched PEG-DBCO molecule desired, in a 12-fold molar excess for the 3-Arm PEG-DBCO, and in a 32-fold molar excess for the 8-Arm PEG-DBCO. The SPAAC reaction is incubated overnight (~16 hrs) at room temperature, with reaction progress monitored by reduction in A310 to indicate depletion of unreacted DBCO moieties. The final product is purified by buffer exchange across a 3 kDa molecular weight cut-off filter (by spin concentrator or dialysis) to remove the excess unreacted dA5 azidolinker. The resulting linker carries 5' nucleic acid ends for ligation to the 3' hydroxyl groups of mRNA. As with the 4-way linker described in Example 7, the linkers' 5' ends are phosphorylated by incubation of 300 pmol of linker in an aqueous reaction containing 70 mM Tris-HCl (pH 7.6), 10 mM $MgCl_2$, 5 mM DTT, 1 mM ATP, and 10 units of T4 Polynucleotide Kinase enzyme (New England Biolabs, Inc., Ipswich, MA, USA) in 50 µl final volume at 37° C. for 1 hr before enzyme inactivation by incubation at 65° C. for 20 min and buffer exchange exactly as described above. Alternatively, the custom dA azidolinker can be synthesized to carry a 5' monophosphate group commercially and used in this form for SPAAC reaction under identical conditions to skip the phosphorylation step if desired. The resulting ligation-ready 3-way, 4-way, and 8-way linkers are shown in FIGS. 8C, 7D, and 8D respectively. FIG. 8C is a structure of a 3-way linker bearing three terminal nucleotide 5' phosphate groups. FIG. 8D is a structure of an 8-way linker bearing eight terminal nucleotide 5' phosphate groups.

Alkaline phosphatase-treated mRNA molecules are covalently attached by their 3' hydroxyl groups to the linkers by T4 RNA ligase 1 reaction following the reaction conditions specified in Example 3. Briefly, 10-20 pmol of mRNA is reacted in 20 µl of a T4 RNA Ligase 1 reaction mixture containing 50 mM Tris-HCl, pH 7.5, 10 mM MgCl$_2$, 1 mM DTT, 10% PEG8000, 1 mM ATP, and 30 units of T4 RNA Ligase 1 (New England Biolabs, Inc., Ipswich, MA, USA) with x pmol of the multi-directional linker of interest, where x is the number of pmols of mRNA divided by the number of termini on the linker of interest. For example, 18 pmol of mRNA is reacted with 6 pmol of the 3-way linker. The reaction progress is monitored by formamide denaturing agarose gel electrophoresis, and carried out typically overnight at 16° C. The desired high-mass product is purified by standard chromatography methods. Different mRNA molecules may be reacted to produce heterogenous multi-arm conjugates, with the molar ratio of different input mRNAs determining the average stoichiometric ratio of conjugated mRNA species per multi-arm tail-tail conjugate product.

Figure 9A:
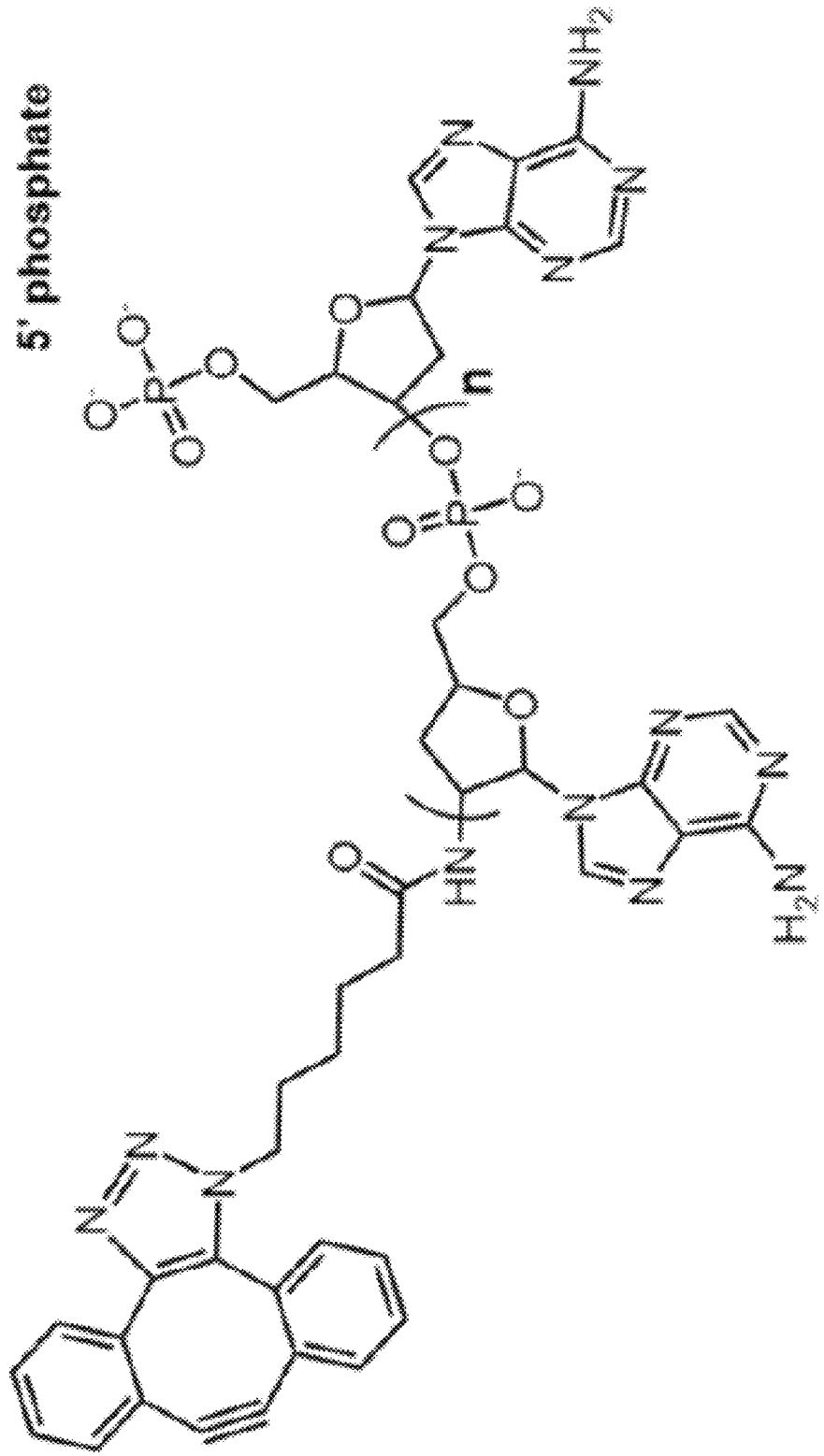
FIGS. 9A-9B illustrate creation of tail-tail RNA conjugates by click chemistry.
Figure 9B:
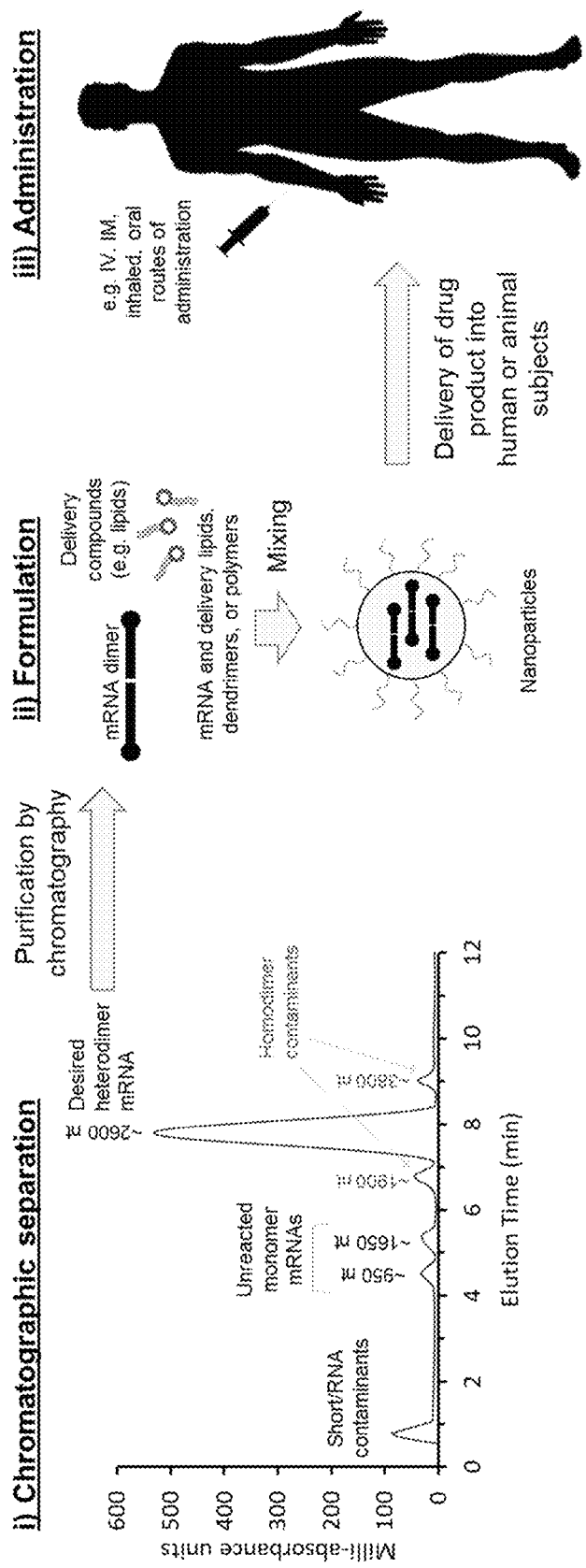

Example 9. Two Different mRNA Molecules Conjugated Tail-to-Tail by Click Chemistry The specificity and bio-orthogonality of click reactions permits the expedient ligation of two different nucleic acid molecules to produce a single desired dimer species. FIGS. 9A-9B illustrate creation of tail-tail RNA conjugates by click chemistry. This is especially useful in the context of expressing therapeutic monoclonal antibodies, the production of which relies on efficient equimolar co-expression of heavy chain polypeptide (HC; SEQ ID NO: 21) and light chain polypeptide (LC; SEQ ID NO: 22) that must fold together into a functional heterotetramer composed of two HC-LC heterodimers. The HER2-specific monoclonal antibody trastuzumab, which is used in the treatment of HER2-positive breast cancer, is an exemplary antibody that may be encoded as heterodimeric 3' tail-linked mRNA to mediate expression in vitro or directly in a patient. mRNAs encoding the HC (SEQ ID NO: 19) and LC (SEQ ID NO: 20) are synthesized and sourced by standard commercial in vitro transcription (IVT). The 3' ends of the mRNAs are functionalized by enzymatic incorporation of a chemically modified nucleic acid. T4 RNA Ligase 1 reaction (as described in Examples 3-5) is performed on the HC mRNA in the presence of a 10-fold molar excess of pCp-Azide (Jena Bioscience GmbH) as the 5' phosphate donor to produce mRNA carrying a 3' terminal azide moiety. The LC mRNA is treated in a separate T4 RNA Ligase 1 reaction in the presence of a custom dA15 oligo bearing a 3' dibenzocyclooctyne (DBCO) moiety, obtained commercially (Integrated DNA Technologies, Inc., Coralville, IA, USA) in 10-fold molar excess. FIG. 9A is a structure of a 3' dibenzocyclooctyne (DBCO) moiety-containing nucleotide molecule bearing a 5' phosphate group. The value of n is 0 to 30; if n is 0, it is referred to as a mononucleotide. This produces mRNA carrying a 3' terminal DBCO moiety. The functionalized mRNAs are purified by standard LiCl precipitation to eliminate enzymatic and small molecule reaction components. The functionalized HC and LC mRNAs are mixed in H2O at a 1:1 molar ratio at a final mRNA concentration of ~1 mg/ml in 500 µl final volume, and allowed to incubate at 4-16° C. overnight (~16 hrs) to allow completion of the SPAAC reaction. The reaction progress is monitored by drop in A310 to indicate loss of the unreacted DBCO moieties, and by denaturing formamide agarose gel electrophoresis to quantify the concentration of unreacted mRNA HC and LC monomers (respectively, 1652 and 950 nt in length), and of the heterodimer (~2600 nt in length) based on migration. Any unreacted monomers, or aberrant homodimers of HC and LC mRNA are easily removed by their distinctively different lengths from the desired nt product by conventional SEC, or reversed-phase chromatography using a CIMmultus SDVB column (running conditions 65° C.; equilibration/wash buffer 0.1 M triethylaminoacetate, pH 7.0; elution buffer 0.1 M triethylaminoacetate, 25% acetonitrile, pH 7.0). The HC+LC mRNA heterodimer is then encapsulated in a carrier such as a lipid nanoparticle (LNP) or dendritic or polymeric nanoparticle formulation using standard methods and given to a patient with HER2-positve tumors by an acceptable route of administration. The mRNA dimer enters patients' cells and drives transcription of both HC and LC at similar rates of translational initiation due to the absolute presence of both transcripts upon uptake of the particles by the cell, promoting more efficient trastuzumab generation than if the mRNAs were delivered separately and thus in a stoichiometrically uncontrolled manner. Expression of trastuzumab in the body then binds to HER2 on cancer cells and inhibits tumor growth, and promotes clearance of the cancer. FIG. 9B illustrates a method of purifying and applying a dimeric mRNA encoding an exemplary monoclonal antibody, trastuzumab. The steps indicated are i) purification of the desired HC+LC mRNA heterodimer from any minor contaminating monomeric or homodimeric mRNA species based on size (e.g., reversed-phase chromatography), ii) formulation of the mRNA dimer using ionizable lipids, dendrimers, or polymers to produce a nanoparticle suspension, and iii) administration of the suspension to human or animal subjects to prevent or treat a disease state.

Example 10. Nanoparticle Formulation of Tail-Tail mRNA Dimers

Tail-tail conjugated mRNAs will be useful to mediate a desired biological effect in a human or animal subject with the goal of preventing or treating disease. To effectively deliver such an mRNA conjugate to cells in vivo, the products of the conjugations described above can be encapsulated in a delivery formulation to produce nanoparticles capable of promoting cellular uptake and gene expression.

FIG. 10 illustrates methods of preparing compositions that include nanoparticles and tail-tail RNA conjugates disclosed herein. An example of a composition of heterodimeric mRNA (described in Example 4) encapsulated in nanoparticle form was produced by mixing 6 µg of SEAP-Luc dimerized mRNA in aqueous solution (10 mM sodium acetate buffer, pH 4.5) with an ethanol solution containing 1.5 µg of 1,2-dimyristoyl-rac-glycero-3-methoxypolyethylene glycol-2000 (DMG-PEG2000; Avanti Polar Lipids, Birmingham, AL, USA) and 20 µg of a proprietary ionizable biodegradable dendrimer delivery compound (Tiba Biotech, LLC, Cambridge, MA, USA). The volumetric ratio of the aqueous to ethanol phases was 3:1. The mixture was immediately diluted 1:1 with H2O, and 10 µl of the mixture was analyzed by dynamic light scattering (DLS) in a Malvern ZetaSizer Nano ZS. The DLS profiles are shown in FIG. 10A. FIG. 10A is the dynamic light scattering profile of nanoparticles generated from dimerized mRNA encoding SEAP on the first mRNA and Luciferase on the second mRNA. The data depicts the particle size distribution, and the results of three separate read cycles on a Malvern Zetasizer Nano ZS are shown. Based on three repeat reads of the sample, nanoparticles were present as a monodisperse suspension with Z-average diameter of 158.7 nm, and polydispersity index (PDI) of 0.101. The diameter below 200 nm enables sterile filtration of the particles through a standard 0.2 µm filter, and the PDI is well below generally accepted quality thresholds for nanoparticulate drugs (<0.2) and is ready to administer to a subject's cells in vitro or in vivo.

REFERENCES

Bar-On et al. 2020, SARS-COV-2 (COVID-19) by the numbers, eLife; 9: e57309.

Bergstrom (2009) Current Protocols in Nucleic Acid Chemistry Suppl. 37 1.4.1.

Heyes et al. (2005) J Controlled Release 107:276-87.

Hirao et al (2012) Accounts of Chemical Research vol 45 page 2055.

Worner et al. 2020, Adeno-associated virus capsid assembly is divergent and stochastic, bioRxiv WO2015149077A1, published 2015.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

```

What is claimed is:

1. A tail-tail RNA conjugate comprising two RNA molecules, each of which comprises operably connected elements comprising: a 5' untranslated region (UTR), a coding region, a 3' UTR, and a terminal 3' nucleotide, wherein one RNA molecule comprises the sequence of SEQ ID NO: 5, and another RNA molecule comprises the sequence of SEQ ID NO: 6, and each RNA molecule is connected to one another through the terminal 3' nucleotide.

* * * * *

SEQUENCE LISTING

Sequence total quantity: 22
SEQ ID NO: 1            moltype = RNA  length = 1835
FEATURE                 Location/Qualifiers
source                  1..1835
                        mol_type = other RNA
                        organism = synthetic construct
SEQUENCE: 1
gggagaccca agctaatgga ctacgacata gtctagtccg ccaagtctag gccgccacca    60
tgctggggcc ctgcatgctg ctgctgctgc tgctgctggg cctgaggcta cagctctccc   120
tgggcatcat cccagttgag gaggagaacc cggacttctg gaaccgcgag gcagccgagg   180
ccctgggtgc cgccaagaag ctgcagcctg cacagacagc cgccaagaac ctcatcatct   240
tcctgggcga tgggatgggg gtgtctacgg tgacagctgc caggatccta aaagggcaga   300
agaaggacaa actggggcct gagataccc ctggccatgga ccgcttccca tatgtggctc   360
tgtccaagac atacaatgta gacaaacatg tgccagacag tggagccaca gccacggcct   420
acctgtgcgg ggtcaagggc aacttccaga ccattggctt gagtgcagcc gcccgcttta   480
accagtgcaa cacgacacgc ggcaacgagg tcatctccgt gatgaatcgg gccaagaaag   540
cagggaagtc agtgggagtg gtaaccacca cacgagtgca gcacgcctcg ccagccggca   600
cctacgccca cacggtgaac cgcaactggt actcggacgc cgacgtgcct gcctccgccc   660
gccaggaggg gtgccaggac atcgctacgc agctcatctc caacatggac attgacgtga   720
tcctaggtgg aggccgaaag tacatgtttc gcatgggaac cccagaccct gagtacccag   780
atgactacag ccaaggtggg accaggctgg acgggaagaa tctggtgcag gaatggctgg   840
cgaagcgcca gggtgcccgg tatgtgtgga accgcactga gctcatgcag gcttccctgg   900
acccgtctgt gacccatctc atgggtctct ttgagcctgg agacatgaaa tacgagatcc   960
accgagactc cacactggac ccctcccctga tggagatgac agaggctgcc ctgcgcctgc  1020
tgagcaggaa cccccgcggc ttcttcctct tcgtggaggg tggtcgcatc gaccatggtc  1080
atcatgaaag cagggcttac cgggcactga ctgagacgat catgttcgac gacgccattg  1140
agagggcggg ccagctcacc agcgaggagg acacgctgag cctcgtcact gccgaccact  1200
cccacgtctt ctccttcgga ggctacccc tgcgagggag ctccatcttc gggctggccc  1260
ctgccaaggc ccgggacagg aaggcctaca cggtcctcct atacggaaac ggtccaggct  1320
atgtgctcaa ggacggcgcc cggccggatg ttaccgagag cgagagcggg agccccgagt  1380
atcggcagca gtcagcagtg cccctggacg aagagaccca cgcaggcgag gacgttggcg  1440
tgttcgcgcg cggcccgcag gcgcacctgg ttcacggcgt gcaggagcag accttcatag  1500
cgcacgtcat ggccttcgcc gcctgctgg agccctacac cgcctgcgac ctggcgcccc  1560
ccgccggcac caccgacgcc gcgcaccgg ggtgaataca gcagcaattg gcaagctgct  1620
ctagagctgc cttctgcggg gcttgccttc tggccatgcc cttcttctct ccctttgcacc  1680
tgtacctctt ggtctttgaa taaagcctga gtaggaagtg aggggcgcc atttcaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaa                              1835

SEQ ID NO: 2            moltype = RNA  length = 1958
FEATURE                 Location/Qualifiers
source                  1..1958
                        mol_type = other RNA
                        organism = synthetic construct
SEQUENCE: 2
gggagaccca agctaatgga ctacgacata gtctagtccg ccaagtctag gccgccacca    60
```

```
tggaagatgc caagaacatc aagaagggcc ctgctccatt ctaccctctg gaagatggaa    120
cagccggcga gcagctgcac aaggccatga agagatacgc tctggtgccc ggcacaatcg    180
ccttcacaga tgctcacatc gaggtggaca tcacctacgc cgagtacttc gagatgtctg    240
tgcggctggc cgaagctatg aagcgctacg gcctgaacac caaccacaga atcgtcgtgt    300
gcagcgagaa cagcctgcag ttcttcatgc ctgtgctggg cgctctgttc atcggagtgg    360
ctgtggctcc tgccaacgac atctacaacg agcgcgagct gctgaacagc atgggcatct    420
ctcagcccac cgtggtgttc gtgtccaaga agggactgca gaaaatcctg aacgtgcaga    480
agaagctgcc catcatccag aaaatcatca tcatggacag caagaccgac taccagggct    540
tccagagcat gtacaccttc gtgaccagcc atctgccatc tggcttcaac gagtacgact    600
tcgtgcccga gagcttcgac agagacaaga caatcgccct gatcatgaac agcagcggct    660
ctaccggact gcccaaaggt gttgctctgc ctcacagaac cgcctgcgtc agattcagcc    720
acgccagaga tcccatcttc ggcaaccaga tcatccccga cacagccatc ctgagcgtgg    780
tgcctttca ccacggcttc ggcatgttca ccacactggg ctacctgatc tgcggcttca    840
gagtggtgct gatgtaccgc ttcgaggaag aactgttcct gagaagcctg caggactaca    900
agatccagtc tgccctgctg gtgcctactc tgttcagctt ctttgccaag agcaccctga    960
tcgataagta cgacctgagc aacctgcacg agatcgctag tggcggagcc cctctgtcta   1020
aagaagtggg cgaagccgtc gccaagaggt tccatctgcc tggcatcaga caaggctacg   1080
gactgaccga gacaaccagc gctatcctga tcacacctga gggcgacgat aagcctggcg   1140
ctgtgggaaa agtggtgcca ttcttcgagg ccaaggtggt ggacctggac accgaaaaaa   1200
cactgggcgt taaccagagg ggcgagctgt gtgtcagagg ccctatgatc atgagcggct   1260
acgtgaacaa ccccgaggcc accaacgctc tgatcgacaa ggatggatgg ctgcacagcg   1320
gcgacattgc ctactgggac gaagatgagc acttcttcat cgtggacaga ctgaagtccc   1380
tgatcaagta caagggctac caggtggccc ctgccgagct ggaatctatc ctgctccagc   1440
atcctaacat cttcgatgcc ggcgtggcag gactgcctga cgatgatgct ggcgaactgc   1500
ctgctgctgt ggtggtgctg aacacggca agaccatgac cgagaaagaa atcgtggact   1560
acgtggccag ccaagtgacc accgccaaga aactgagagg cctgtggtg tttgtggacg   1620
aggtgccaaa aggcctgacc ggcaagctgg acgccagaaa gatcagagag atcctcatca   1680
aggccaagaa aggcggcaag atccgcgtgt gacgcgccat acagcagcaa ttggcaagct   1740
gctctagagc tgccttctgc ggggcttgcc ttctggccat gccttcttc tctcccttgc   1800
acctgtacct cttggtcttt gaataaagcc tgagtaggaa gtgaggggc gccatttcaa   1860
aaaaaaaaa aaaaaaaaa aaaaaaaaaa aaaaaaaaa aaaaaaaaa aaaaaaaaa       1920
aaaaaaaaaa aaaaaaaaaa aaaaaaaaaa aaaaaaaa                           1958

SEQ ID NO: 3           moltype = RNA   length = 952
FEATURE                Location/Qualifiers
source                 1..952
                       mol_type = other RNA
                       organism = synthetic construct
SEQUENCE: 3
gggagaccca agctgccgcc accatggtga gcaagggcga ggagctgttc accggggtgg     60
tgcccatcct ggtcgagctg gacggcgacg taaacggcca caagttcagc gtgtccggcg    120
agggcgaggg cgatgccacc tacggcaagc tgaccctgaa gttcatctgc accaccggca    180
agctgcccgt gccctggccc accctcgtga ccaccctgac ctacggcgtg cagtgcttca    240
gccgctaccc cgaccacatg aagcagcacg acttcttcaa gtccgccatg cccgaaggct    300
acgtccagga gcgcaccatc ttcttcaagg acgacggcaa ctacaagacc cgcgccgagg    360
tgaagttcga gggcgacacc ctggtgaacc gcatcgagct gaagggcatc gacttcaagg    420
aggacggcaa catcctgggg cacaagctgg agtacaacta caacagccac aacgtctata    480
tcatggccga caagcagaag aacggcatca aggtgaactt caagatccgc cacaacatcg    540
aggacggcag cgtgcagctc gccgaccact accagcagaa cacccccatc ggcgacggcc    600
ccgtgctgct gcccgacaac cactacctga gcacccagtc cgccctgagc aaagacccca    660
acgagaagcg cgatcacatg gtcctgctgg agttcgtgac cgccgccggg atcactcctg    720
gcatggacga gctgtacaag taactagagc tgccttctgc ggggcttgcc ttctggccat    780
gccttcttc tctcccttgc acctgtacct cttggtcttt gaataaagcc tgagtaggaa    840
gtgagggtag ggaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aa                       952

SEQ ID NO: 4           moltype = RNA   length = 943
FEATURE                Location/Qualifiers
source                 1..943
                       mol_type = other RNA
                       organism = synthetic construct
SEQUENCE: 4
gggagaccca agctgccgcc accatggtga gcaagggcga ggaggataac atggccatca     60
tcaaggagtt catgcgcttc aaggtgcaca tggagggctc cgtgaacggc cacgagttcg    120
agatcgaggg cgagggcgag ggccgcccct acgagggcac ccagaccgcc aagctgaagg    180
tgaccaaggg tggccccctg cccttcgcct gggacatcct gtcccctcag ttcatgtacg    240
gctccaaggc ctacgtgaag caccccgccg acatccccga ctacttgaag ctgtccttcc    300
ccgagggctt caagtgggag cgcgtgatga acttcgagga cggcggcgtg gtgaccgtga    360
cccaggactc ctccctgcag gacggcgagt tcatctacaa ggtgaagctg cgcggcacca    420
acttcccctc cgacggcccc gtaatgcaga agaagaccat gggctgggag gcctcctccg    480
agcggatgta ccccgaggac ggcgccctga agggcgagat caagcagagg ctgaagctga    540
aggacggcgg ccactacgac gctgaggtca agaccaccta caaggccaag aagcccgtgc    600
agctgccccg cgcctacaac gtcaacatca gttggacat cacctccac aacgaggact    660
acaccatcgt ggaacagtac gaacgcgccg agggccgcca ctccaccggc ggcatgacg    720
agctgtacaa gtagctagag ctgccttctg cggggcttgc cttctggcca tgccttcttt    780
ctctcccttg cacctgtacc tcttggtctt tgaataaagc tgagtaggaa gtgagggta    840
gggaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaa aaa                        943
```

| SEQ ID NO: 5 | moltype = RNA length = 1983 |
|---|---|
| FEATURE | Location/Qualifiers |
| source | 1..1983 |
| | mol_type = other RNA |
| | organism = synthetic construct |

SEQUENCE: 5

```
gggagaccca agctaatgga ctacgacata gtctagtccg ccaagatgaa ggccaacctg   60
ctggtgctgc tgtgtgctct ggctgccgct gatgccgata ccatctgtat cggctaccac  120
gccaacaaca gcaccgacac cgtggatacc gtgctgaaa agaacgtgac cgtgacacac  180
agcgtgaacc tgctcgagga cagccacaat ggcaagctgt gccggctgaa gggaattgcc  240
cctctgcagc tgggcaagtg caatatcgct ggatggctgc tgggcaaccc cgagtgtgat  300
cctctgctgc tgtcagatc ctggtcctac atcgtggaaa cccctaacag cgagaacggc  360
atctgctacc ccgcgactt catcgactac gaggaactga gagaacagct gagcagcgtg  420
tccagcttcg agagattcga gatcttcccc aaagagagca gctggcccaa ccacaacacc  480
aatggcgtga cagccgcctg ttctcacgag ggcaagagca gcttctaccg gaacctgctg  540
tggctgaccg agaagagggg cagctacccc aagctgaaga actcctacgt gaacaagaaa  600
ggcaaagagg tgctggtcct ctggggcatc accatcctc caaacagcaa agagcagcag  660
aacctgtacc agaacgagaa tgcctacgtg tccgtgctga ccagcaacta caaccggcag  720
ttcacacctg agatcgccga gaggcctaaa gtgcgcgatc aggccggcag aatgaactac  780
tactggaccc tgctgaagcc cggcgacacc atcatctttg aggccaacgg caacctgatc  840
gcccctatgt acgccttcgc tctgagcaga ggctttggca cggcatcat cacctccaac  900
gccagatgc acgagtgcaa caccaagtgt cagacacccc tgggcgctat caacagcagc  960
ctgccttacc agaacattca ccccgtgacc atcggcgagt gccccaaata cgtcagatcc 1020
gccaagctga aatggtcac cggcctgaga acatccccca gcatccagtc cagaggcctg 1080
tttggcgcca ttgccggctt tatcgaaggc ggctggaccg catgatcga cggatggtac 1140
ggataccacc accagaatga gcaaggcagc ggctacgacg ccgatcagaa gcacacacag 1200
aacgccatca acggcatcac caacaaagtg aacaccgtga tcgagaagat gaacatccag 1260
ttcaccgccg tgggcaaaga gttcaacaag ctggaaaaac ggatgaaaaa cctcaacaag 1320
aaggtggaca acggcttcct ggacatctgg acctacaatg ccgagctgct cgtgctcctg 1380
gaaaacggga gaaccctgga cttccacgac agcaacgtga agaatctgta cgagaaagtg 1440
aagtcccagc tcaagaacaa cgccaaagag atcggcaacg gctgcttcga gttctaccac 1500
aagtgcgaca acgagtgcat ggaaagcgtg cggaacggca cctacgacta ccctaagtac 1560
agcgaggaaa gcagctgaa ccgcgaaaaa gtggacggcg tgaagctgga atccatgggc 1620
atctaccaga ttctggccat ctacagcacc gtggcctaca gcctggtgct tctggtttct 1680
ctgggcgcca tcagcttttg gatgtgcagc aatggcagcc tgcagtgccg gatctgcatc 1740
tagatacagc agcaattggc aagctgctct agagctgcct tctgcggggc ttgccttctg 1800
gccatgccct tcttctctcc cttgcacctg taccctcttgg tctttgaata aagcctgagt 1860
aggaagtgag ggggcgccat ttcaaaaaaa aaaaaaaaa aaaaaaaaa aaaaaaaaaa 1920
aaaaaaaaaa aaaaaaaaaa aaaaaaaaaa aaaaaaaaaa aaaaaaaaaa aaaaaaaaaa 1980
aaa                                                                1983
```

| SEQ ID NO: 6 | moltype = RNA length = 578 |
|---|---|
| FEATURE | Location/Qualifiers |
| source | 1..578 |
| | mol_type = other RNA |
| | organism = synthetic construct |

SEQUENCE: 6

```
gggagaccca agctaatgga ctacgacata gtctagtccg ccaagtctag gccgccacca   60
tgaagatctc tgccgccgct ctgaccatca tcctgacagc tgctgctctg tgcacccctg  120
ctccagcttc tccatacggc agcgacacca caccttgctg cttcgcctat ctgtctctgg  180
ccctgcctag ggctcacgtg aaagagtact tctacacccc gcaagtgc agcaacctgg  240
ccgtggtgtt cgtgaccaga cggaacagac aagtgtgcgc taaccccgag aagaaatggg  300
tgcaagagta catcaactac ctcgagatga gctgataaat acagcagcaa ttggcaagct  360
gctctagagc tgccttctgc ggggcttgcc ttctggccat gccttcttc tctcccttgc  420
acctgtacct cttggtcttt gaataaagcc tgagtaggaa gtgaggggg gccatttcaa  480
aaaaaaaaaa aaaaaaaaaa aaaaaaaaaa aaaaaaaa aaaaaaaaa aaaaaaaa     540
aaaaaaaaaa aaaaaaaaaa aaaaaaaaaa aaaaaaaa                         578
```

| SEQ ID NO: 7 | moltype = AA length = 511 |
|---|---|
| FEATURE | Location/Qualifiers |
| source | 1..511 |
| | mol_type = protein |
| | organism = Homo sapiens |

SEQUENCE: 7

```
MLGPCMLLLL LLLGLRLQLS LGIIPVEEEN PDFWNREAAE ALGAAKKLQP AQTAAKNLII   60
FLGDGMGVST VTAARILKGQ KKDKLGPEIP LAMDRFPYVA LSKTYNVDKH VPDSGATATA  120
YLCGVKGNFQ TIGLSAAARF NQCNTTRGNE VISVMNRAKK AGKSVGVVTT TRVQHASPAG  180
TYAHTVNRNW YSDADVPASA RQEGCQDIAT QLISNMDIDV ILGGGRKYMF RMGTPDPEYP  240
DDYSQGGTRL DGKNLVQEWL AKRQGARYVW NRTELMQASL DPSVTHLMGL FEPGDMKYEI  300
HRDSTLDPSL MEMTEAALRL LSRNPRGFFL FVEGGRIDHG HHESRAYRAL TETIMFDDAI  360
ERAGQLTSEE DTLSLVTADH SHVFSFGGYP LRGSSIFGLA PGKARDRKAY TVLLYGNGPG  420
YVLKDGARPD VTESESGSPE YRQQSAVPLD EETHAGEDVA VFARGPQAHL VHGVQEQTFI  480
AHVMAFAACL EPYTACDLAP PAGTTDAAHP G                                 511
```

| SEQ ID NO: 8 | moltype = AA length = 550 |
|---|---|
| FEATURE | Location/Qualifiers |
| source | 1..550 |
| | mol_type = protein |
| | organism = Photinus pyralis |

```
SEQUENCE: 8
MEDAKNIKKG PAPFYPLEDG TAGEQLHKAM KRYALVPGTI AFTDAHIEVD ITYAEYFEMS    60
VRLAEAMKRY GLNTNHRIVV CSENSLQFFM PVLGALFIGV AVAPANDIYN ERELLNSMGI   120
SQPTVVFVSK KGLQKILNVQ KKLPIIQKII IMDSKTDYQG FQSMYTFVTS HLPPGFNEYD   180
FVPESFDRDK TIALIMNSSG STGLPKGVAL PHRTACVRFS HARDPIFGNQ IIPDTAILSV   240
VPFHHGFGMF TTLGYLICGF RVVLMYRFEE ELFLRSLQDY KIQSALLVPT LFSFFAKSTL   300
IDKYDLSNLH EIASGGAPLS KEVGEAVAKR FHLPGIRQGY GLTETTSAIL ITPEGDDKPG   360
AVGKVVPFFE AKVVDLDTGK TLGVNQRGEL CVRGPMIMSG YVNNPEATNA LIDKDGWLHS   420
GDIAYWDEDE HFFIVDRLKS LIKYKGYQVA PAELESILLQ HPNIFDAGVA GLPDDDAGEL   480
PAAVVVLEHG KTMTEKEIVD YVASQVTTAK KLRGGVVFVD EVPKGLTGKL DARKIREILI   540
KAKKGGKIAV                                                         550

SEQ ID NO: 9            moltype = AA   length = 239
FEATURE                 Location/Qualifiers
source                  1..239
                        mol_type = protein
                        organism = synthetic construct
SEQUENCE: 9
MVSKGEELFT GVVPILVELD GDVNGHKFSV SGEGEGDATY GKLTLKFICT TGKLPVPWPT    60
LVTTLTYGVQ CFSRYPDHMK QHDFFKSAMP EGYVQERTIF FKDDGNYKTR AEVKFEGDTL   120
VNRIELKGID FKEDGNILGH KLEYNYNSHN VYIMADKQKN GIKVNFKIRH NIEDGSVQLA   180
DHYQQNTPIG DGPVLLPDNH YLSTQSALSK DPNEKRDHMV LLEFVTAAGI TLGMDELYK    239

SEQ ID NO: 10           moltype = AA   length = 236
FEATURE                 Location/Qualifiers
source                  1..236
                        mol_type = protein
                        organism = synthetic construct
SEQUENCE: 10
MVSKGEEDNM AIIKEFMRFK VHMEGSVNGH EFEIEGEGEG RPYEGTQTAK LKVTKGGPLP    60
FAWDILSPQF MYGSKAYVKH PADIPDYLKL SFPEGFKWER VMNFEDGGVV TVTQDSSLQD   120
GEFIYKVKLR GTNFPSDGPV MQKKTMGWEA SSERMYPEDG ALKGEIKQRL KLKDGGHYDA   180
EVKTTYKAKK PVQLPGAYNV NIKLDITSHN EDYTIVEQYE RAEGRHSTGG MDELYK       236

SEQ ID NO: 11           moltype = AA   length = 565
FEATURE                 Location/Qualifiers
source                  1..565
                        mol_type = protein
                        organism = unidentified
SEQUENCE: 11
MKANLLVLLC ALAAADADTI CIGYHANNST DTVDTVLEKN VTVTHSVNLL EDSHNGKLCR    60
LKGIAPLQLG KCNIAGWLLG NPECDPLLPV RSWSYIVETP NSENGICYPG DFIDYEELRE   120
QLSSVSSFER FEIFPKESSW PNHNTNGVTA ACSHEGKSSF YRNLLWLTEK EGSYPKLKNS   180
YVNKKGKEVL VLWGIHHPPN SKEQQNLYQN ENAYVSVVTS NYNRRFTPEI AERPKVRDQA   240
GRMNYYWTLL KPGDTIIFEA NGNLIAPMYA FALSRGFGSG IITSNASMHE CNTKCQTPLG   300
AINSSLPYQN IHPVTIGECP KYVRSAKLRM VTGLRNIPSI QSRGLFGAIA GFIEGGWTGM   360
IDGWYGYHHQ NEQGSGYAAD QKSTQNAING ITNKVNTVIE KMNIQFTAVG KEFNKLEKRM   420
ENLNKKVDDG FLDIWTYNAE LLVLLENERT LDFHDSNVKN LYEKVKSQLK NNAKEIGNGC   480
FEFYHKCDNE CMESVRNGTY DYPKYSEESK LNREKVDGVK LESMGIYQIL AIYSTVASSL   540
VLLVSLGAIS FWMCSNGSLQ CRICI                                        565

SEQ ID NO: 12           moltype = AA   length = 91
FEATURE                 Location/Qualifiers
source                  1..91
                        mol_type = protein
                        organism = Mus musculus
SEQUENCE: 12
MKISAAALTI ILTAAALCTP APASPYGSDT TPCCFAYLSL ALPRAHVKEY FYTSSKCSNL    60
AVVFVTRRNR QVCANPEKKW VQEYINYLEM S                                   91

SEQ ID NO: 13           moltype = DNA   length = 1838
FEATURE                 Location/Qualifiers
source                  1..1838
                        mol_type = other DNA
                        organism = synthetic construct
misc_feature            1..1835
                        note = RNA
misc_feature            1836..1838
                        note = DNA
SEQUENCE: 13
gggagaccca agctaatgga ctacgacata gtctagtccg ccaagtctag gccgccacca    60
tgctggggcc ctgcatgctg ctgctgctgc tgctgctggg cctgaggcta cagctctccc   120
tgggcatcat cccagttgag gaggagaacc cggacttctg gaaccgcgag gcagccgagg   180
cctgtgtgtg cgccaagaag ctgcagcctg cacagcaggt gccaagaac ctcatcatct   240
tcctgggcga tgggatgggg gtgtctacgg tgacagctgc caggatccta aaagggcaga   300
agaaggacaa actgggccct gagataccc tggccatgga ccgcttccca tatgtggctc   360
tgtccaagac atacaatgta gacaaacatg tgccagacag tggagccaca gccacggcct   420
acctgtgcgg ggtcaagggc aacttccaga ccattggctt gagtgcagcc gccgctttta   480
accagtgcaa cacgacacgc ggcaacgagg tcatctccgt gatgaatcgg gccaagaaag   540
```

```
cagggaagtc agtgggagtg gtaaccacca cacgagtgca gcacgcctcg ccagccggca    600
cctacgccca cacggtgaac cgcaactggt actcggacgc cgacgtgcct gcctccgccc    660
gccaggaggg gtgccaggac atcgctacgc agctcatctc caacatggac attgacgtga    720
tcctaggtgg aggccgaaag tacatgtttc gcatgggaac cccagaccct gagtaccag     780
atgactacag ccaaggtggg accaggctgg acgggaagac tctggtgcag gaatggctgg    840
cgaagcgcca gggtgccgg tatgtgtgga accgcactga gctcatgcag gcttccctgg     900
acccgtctgt gacccatctc atgggtctct ttgagcctgg agacatgaaa tacgagatcc    960
accgagactc cacactggac ccctccctga tggagatgca gaggctgcc ctgcgcctgc    1020
tgagcaggaa ccccgcggc ttcttcctct tcgtggaggg tggtcgcatc gaccatggtc    1080
atcatgaaaa cagggcttac cgggactga ctgagacgat catgttcgac gacgccattg    1140
agagggcggg ccagctcacc agcgaggagg acacgctgag cctcgtcact gccgaccact    1200
cccacgtctt ctccttcgga ggctaccccc tgcgagggag ctccatcttc gggctggccc    1260
ctggcaaggc ccgggacagg aaggcctaca cggtcctcct atacggaaac ggtccaggct    1320
atgtgctcaa ggacggcgcc cggccggatg ttaccgagag cgagagcggg agccccgact    1380
atcggcagca gtcagcagtg ccctggacg aagagaccca cgcaggcgag gacgtggcgg    1440
tgttcgcgcg cggccgcag gcgcacctgg ttcacggcgt gcaggagcag accttcatag    1500
cgcacgtcat ggccttcgcc gcctgcctgg agccctacac cgcctgcgac ctggcgcccc    1560
ccgccggcac caccgacgcc gcgcaccggg ggtgaataca gcagcaattg gcaagctgct    1620
ctagagctgc cttctgcggg gcttgccttc tggccatgcc cttcttctct cccttgcacc    1680
tgtacctctt ggtctttgaa taaagcctga gtaggaagtg aggggcgcc atttcaaaaa     1740
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaa aaaaaaaa                             1838

SEQ ID NO: 14           moltype = DNA   length = 1961
FEATURE                 Location/Qualifiers
source                  1..1961
                        mol_type = other DNA
                        organism = synthetic construct
misc_feature            1..1958
                        note = RNA
misc_feature            1959..1961
                        note = DNA
SEQUENCE: 14
gggagaccca agctaatgga ctacgcacata gtctagtccg ccaagtctag gcgccacca     60
tggaagatgc caagaacatc aagaagggcc ctgctccatt ctaccctctg gaagatggaa    120
cagccggcga gcagctgcac aaggccatga gagatacgc tctggtgccc ggcacaatcg    180
ccttcacaga tgctcacatc gaggtggaca tcacctacgc cgagtacttc gagatgtctg    240
tgcggctggc cgaagctatg aagcgctacg gcctgaacac caaccacaga atcgtcgtgt    300
gcagcgagaa cagcctgcag ttcttcatgc ctgtgctggg cgctctgttc atcggagtgg    360
ctgtggctcc tgccaacgac atctacaacg agcgcgagct gctgaacagc atgggcatct    420
ctcagcccac cgtggtgttc gtgtccaaga agggactgca gaaaatcctg aacgtgcaga    480
agaagctgcc catcatccag aaaatcatca tcatggacag caagaccgac taccaggct    540
tccagagcat gtacacctc gtgaccagcc atctgccatc tggcttcaac gagtacgact    600
tcgtgcccga gagcttcgac agagacaaga atcagcgcct gatcatgaac agcagcggct    660
ctaccggact gcccaaaggt gttgctctgc ctcacagaac cgcctgcgtc agattcagcc    720
acgccagaga tcccatcttc ggcaaccaga tcatccccga cacagccatc ctgagcgtgg    780
tgccttttca ccacggcttc ggcatgttca ccacactggg ctacctgatc tgcggcttca    840
gagtggtgct gatgtaccgc ttcgaggaag aactgttcct gagaagcctg caggactaca    900
agatccagtc tgccctgctg gtgccactac tgttcagctt ctttgccaag agcaccctga    960
tcgataagta cgacctgagc aacctgcacg agatcgctag tggcggagcc cctctgtcta   1020
aagaagtggg cgaagccgtc gccaagaggt tccatctgcc tggcatcaga caaggctgga   1080
gactgaccga gacaaccagc gctatcctga tcacacctga gggcgacgat aagcctggcc   1140
ctgtgggaaa agtggtgcca ttcttcgagg ccaaggtggt ggacctgac accgaaaaaa   1200
cactgggcgt taaccagagg ggcgagctgt gtgtcagagg cccaatgatc atgagcggct   1260
acgtgaacaa ccccgaggcc accaacgctc tgatcgacaa ggatggatgg ctgcacagcg   1320
gcgacattgc ctactgggac gaagatgagc acttcttcat cgtggacaga ctgaagtccc   1380
tgatcaagta caagggctac caggtggccc ctgccgagct ggaatctatc ctgctccagc   1440
atcctaacat cttcgatgcc ggcgtggcag gactgcctga cgatgatgct ggcgaactgc   1500
ctgctgctgt ggtggtgctg gaacacggca agaccatgac cgagaaagaa atcgtggact   1560
acgtggccag ccaagtgacc accgccaaga actgagagg cggcgtggtg ttgtggacg    1620
aggtgccaaa aggcctgacc ggcaagctgg acgccagaaa gatcagagag atcctcatca   1680
aggcaagaa aggcggcaag atccgcgtgt gacgcgccat acagcagcaa ttggcaagct   1740
gctctagagc tgccttctgc ggggcttgcc ttctggccat gcccttcttc tctcccttgc   1800
acctgtaacct cttggtctttt gaataaaagcc tgagtaggaa gtgaggggggc gccatttcaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa a                       1961

SEQ ID NO: 15           moltype = DNA   length = 955
FEATURE                 Location/Qualifiers
source                  1..955
                        mol_type = other DNA
                        organism = synthetic construct
misc_feature            1..952
                        note = RNA
misc_feature            953..955
                        note = DNA
SEQUENCE: 15
gggagaccca agctgccgcc accatggtga gcaagggcga ggagctgttc accggggtgg     60
tgcccatcct ggtcgagctg gacggcgacg taaacggcca caagttcagc gtgtccggcg    120
```

```
agggcgaggg cgatgccacc tacggcaagc tgaccctgaa gttcatctgc accaccggca    180
agctgcccgt gccctggccc accctcgtga ccaccctgac ctacggcgtg cagtgcttca    240
gccgctaccc cgaccacatg aagcagcacg acttcttcaa gtccgccatg cccgaaggct    300
acgtccagga gcgcaccatc ttcttcaagg acgacggcaa ctacaagacc cgcgccgagg    360
tgaagttcga gggcgacacc ctggtgaacc gcatcgaact gaagggcatc gacttcaagg    420
aggacggcaa catcctgggg cacaagctgg agtacaacta caacagccac aacgtctata    480
tcatggccga caagcagaag aacggcatca aggtgaactt caagatccgc cacaacatcg    540
aggacggcag cgtgcagctc gccgaccact accagcagaa caccccatc ggcgacggcc    600
ccgtgctgct gcccgacaac cactacctga gcacccagtc cgccctgagc aaagacccca    660
acgagaagcg cgatcacatg gtcctgctgg agttcgtgac cgccgccggg atcactctcg    720
gcatggacga gctgtacaag taactagagc tgccttctgc ggggcttgcc ttctggccat    780
gcccttcttc tctcccttgc acctgtacct cttggtcttt gaataaagcc tgagtaggaa    840
gtgagggtag ggaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaa         955

SEQ ID NO: 16           moltype = DNA   length = 946
FEATURE                 Location/Qualifiers
source                  1..946
                        mol_type = other DNA
                        organism = synthetic construct
misc_feature            1..943
                        note = RNA
misc_feature            944..946
                        note = DNA
SEQUENCE: 16
gggagaccca agctgccgcc accatggtga gcaagggcga ggaggataac atggccatca    60
tcaaggagtt catgcgcttc aaggtgcaca tggagggctc cgtgaacggc cacgagttcg    120
agatcgaggg cgagggcgag ggcgccccct acgagggcac ccagaccgcc aagctgaagg    180
tgaccaaggg tggccccctg cccttcgcct gggacatcct gtcccctcag ttcatgtacg    240
gctccaaggc ctacgtgaag caccccgccg acatcccga ctacttgaag ctgtcttcc     300
ccgagggctt caagtgggag cgcgtgatga cttccgagga cggcggcgtg gtgaccgtga    360
cccaggactc ctccctgcag gacggcgagt tcatctacaa ggtgaagctg cgcggcacca    420
acttcccctc cgacggcccc gtaatgcaga gaagaccat gggctgggag gcctcctccg    480
agcggatgta ccccgaggac ggcgccctga agggcgagat caagcagagg ctgaagctga    540
aggacggcgg ccactacgac gctgaggtca agaccaccta caaggccaag agcccgtgc    600
agctgcccgg cgcctacaac gtcaacatca gttggacat cacctccac aacgaggact    660
acaccatcgt ggaacagtac gaacgcgccg agggccgcca ctccaccggc ggcatggacg    720
agctgtacaa gtagctagag ctgccttctg cggggcttgc cttctggcca tgcccttctt    780
ctctcccttg cacctgtacc tcttggtctt tgaataaagc ctgagtagga agtgagggta    840
gggaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaa                    946

SEQ ID NO: 17           moltype = DNA   length = 1986
FEATURE                 Location/Qualifiers
source                  1..1986
                        mol_type = other DNA
                        organism = synthetic construct
misc_feature            1..1983
                        note = RNA
misc_feature            1984..1986
                        note = DNA
SEQUENCE: 17
gggagaccca agctaatgga ctacgacata gtctagtccg ccaagatgaa ggccaacctg    60
ctggtgctgc tgtgtgctct ggctgccgct gatgccgata ccatctgtat cggctaccac    120
gccaacaaca gcaccgacac cgtggatacc gtgctgaaa agaacgtgac cgtgacacac    180
agcgtgaacc tgctcgagga cagccacaat ggcaagctgt gccggctgaa gggaattgcc    240
cctctgcagc tgggcaagtg caatatcgct ggatggctgc tgggcaaccc cgagtgtgat    300
cctctgctgc ctgtcagatc ctggtcctac atcgtgaaaa cccctaacag cgagaacggc    360
atctgctacc ccggcgactt catcgactac gaggaactga gagaacagct gagcagcgtg    420
tccagcttcg agagattcga gatcttcccc aaagagagca gctgccaa ccacaacacc    480
aatgccgtga cagccgcctg ttctcacgag ggcaagagca gcttctaccg gaacctgctg    540
tggctgaccg agaagagggg cagctacccc aagctgaaga actcctacgt gaacaagaaa    600
ggcaaagagg tgctggtcct ctgggggatc accatcctc aaacagcaa agagcagcag    660
aacctgtacc agaacgagaa tgcctacgtg tccgtggtca cgacaacta caaccggctg    720
ttcacacctg agatcgccga gaggcctaaa gtgcgcgatc aggccggcag aatgaactac    780
tactggaccc tgctgaagcc cggcgacacc atcatctttg aggccaacgg caacctgatc    840
gcccctatgt acgccttcgc tctgagcaga ggctttggca gcggcatcat cacctccaac    900
gccacatgc acgaagtgca caccaaatg caggacaaccc tggcgctat caacagcagc    960
ctgccttacc agaacattca cccctgtacc atcggcgagt gccccaata cgtcagatcc    1020
gccaagctga atggtcac cggcctgaga acatccccca gcatccagtc cagaggcctg    1080
tttggcgcca ttgccggctt tatcgaaggc ggctggaccg gcatgatcga cggatggtac    1140
ggataccacc accagaatga gcaaggcagc ggctacgccg ccgatcagaa aagcacacag    1200
aacgccatca acggcatcac caacaaagtg aacaccgtga tcgagaagat gaacatccag    1260
ttcaccgccg tgggcaaaga gttcaacaag ctggaaaaac ggatggaaaa cctcaacaag    1320
aaggtggacg acggctcct ggacatctgg acctacaatg ccgagctgct cgtgctcctg    1380
gaaaacgaga gaaccctgga cttccacgac agcaacgtga gaatctgta cgagaaagtg    1440
aagtcccagc tcaagaacaa cgccaaagag atcggcaacg gctgcttcga gttctaccac    1500
aagtgcgaca acacgagtgcat ggaaagcgtg cggaacggca cctacgacta ccctaagtac    1560
agcgaggaaa gcaagctgaa ccgcgaaaaa gtggacggcg tgaagctgga atccatgggc    1620
```

```
atctaccaga ttctggccat ctacagcacc gtggcctcta gcctggtgct tctggttttct    1680
ctgggcgcca tcagcttttg gatgtgcagc aatggcagcc tgcagtgccg gatctgcatc    1740
tagatacagc agcaattggc aagctgctct agagctgcct tctgcggggc ttgccttctg    1800
gccatgccct tcttctctcc cttgcacctg tacctcttgg tctttgaata aagcctgagt    1860
aggaagtgag ggggcgccat ttcaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaa                                                                1986

SEQ ID NO: 18         moltype = DNA   length = 581
FEATURE               Location/Qualifiers
source                1..581
                      mol_type = other DNA
                      organism = synthetic construct
misc_feature          1..578
                      note = RNA
misc_feature          579..581
                      note = DNA
SEQUENCE: 18
gggagaccca agctaatgga ctacgacata gtctagtccg ccaagtctag gccgccacca     60
tgaagatctc tgccgccgct ctgaccatca tcctgacagc tgctgctctg tgcacccctg    120
ctccagcttc tccatacggc agcgacacca caccttgctg cttcgccta t ctgtctctgg    180
ccctgcctag ggctcacgtg aaagagtact tctacaccag cagcaagtgc agcaacctgg    240
ccgtggtgtt cgtgaccaga cggaacagac aagtgtgcgc taaccccgag aagaaatggg    300
tgcaagagta catcaactac ctcgagatga gctgataaat acagcagcaa ttggcaagct    360
gctctagagc tgccttctgc ggggcttgcc ttctggccat gccttcttc tctcccttgc    420
acctgtacct cttggtcttt gaataaagcc tgagtagtga gtgaggggc gccatttcaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa a                        581

SEQ ID NO: 19         moltype = RNA   length = 1652
FEATURE               Location/Qualifiers
source                1..1652
                      mol_type = other RNA
                      organism = synthetic construct
SEQUENCE: 19
gggagaccca agctaatgga ctacgacata gtctagtccg ccaagtctag gccgccacca     60
tggaggtgca gctggtggag agcggcggcg gcctggtgca gcccggcggc agcctgcgcc    120
tgagctgcgc cgcgcagcggc ttcaacatca aggacaccta catccactgg gtgcgccagg    180
cccccggcaa gggcctggag tgggtggccc gcatctaccc caccagcggc tacacccgct    240
acgccgacag cgtgaagggc cgcttcacca tcagcgccga ccagcagaag aacaccgcct    300
acctgcagat gaacagcctg cgcgccgagg acaccgccgt gtactactgc agccgctggg    360
gcggcgacgg cttctacgcc atggactact ggggccaggg caccctggtg accgtgagca    420
gcgccagcac caaggggccc cagcgtgttcc ccctggccccc agcagcaag agcaccagcg    480
gcggcaccgc cgccctgggc tgcctggtga aggactactt ccccgagccc gtgaccgtga    540
gctggaacag cggcgccctg accagcggcg tgcacacctt ccccgccgtg ctgcagagca    600
gcggcctgta cagcctgagc agcgtggtga ccgtgcccag cagcagcctg ggcacccaga    660
cctacatctg caacgtgaac cacaagccca gcaacaccaa ggtggacaag aaggttgagc    720
ccaagagctg cgacaagacc cacacctgcc cccctgccc cgccccgag ctgctgggcg    780
gccccagcgt gttcctgttc cccccaagc caaggacac cctgatgatc agccggcaccc    840
ccgaggtgac ctgcgtggtg gtggacgtga gccacgagga ccccgaggtg aagttcaact    900
ggtacgtgga cggcgtggag gtgcacaacg ccaagaccaa gccccgcgag gagcagtaca    960
acagcaccta ccgcgtggtg agcgtgctga ccgtgctgca ccaggactgg ctgaacggca    1020
aggagtacaa gtgcaaggtg agcaacaagg ccctgcccgc cccatcgag aagaccatca    1080
gcaaggccaa gggccagccc cgcgagcccc aggtgtacac cctgccccc agccgcgagg    1140
agatgaccaa gaaccaggtg agcctgacct gcctggtgaa gggcttctac cccagcgaca    1200
tcgccgtgga gtgggagagc aacggccagc ccgagaacaa ctacaagacc accccccccg    1260
tgctggacag cgacggcagc ttcttcctgt acagcaagct gaccgtggac aagagccgct    1320
ggcagcaggg caacgtgttc agctgcagcg tgatgcacga ggcctgcac aaccactaca    1380
cccagaaaag cctgagcctg agccccggct gaatacagcca gcaattggca agctgctcta    1440
gagctgcctt ctgcggggct tgccttctgg ccatgccctt cttctctcc ttgcacctgt    1500
acctcttggt ctttgaataa gcctgagta ggaagtgagg gggcgccatt tcaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aa                                  1652

SEQ ID NO: 20         moltype = RNA   length = 950
FEATURE               Location/Qualifiers
source                1..950
                      mol_type = other RNA
                      organism = synthetic construct
SEQUENCE: 20
gggagaccca agctaatgga ctacgacata gtctagtccg ccaagtctag gccgccacca     60
tgggcgacat ccagatgacc cagagcccca gcagcctgag cgccagcgtg ggcgaccgcg    120
tgaccatcac ctgccgcgcc agccaggacg tgaacaccgc cgtggcctgg taccagcaga    180
agcccggcaa ggcccccaag ctgctgatct acagcgccta cttcctgtac agcggcgtgc    240
ccagccgctt cagcggcagc cgcagcggca ccgacttcac cctgaccatc agcagcctgc    300
agcccgagga cttcgccacc tactactgca gcagcacta ccaccacccc ccacctttcg    360
gccagggcac caaggtggag atcaagcgca ccgtggccgc cccagccgtg ttcatcttcc    420
ccccagccga cgagcagctg aagagcggca ccgccagcgt ggtgtgcctg ctgaacaact    480
tctacccccg cgaggccaag gtgcagtgga aggtggacaa cgccctgcag agcggcaaca    540
```

```
gccaggagag cgtgaccgag caggacagca aggacagcac ctacagcctg agcagcaccc   600
tgaccctgag caaggccgac tacgagaagc acaaggtgta cgcctgcgag gtgacccacc   660
agggcctgag cagccccgtg accaagagct caaccgcgg cgagtgctga atacagcagc   720
aattggcaag ctgctctaga gctgccttct gcggggcttg ccttctggcc atgcccttct   780
tctctccctt gcacctgtac ctcttggtct ttgaataaag cctgagtagg aagtgagggg   840
gcgccatttc aaaaaaaaaa aaaaaaaaaa aaaaaaaaaa aaaaaaaaaa aaaaaaaaaa   900
aaaaaaaaaa aaaaaaaaaa aaaaaaaaaa aaaaaaaaaa aaaaaaaaaa              950

SEQ ID NO: 21           moltype = AA   length = 450
FEATURE                 Location/Qualifiers
source                  1..450
                        mol_type = protein
                        organism = synthetic construct
SEQUENCE: 21
MEVQLVESGG GLVQPGGSLR LSCAASGFNI KDTYIHWVRQ APGKGLEWVA RIYPTNGYTR    60
YADSVKGRFT ISADTSKNTA YLQMNSLRAE DTAVYYCSRW GGDGFYAMDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                    450

SEQ ID NO: 22           moltype = AA   length = 216
FEATURE                 Location/Qualifiers
source                  1..216
                        mol_type = protein
                        organism = synthetic construct
SEQUENCE: 22
MGDIQMTQSP SSLSASVGDR VTITCRASQD VNTAVAWYQQ KPGKAPKLLI YSASFLYSGV    60
PSRFSGSRSG TDFTLTISSL QPEDFATYYC QQHYTTPPTF GQGTKVEIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216
```